(12) United States Patent
Takaku et al.

(10) Patent No.: US 11,563,178 B2
(45) Date of Patent: Jan. 24, 2023

(54) ORGANIC ELECTROLUMINESCENT ELEMENT, COMPOUND FOR USE IN THE ELEMENT, AND LIGHT EMITTING DEVICE, DISPLAY DEVICE, AND ILLUMINATION DEVICE USING THE ELEMENT

(71) Applicant: UDC IRELAND LIMITED, Dublin (IE)

(72) Inventors: Koji Takaku, Kanagawa (JP); Yasunori Yonekuta, Kanagawa (JP); Wataru Sotoyama, Kanagawa (JP); Katsuyuki Youfu, Kanagawa (JP); Yuki Hirai, Kanagawa (JP); Tetsu Kitamura, Kanagawa (JP); Toru Watanabe, Kanagawa (JP); Tianhua Ouyang, Kanagawa (JP)

(73) Assignee: UDC IRELAND LIMITED, Dublin (IE)

( * ) Notice: Subject to any disclaimer, the term of this patent is extended or adjusted under 35 U.S.C. 154(b) by 831 days.

(21) Appl. No.: 15/806,660

(22) Filed: Nov. 8, 2017

(65) Prior Publication Data
US 2018/0069179 A1    Mar. 8, 2018

Related U.S. Application Data

(63) Continuation of application No. 13/677,710, filed on Nov. 15, 2012, now abandoned.

(30) Foreign Application Priority Data

Nov. 18, 2011 (JP) .................................. 2011-252533

(51) Int. Cl.
*H01L 51/00* (2006.01)
*C07C 211/54* (2006.01)
(Continued)

(52) U.S. Cl.
CPC ........ *H01L 51/0058* (2013.01); *C07C 211/54* (2013.01); *C07C 211/58* (2013.01);
(Continued)

(58) Field of Classification Search
CPC . C07C 2103/50; C07C 211/54; C07C 211/58; C07D 213/74; C07D 239/42;
(Continued)

(56) References Cited

U.S. PATENT DOCUMENTS

2002/0055014 A1* 5/2002 Okada ................. H01L 51/0072
428/690
2003/0027016 A1   2/2003 Ara
(Continued)

FOREIGN PATENT DOCUMENTS

JP   2003201472   7/2003
JP   2004204238   7/2004
(Continued)

OTHER PUBLICATIONS

Figueira-Duarte et al., Chem. Rev., (2011), vol. 111, pp. 7260-7314 (Year: 2011).*
(Continued)

*Primary Examiner* — Dawn L Garrett
(74) *Attorney, Agent, or Firm* — Riverside Law LLP

(57) ABSTRACT

The disclosure relates to organic electroluminescent elements, compounds for use in the elements, and devices using
(Continued)

the elements, which include a compound represented by the following General Formula (1):

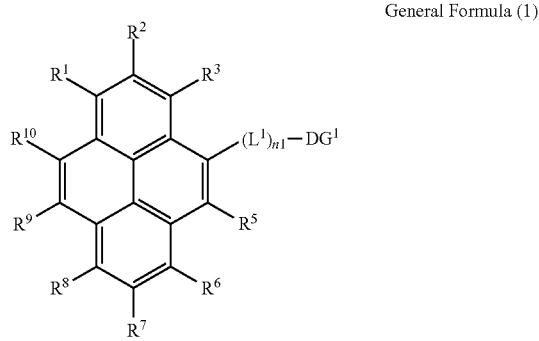

General Formula (1)

where $R^1$ to $R^3$ and $R^6$ to $R^8$ each independently represents a hydrogen atom, which may be a deuterium atom, or a substituent with a Hammett substituent constant $\sigma_p$ value of −0.15 or more, $R^5$, $R^9$ and $R^{10}$ each independently represents a hydrogen atom or a substituent, $L^1$ represents a divalent linking group, $DG^1$ represents a donor group, and n1 represents 1 or 2, and where $R^1$ to $R^3$, $R^5$ to $R^{10}$, $L^1$, and $DG^1$ are not bound to each other to form a ring.

11 Claims, 1 Drawing Sheet

(51) Int. Cl.
    *C07D 213/74*      (2006.01)
    *C07D 333/36*      (2006.01)
    *C07D 401/10*      (2006.01)
    *C07D 239/42*      (2006.01)
    *C07D 241/20*      (2006.01)
    *C07D 263/48*      (2006.01)
    *C07D 493/04*      (2006.01)
    *C07D 495/04*      (2006.01)
    *C07D 307/66*      (2006.01)
    *C07D 307/91*      (2006.01)
    *C07C 211/58*      (2006.01)

(52) U.S. Cl.
CPC ......... *C07D 213/74* (2013.01); *C07D 239/42* (2013.01); *C07D 241/20* (2013.01); *C07D 263/48* (2013.01); *C07D 307/66* (2013.01); *C07D 307/91* (2013.01); *C07D 333/36* (2013.01); *C07D 401/10* (2013.01); *C07D 493/04* (2013.01); *C07D 495/04* (2013.01); *H01L 51/006* (2013.01); *H01L 51/0054* (2013.01); *C07C 2603/50* (2017.05); *H01L 51/0061* (2013.01); *H01L 51/0065* (2013.01); *H01L 51/0067* (2013.01); *H01L 51/0068* (2013.01); *H01L 2251/308* (2013.01)

(58) Field of Classification Search
CPC .. C07D 241/20; C07D 263/48; C07D 307/66; C07D 307/91; C07D 333/36; C07D 401/10; C07D 493/04; C07D 495/04; H01L 2251/308; H01L 51/0054; H01L 51/0058; H01L 51/006; H01L 51/0061; H01L 51/0065; H01L 51/0067; H01L 51/0068; C09K 11/06
See application file for complete search history.

(56) References Cited

U.S. PATENT DOCUMENTS

| | | | |
|---|---|---|---|
| 2003/0118866 | A1 | 6/2003 | Oh |
| 2004/0062950 | A1* | 4/2004 | Iwanaga ............... H05B 33/14 428/690 |
| 2006/0251925 | A1 | 11/2006 | Hosokawa |
| 2008/0119671 | A1 | 5/2008 | Suzuki |
| 2008/0145698 | A1* | 6/2008 | Heil ....................... C09K 11/06 428/690 |

FOREIGN PATENT DOCUMENTS

| | | |
|---|---|---|
| JP | 2007186449 | 7/2007 |
| JP | 2008127291 | 6/2008 |
| JP | 2009283899 | 12/2009 |
| KR | 102010075101 | 7/2010 |
| KR | 20110057008 | 5/2011 |
| KR | 1020120117675 | 10/2012 |
| WO | 0206091 A1 | 8/2002 |
| WO | 2012141273 | 10/2012 |

OTHER PUBLICATIONS

Duan et al., J. Mater. Chem., (2010), vol. 20, pp. 6392-6407. (Year: 2010).*
Machine translation for KR 10-2012-0117675 (publication date: Oct. 2012). (28 pages).

* cited by examiner

ORGANIC ELECTROLUMINESCENT ELEMENT, COMPOUND FOR USE IN THE ELEMENT, AND LIGHT EMITTING DEVICE, DISPLAY DEVICE, AND ILLUMINATION DEVICE USING THE ELEMENT

CROSS-REFERENCE TO RELATED APPLICATIONS

The present application is a continuation of U.S. patent application Ser. No. 13/677,710, filed on Nov. 15, 2012, which claims priority to Japanese Patent Application No. 2011-252533, filed Nov. 18, 2011, each of which is incorporated herein by reference in its entirety.

FIELD OF THE INVENTION

The present invention relates to organic electroluminescent elements, and compounds usable therefor. The present invention also relates to light emitting devices, display devices, and illumination devices using the organic electroluminescent elements.

BACKGROUND ART

Since organic electroluminescent elements (which may hereinafter also be referred to as "elements" or "organic EL elements") are capable of high-luminance light emitting using low voltage driving, they have been actively researched and developed. The organic electroluminescent elements have a pair of electrodes and an organic layer between the pair of electrodes, and utilize, for light emitting, energy of the exciton generated as a result of recombination of the electron injected from the cathode and the hole injected from the anode in the organic layer. The organic electroluminescent elements can provide elements having diverse light emitting wavelengths, and since they have a high response speed and are relatively thin and light-weight, it is expected that they can be employed in a wide range of applications. Among these, it is important to develop an organic electroluminescent element having high color purity and luminous efficiency in light of the applications in full-color displays and the like, and the outcomes have been reported of various research and development studies up to now.

Compounds having a pyrene ring skeleton are known as excellent blue fluorescent material, and represent an example of the material of such organic electroluminescent elements. Among such compounds, many 1,6-substituted pyrenes are known as examples of light emitting materials (see, for example, JP-A-2006-298793, JP-A-2004-204238, and KR10-2011-0057008).

JP-A-2006-298793 describes pyrene compounds having diphenylamino group-substituted phenyl groups across the pyrene ring on the long axis (positions 1, 2, 3, 6, 7, and 8) of the pyrene ring. It is disclosed in the Examples of this publication that a high emission-luminance, high heat-resistance, and long-life organic EL element having excellent high-temperature preservability could be produced when a pyrene compound having diphenylamino group-substituted phenyl groups at positions 1 and 6 of the pyrene ring was used as the dopant of a light emitting layer.

JP-A-2004-204238 describes pyrene compounds having substituted amino groups such as diphenylamino groups across the ring on the long axis (positions 1, 2, 3, 6, 7, and 8). It is disclosed in the Examples of this publication that an organic EL element having excellent blue color purity and luminous efficiency could be produced when a pyrene compound having diphenylamino groups at positions 1 and 6 of the pyrene ring was used as the dopant of a light emitting layer.

KR10-2011-0057008 describes pyrene compounds, similar to those described in JP-A-2004-204238, having substituted amino groups such as diphenylamino groups across the ring on the long axis (positions 1, 2, 3, 6, 7, and 8).

On the other hand, there are not many known examples of pyrene compounds substituted at positions 4 and 9 or positions 4 and 10. For example, JP-A-2009-283899 describes pyrene compounds having 2-phenylnaphthalene and other aryl groups or heteroaryl groups across the ring on the short axis (positions 4, 5, 9, and 10). However, the only example in which the pyrene compounds are used in the Examples of this publication is one in which a compound having a 2-phenylnaphtyl group at pyrene position 4 and a terphenyl group at position 9 is used as a host material of a light emitting layer in combination with a green-emitting material. Further, JP-A-2009-283899 merely describes host materials having a 2-phenylnaphthalene structure as being desirable, and does not describe preferred specific light emitting material structures or preferred specific substitution positions.

Under these circumstances, the present inventors studied the pyrene compounds described in the foregoing publications by using these compounds as light emitting materials of organic electroluminescent elements, and found that the pyrene compounds described in JP-A-2006-298793 and JP-A-2004-204238 had longer wavelengths, and were unable to realize high blue color purity in an organic electroluminescent element.

It was also found that the pyrene compounds described in KR10-2011-0057008, and the compounds described in JP-A-2009-283899 did not have sufficient performance (including luminous efficiency) as light emitting material, and had poor chromaticity.

SUMMARY OF THE INVENTION

Accordingly, there is a need for an organic electroluminescent element that has sufficient luminous efficiency and excellent chromaticity.

The present inventors conducted intensive studies to solve the foregoing problems, and found that pyrene compounds having substituents across the pyrene ring on the long axis (for example, positions 1 and 6) of the pyrene ring has the tendency to have insufficient chromaticity at longer wavelengths, whereas pyrene compounds having substituents across the ring on the short axis (for example, positions 4 and 9, and positions 4 and 10) has short wavelengths, and can provide sufficient chromaticity.

Upon further studies, the present inventors found that sufficient performance as light emitting material can be imparted when a pyrene compound does not have an electron donating group in the substituents across the pyrene ring on the long axis of the pyrene ring, but has an electron donating substituent in the substituents across the pyrene ring on the short axis of the pyrene ring. It was also found that high heat resistance can be imparted when no fused ring structure is formed by the binding of the substituents across the pyrene ring on the short axis of the pyrene ring and any other substituent of the pyrene ring.

The present invention provides specific means to solve the foregoing problems, as follows.

[1] An organic electroluminescent element comprising:
a substrate;
a pair of electrodes including an anode and a cathode, disposed on the substrate; and
an organic layer disposed between the electrodes,
wherein the organic layer contains a compound represented by the following General Formula (1),

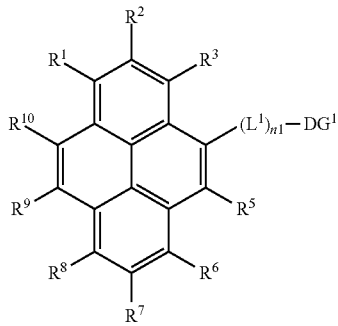

General Formula (1)

(wherein, in General Formula (1), $R^1$ to $R^3$ and $R^6$ to $R^8$ each independently represent a hydrogen atom (including a deuterium atom) or a substituent with a Hammett substituent constant $\sigma_p$ value of −0.15 or more, $R^5$, $R^9$ and $R^{10}$ each independently represent a hydrogen atom or a substituent, $L^1$ represents a divalent linking group, $DG^1$ represents a donor group, and n1 represents 1 or 2, however, $R^1$ to $R^3$, $R^5$ to $R^{10}$, $L^1$, and $DG^1$ are not bound to each other to form a ring).

[2] It is preferable in the organic electroluminescent element according to [1] that the compound represented by the General Formula (1) be a compound represented by following General Formula (2),

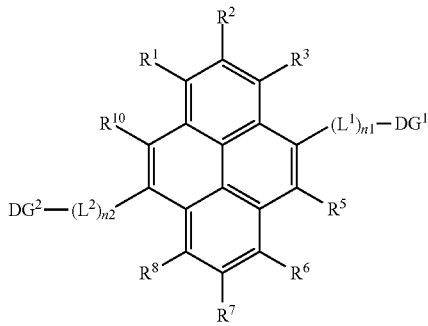

General Formula (2)

(wherein, in General Formula (2), $R^1$ to $R^3$ and $R^6$ to $R^8$ each independently represent a hydrogen atom (including a deuterium atom) or a substituent with a Hammett substituent constant $\sigma_p$ value of −0.15 or more, $R^5$ and $R^{10}$ each independently represent a hydrogen atom or a substituent, $L^1$ and $L^2$ each independently represent a divalent linking group, $DG^1$ and $DG^2$ each independently represent a donor group, and n1 and n2 each independently represent 1 or 2, however, $R^1$ to $R^3$, $R^5$ to $R^8$, $R^{10}$, $L^1$, $L^2$, $DG^1$ and $DG^2$ are not bound to each other to form a ring).

[3] It is preferable in the organic electroluminescent element according to [1] or [1] that, in the General Formulae (1) and (2), the donor group represent —NY$^1$Y$^2$, —OY$^3$ or —SY$^4$ (Y$^1$ to Y$^4$ each independently represent an alkyl group, an aryl group or a heteroaryl group, and any of these may have further substituents), or be represented by following General Formula (A),

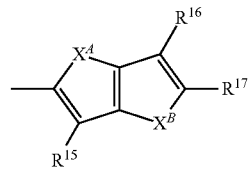

General Formula (A)

(wherein, in General Formula (A), $X^A$ and $X^B$ each independently represent O, S or NY$^{15}$, $R^{15}$ to $R^{17}$ each independently represent a hydrogen atom, an alkyl group, a silyl group, an aryl group, a heteroaryl group, —NY$^{11}$Y$^{12}$, —OY$^{13}$ or —SY$^{14}$ (Y$^{11}$ to Y$^{15}$ each independently represent an alkyl group, an aryl group or a heteroaryl group, and any of these may have further substituents)).

[4] It is preferable in the organic electroluminescent element according to [2] or [3] that the compound represented by the General Formula (2) be a compound represented by following General Formula (3),

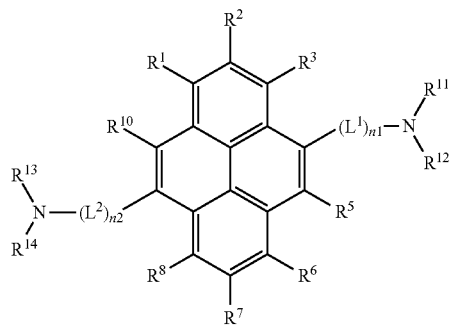

General Formula (3)

(wherein, in General Formula (3), $R^1$ to $R^3$ and $R^6$ to $R^8$ each independently represent a hydrogen atom (including a deuterium atom) or a substituent with a Hammett substituent constant $\sigma_p$ value of −0.15 or more, $R^5$ and $R^{10}$ each independently represent a hydrogen atom or a substituent, $L^1$ and $L^2$ each independently represent a divalent linking group, $R^{11}$ to $R^{14}$ each independently represent an alkyl group, an aryl group or a heteroaryl group, and n1 and n2 each independently represent 1 or 2, however, $R^1$ to $R^3$, $R^5$ to $R^8$, $R^{10}$ to $R^{14}$, $L^1$ and $L^2$ are not bound to each other to form a ring).

[5] It is preferable in the organic electroluminescent element according to any one of [1] to [4] that, in the General Formulae (1) to (3), $L^1$ and $L^2$ each independently represent an arylene group or a heteroarylene group.

[6] It is preferable in the organic electroluminescent element according to [5] that the substituent included in the arylene group or the heteroarylene group each independently represented by $L^1$ and $L^2$ be only a substituent with a Hammett substituent constant $\sigma_p$ value of less than 0.1.

[7] It is preferable in the organic electroluminescent element according to any one of [4] to [6] that the compound represented by the General Formula (3) be a compound represented by any of following General Formulae (4) to (7), General Formula (4)

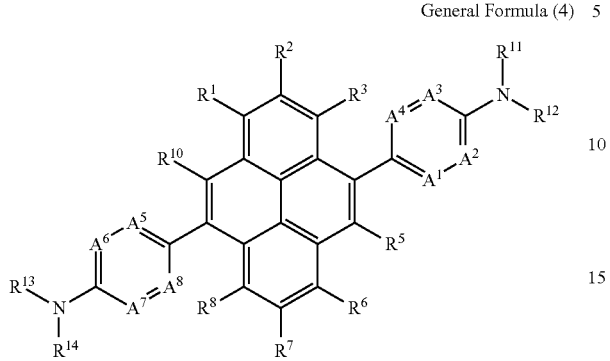

(wherein, in General Formula (4), $R^1$ to $R^3$ and $R^6$ to $R^8$ each independently represent a hydrogen atom (including a deuterium atom) or a substituent with a Hammett substituent constant $\sigma_p$ value of −0.15 or more, $R^5$ and $R^{10}$ each independently represent a hydrogen atom or a substituent, $R^{11}$ to $R^{14}$ each independently represent an alkyl group, an aryl group or a heteroaryl group, $A^1$ to $A^8$ each independently represent CRz (two adjacent CRz's may jointly form a five- or a six-membered ring) or N, and Rz represents a hydrogen atom or a substituent, however, $R^1$ to $R^3$, $R^5$ to $R^8$, $R^{10}$ to $R^{14}$ and $A^1$ to $A^8$ are not bound to each other to form a ring), General Formula (5)

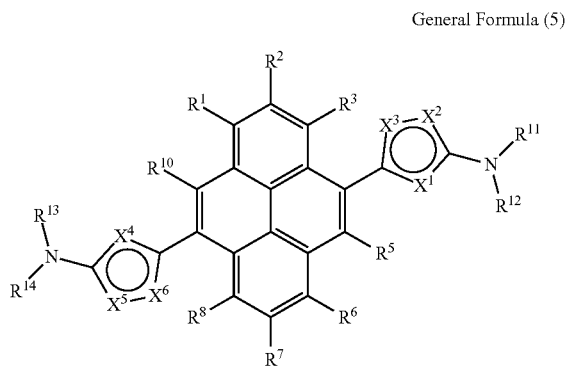

(wherein, in General Formula (5), $R^1$ to $R^3$ and $R^6$ to $R^8$ each independently represent a hydrogen atom (including a deuterium atom) or a substituent with a Hammett substituent constant $\sigma_p$ value of −0.15 or more, $R^5$ and $R^{10}$ each independently represent a hydrogen atom or a substituent, $R^{11}$ to $R^{14}$ each independently represent an alkyl group, an aryl group or a heteroaryl group, $X^1$ to $X^6$ each independently represent CRz (two adjacent CRz's may jointly form a five- or a six-membered ring), —N=, NRy, O or S, and Rz and Ry each independently represent a hydrogen atom or a substituent, however, $R^1$ to $R^3$, $R^5$ to $R^8$, $R^{10}$ to $R^{14}$ and $X^1$ to $X^6$ are not bound to each other to form a ring), General Formula (6)

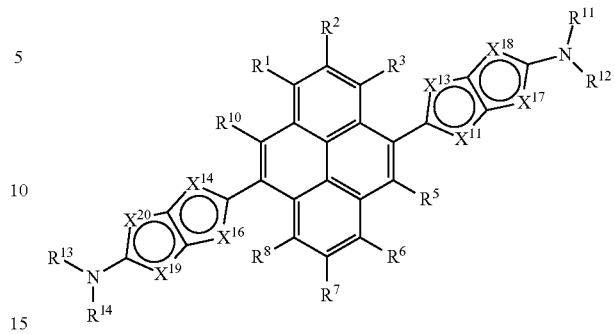

(wherein, in General Formula (6), $R^1$ to $R^3$ and $R^6$ to $R^8$ each independently represent a hydrogen atom (including a deuterium atom) or a substituent with a Hammett substituent constant $\sigma_p$ value of −0.15 or more, $R^5$ and $R^{10}$ each independently represent a hydrogen atom or a substituent, $R^{11}$ to $R^{14}$ each independently represent an alkyl group, an aryl group or a heteroaryl group, $X^{11}$, $X^{13}$, $X^{14}$ and $X^{16}$ to $X^{20}$ each independently represent CRz (two adjacent CRz's may jointly form a five- or a six-membered ring), —N=, NRy, O or S, and Rz and Ry each independently represent a hydrogen atom or a substituent, however, $R^1$ to $R^3$, $R^5$ to $R^8$, $R^{10}$ to $R^{14}$, $X^{11}$, $X^{13}$, $X^{14}$ and $X^{16}$ to $X^{20}$ are not bound to each other to form a ring), General Formula (7)

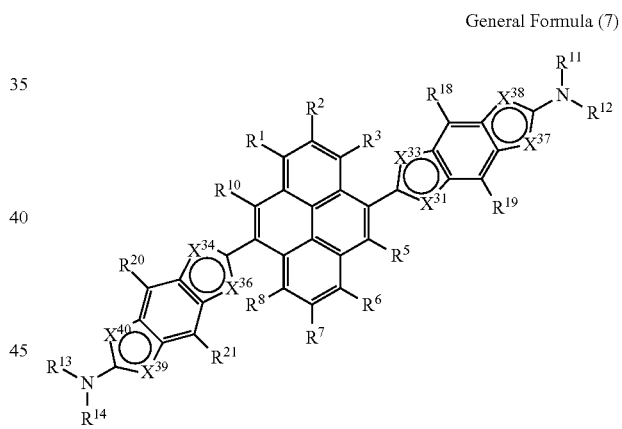

(wherein, in General Formula (7), $R^1$ to $R^3$ and $R^6$ to $R^8$ each independently represent a hydrogen atom (including a deuterium atom) or a substituent with a Hammett substituent constant $_p$ value of −0.15 or more, $R^5$ and $R^{10}$ each independently represent a hydrogen atom or a substituent, $R^{11}$ to $R^{14}$ each independently represent an alkyl group, an aryl group or a heteroaryl group, $R^{18}$ to $R^{21}$ each independently represent a hydrogen atom, a fluorine atom, an alkyl group, a silyl group, an aryl group, a heteroaryl group, —$NY^{21}Y^{22}$, —$OY^{23}$ or —$SY^{24}$ ($Y^{21}$ to $Y^{24}$ each independently represent an alkyl group, an aryl group or a heteroaryl group), and all of these may have further substituents, $X^{31}$, $X^{33}$, $X^{34}$ and $X^{36}$ to $X^{40}$ each independently represent CRz (two adjacent CRz's may jointly form a five- or a six-membered ring), —N=, NRy, O or S, and Rz and Ry each independently represent a hydrogen atom or a substituent, however, $R^1$ to $R^3$, $R^5$ to $R^8$, $R^{10}$ to $R^{14}$, $R^{18}$ to $R^{21}$, $X^{31}$, $X^{33}$, $X^{34}$ and $X^{36}$ to $X^{40}$ are not bound to each other to form a ring).

[8] It is preferable in the organic electroluminescent element according to any one of [1] to [7] that, in the General Formulae (1) to (7), $R^1$ to $R^3$ and $R^6$ to $R^8$ each independently represent a hydrogen atom (including a deuterium atom), an alkyl group, an aryl group, a heteroaryl group, a silyl group, an alkoxy group, an alkylthio group, an aryloxy group, an arylthio group, a halogen atom or a cyano group (these may have further substituents).

[9] It is preferable in the organic electroluminescent element according to any one of [1] to [8] that the light emitting layer include an anthracene-based host material.

[10] It is preferable in the organic electroluminescent element according to any one of [1] to [9] that the light emitting layer be formed by a vacuum deposition process.

[11] It is preferable in the organic electroluminescent element according to any one of [1] to [9] that the light emitting layer be formed by a wet process.

[12] A light emitting device using the organic electroluminescent element according to any one of [1] to [11].

[13] A display device using the organic electroluminescent element according to any one of [1] to [11].

[14] An illumination device using the organic electroluminescent element according to any one of [1] to [11].

[15] A compound represented by following General Formula (1),

General Formula (1)

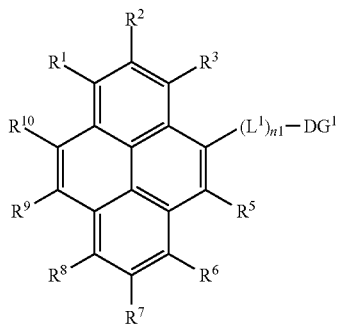

(wherein, in General Formula (1), $R^1$ to $R^3$ and $R^6$ to $R^8$ each independently represent a hydrogen atom (including a deuterium atom) or a substituent with a Hammett substituent constant $\sigma_p$ value of −0.15 or more, $R^5$, $R^9$ and $R^{10}$ each independently represent a hydrogen atom or a substituent, $L^1$ represents a divalent linking group, $DG^1$ represents an electron donating group, and n1 represents 1 or 2, however, $R^1$ to $R^3$, $R^5$ to $R^{10}$, $L^1$, and $DG^1$ are not bound to each other to form a ring).

[16] It is preferable in the compound according to [15] that, in the General Formula (1), $R^1$ to $R^3$ and $R^6$ to $R^8$ each independently represent a hydrogen atom (including a deuterium atom), an alkyl group, an aryl group, a heteroaryl group, a silyl group, an alkoxy group, an alkylthio group, an aryloxy group, an arylthio group, a halogen atom or a cyano group (these may have further substituents).

The organic electroluminescent element of the present invention has sufficient luminous efficiency and excellent chromaticity. The organic electroluminescent element having sufficient luminous efficiency and excellent chromaticity can easily be produced by using compounds of the present invention as light emitting material of a light emitting layer. Another advantage is that the light emitting device, the display device, and the illumination device of the present invention have small power consumption, and excellent chromaticity.

DESCRIPTION OF THE PREFERRED EMBODIMENT

Figure 1:
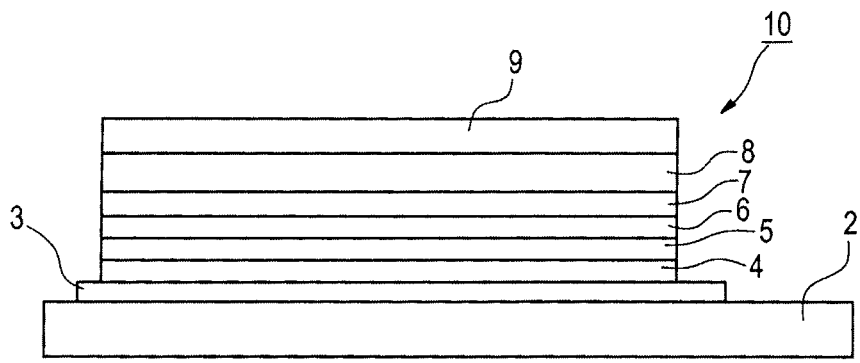
FIG. 1 is a schematic view showing one example of a configuration of an organic electroluminescent element according to the present invention.

Hereinbelow, the details of the present invention will be described. The description of the configuration requirements below is based on representative embodiments and specific examples of the present invention, but the present invention is not limited to these embodiments and specific examples. Incidentally, in the present specification, the range expressed with "to" means a range including the numerical values before and after "to" as the lower limit and the upper limit, respectively.

In the present invention, the hydrogen atom in the description of each general formula also includes isotopes (a deuterium atom and the like), and the atoms constituting the substituent are also intended to include isotopes of the atoms, unless specifically distinguished.

Organic Electroluminescent Element, and Compounds]

The compounds of the present invention are represented by the general formula (1) below.

The organic electroluminescent element of the present invention includes a substrate, a pair of electrodes disposed on the substrate and that includes an anode and a cathode, and an organic layer disposed between the electrodes, wherein the organic layer contains a compound represented by the following general formula (1).

General Formula (1)

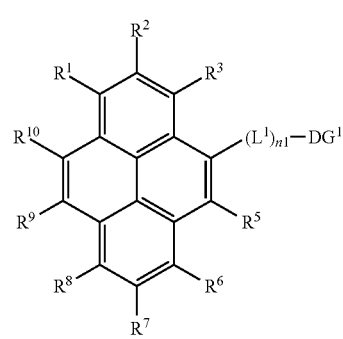

(In the general formula (1), $R^1$ to $R^3$ and $R^6$ to $R^8$ each independently represent a hydrogen atom (including a deuterium atom) or a substituent with a Hammett substituent constant $\sigma_p$ value of −0.15 or more, $R^5$, $R^9$, and $R^{10}$ each independently represent a hydrogen atom or a substituent, $L^1$ represents a divalent linking group, and $DG^1$ represents a donor group. n1 represents 1 or 2. However, $R^1$ to $R^3$, $R^5$ to $R^{10}$, $L^1$, and $DG^1$ are not bound to each other to form a ring.)

The following specifically describes the structures of the compounds of general formula (1) used as light emitting material for the organic electroluminescent element of the present invention, and other configurations of the organic electroluminescent element of the present invention.

Compounds of General Formula (1)

In the present invention, the hydrogen atom in the description of the general formula (1) also includes isotopes (a deuterium atom and the like), and the atoms constituting the substituent are also intended to include isotopes of the atoms.

In the general formula (1), $R^5$, $R^9$, and $R^{10}$ each independently represent a hydrogen atom or a substituent. Examples of the substituents represented by $R^5$, $R^9$, and $R^{10}$ in the general formula (1) include substituents having a second donor group represented by $-(L^2)_{n2}-DG^2$ (where $L^2$ represents a bivalent linking group, $DG^2$ represents a donor group, and n2 represents 1 or 2), and the Substituent Group A below.

Substituent Group A

An alkyl group (preferably having 1 to 30 carbon atoms, more preferably having 1 to 20 carbon atoms, and particularly preferably having 1 to 10 carbon atoms, for example, methyl, ethyl, isopropyl, t-butyl, n-octyl, n-decyl, n-hexadecyl, cyclopropyl, cyclopentyl, and cyclohexyl), an alkenyl group (preferably having 2 to 30 carbon atoms, more preferably 2 to 20 carbon atoms, and particularly preferably 2 to 10 carbon atoms, for example, vinyl, allyl, 2-butenyl and 3-pentenyl), an alkynyl group (preferably having 2 to 30 carbon atoms, more preferably 2 to 20 carbon atoms, and particularly preferably 2 to 10 carbon atoms, for example, propargyl and 3-pentynyl), an aryl group (preferably having 6 to 30 carbon atoms, more preferably having 6 to 20 carbon atoms, and particularly preferably having 6 to 12 carbon atoms, for example, phenyl, p-methylphenyl, naphthyl, and anthranyl), an amino group (preferably has 0 to 30 carbon atoms, more preferably 0 to 20 carbon atoms, and particularly preferably 0 to 10 carbon atoms, for example, amino, methylamino, dimethylamino, diethylamino, dibenzylamino, diphenylamino, and ditolylamino), an alkoxy group (preferably having 1 to 30 carbon atoms, more preferably having 1 to 20 carbon atoms, and particularly preferably having 1 to 10 carbon atoms, for example, methoxy, ethoxy, butoxy, and 2-ethylhexyloxy), an aryloxy group (preferably having 6 to 30 carbon atoms, more preferably having 6 to 20 carbon atoms, and particularly preferably having 6 to 12 carbon atoms, for example, phenyloxy, 1-naphthyloxy and 2-naphthyloxy), a heterocyclic oxy group (preferably having 1 to 30 carbon atoms, more preferably 1 to 20 carbon atoms, and particularly preferably 1 to 12 carbon atoms, for example, pyridyloxy, pyrazyloxy, pyrimidyloxy and quinolyloxy), an acyl group (preferably having 2 to 30 carbon atoms, more preferably 2 to 20 carbon atoms, and particularly preferably 2 to 12 carbon atoms, for example, acetyl, benzoyl, formyl and pivaloyl), an alkoxycarbonyl group (preferably having 2 to 30 carbon atoms, more preferably 2 to 20 carbon atoms, and particularly preferably 2 to 12 carbon atoms, for example, methoxycarbonyl and ethoxycarbonyl), an aryloxycarbonyl group (preferably having 7 to 30 carbon atoms, more preferably 7 to 20 carbon atoms, and particularly preferably 7 to 12 carbon atoms, for example, phenyloxycarbonyl), an acyloxy group (preferably having 2 to 30 carbon atoms, more preferably 2 to 20 carbon atoms, and particularly preferably 2 to 10 carbon atoms, for example, acetoxy and benzoyloxy), an acylamino group (preferably having 2 to 30 carbon atoms, more preferably 2 to 20 carbon atoms, and particularly preferably 2 to 10 carbon atoms, for example, acetylamino and benzoylamino), an alkoxycalbonylamino group (preferably having 2 to 30 carbon atoms, more preferably 2 to 20 carbon atoms, and particularly preferably 2 to 12 carbon atoms, for example, methoxycalbonylamino), an aryloxycarbonylamino group (preferably having 7 to 30 carbon atoms, more preferably 7 to 20 carbon atoms, and particularly preferably 7 to 12 carbon atoms, for example, phenyloxycarbonylamino), a sulfonylamino group (preferably having 1 to 30 carbon atoms, more preferably 1 to 20 carbon atoms, and particularly preferably 1 to 12 carbon atoms, for example, methanesulfonylamino and benzenesulfonylamino), a sulfamoyl group (preferably having 0 to 30 carbon atoms, more preferably 0 to 20 carbon atoms, and particularly preferably 0 to 12 carbon atoms, for example, sulfamoyl, methyl sulfamoyl, dimethyl sulfamoyl and phenyl sulfamoyl), a carbamoyl group (preferably having 1 to 30 carbon atoms, more preferably 1 to 20 carbon atoms, and particularly preferably 1 to 12 carbon atoms, for example, carbamoyl, methyl carbamoyl, diethyl carbamoyl and phenyl carbamoyl), an alkylthio group (preferably having 1 to 30 carbon atoms, more preferably having 1 to 20 carbon atoms, and particularly preferably having 1 to 12 carbon atoms, for example, methylthio and ethylthio), an arylthio group (preferably having 6 to 30 carbon atoms, more preferably having 6 to 20 carbon atoms, and particularly preferably having 6 to 12 carbon atoms, for example, phenylthio), a heterocyclic thio group (preferably having 1 to 30 carbon atoms, more preferably having 1 to 20 carbon atoms, and particularly preferably having 1 to 12 carbon atoms, for example, pyridylthio, 2-benzimizolylthio, 2-benzoxazolylthio, and 2-benzthiazolylthio), a sulfonyl group (preferably having 1 to 30 carbon atoms, more preferably 1 to 20 carbon atoms, and particularly preferably 1 to 12 carbon atoms, for example, mesyl and tosyl), a sulfinyl group (preferably having 1 to 30 carbon atoms, more preferably 1 to 20 carbon atoms, and particularly preferably 1 to 12 carbon atoms, for example, methane sulfinyl and benzene sulfinyl), a ureido group (preferably having 1 to 30 carbon atoms, more preferably 1 to 20 carbon atoms, and particularly preferably 1 to 12 carbon atoms, for example, ureido, methylureido and phenylureido), a phosphoramide group (preferably having 1 to 30 carbon atoms, more preferably 1 to 20 carbon atoms, and particularly preferably 1 to 12 carbon atoms, for example, diethylphosphoramide and phenyl phosphoramide), a hydroxy group, a mercapto group, a fluorine atom, a cyano group, a sulfo group, a carboxyl group, a nitro group, a hydroxamic group, a sulfino group, a hydrazino group, an imino group, a heterocyclic group (including an aromatic heterocyclic group, and preferably having 1 to 30 carbon atoms, and more preferably having 1 to 12 carbon atoms, and examples of the hetero atom include a nitrogen atom, an oxygen atom, a sulfur atom, a phosphorus atom, a silicon atom, a selenium atom, or a tellurium atom, specifically pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, an azepinyl group, and a silolyl group), a silyl group (preferably has 3 to 40 carbon atoms, more preferably 3 to 30, and particularly preferably having 3 to 24 carbon atoms, for example, trimethylsilyl, and triphenylsilyl), a silyloxy group (preferably having 3 to 40 carbon atoms, more preferably 3 to 30 carbon atoms, and particularly preferably 3 to 24 carbon atoms, for example, trimethylsilyloxy and triphenylsilyloxy), a phosphoryl group (for example, diphenylphosphoryl group and dimethylphosphoryl group).

These substituents may be further substituted, and examples of the further substituents include the groups selected from the Substituent Group A as described above. Further, the substituent substituted with the substituent may be further substituted, and examples of the further substituents include the groups selected from the Substituent Group A as described above. Further, the substituent substituted with the substituent that has been substituted with the substituent may be further substituted, and examples of the further substituents include the groups selected from the Substituent Group A as described above.

Preferably, $R^5$, $R^9$, and $R^{10}$ each independently represent a hydrogen atom, an alkyl group, an aryl group, a heteroaryl group, —$NY^1Y^2$, —$OY^3$, —$SY^4$ (where $Y^1$ to $Y^4$ each independently represent an alkyl group, an aryl group, or a heteroaryl group, and these may further have a substituent), a halogen atom, a silyl group, or a substituent that includes a second donor group represented by -$(L^2)_{n2}$-$DG^2$.

More preferably, $R^5$, $R^9$, and $R^{10}$ include at least one -$(L^2)_{n2}$-$DG^2$, even more preferably only one -$(L^2)_{n2}$-$DG^2$. Note that the preferred ranges of $L^2$, n2, and $DG^2$ are the same as the preferred ranges of $L^1$, n1, and $DG^1$, respectively, and will be described later.

The positions of -$(L^2)_{n2}$-$DG^2$ included in $R^5$, $R^9$, and $R^{10}$ are not particularly limited. However, it is preferable that $R^9$ is -$(L^2)_{n2}$-$DG^2$ from the viewpoint of blue color purity (chromaticity) and luminous efficiency.

Specifically, it is particularly preferable that $R^5$ and $R^{10}$ are hydrogen atoms.

In the general formula (1), $R^1$ to $R^3$ and $R^6$ to $R^8$ each independently represent a hydrogen atom (including a deuterium atom) or a substituent having a Hammett substituent constant $\sigma_p$ value of −0.15 or more. Having such substituents are preferable from the viewpoint of improving the blue color purity of the organic electroluminescent element. Note that the emission of the organic electroluminescent element approaches light blue in color when, for example, compounds having a diphenylamino group ($\sigma_p$ value of −0.22) not satisfying the foregoing ranges are used for $R^1$ to $R^3$ and $R^6$ to $R^8$.

The Hammett equation, proposed in 1935 by L. P. Hammett, describes empirical rules to quantitatively discuss the effects of substituents on the reactions or equilibriums of benzene derivatives. The validity of this equation is now widely recognized. The substituent constants required of the Hammett equation include $\sigma_p$ value and $\sigma_m$ value, and these can be found in many books. For example, detailed explanations can be found in books such as *The Hammett Equation, —Structure and Reactivity—*, Naoki Inamoto (Maruzen), *Shin Jikken Kagaku Kouza* 14, *Synthesis and Reaction of Organic Compounds V*, Ed. The Chemical Society of Japan, p. 2605 (Maruzen), *Riron Yuuki Kagaku Kaisetsu*, p. 217, Tadao Nakatani (Tokyo Kagaku Dojin), and *Chemical Review*, Vol. 91, pp. 165 to 195 (1991).

Preferably, $R^1$ to $R^3$ and $R^6$ to $R^8$ each independently represent a hydrogen atom (including a deuterium atom) or a substituent having a Hammett substituent constant $\sigma_p$ value of −0.15 to 0.8, more preferably a hydrogen atom (including a deuterium atom) or a substituent having a Hammett substituent constant $\sigma_p$ value of −0.15 to 0.3.

It is preferable in the organic electroluminescent element of the present invention that, in the general formula (1), $R^1$ to $R^3$ and $R^6$ to $R^8$ each independently represent a hydrogen atom (including a deuterium atom), an alkyl group, an aryl group, a heteroaryl group, a silyl group, an alkoxy group, an alkylthio group, an aryloxy group, an arylthio group, a halogen atom, or a cyano group (these may have further substituents).

From the viewpoint of inhibition of association, $R^1$ to $R^3$ and $R^6$ to $R^8$ preferably each independently represent a hydrogen atom (including a deuterium atom), an alkyl group, an aryl group, a silyl group, or an aryloxy group, particularly preferably a hydrogen atom (including a deuterium atom), or an alkyl group.

The preferred range of each substituent represented by $R^1$ to $R^3$ and $R^6$ to $R^8$ is the same as the preferred range of each substituent in the Substituent Group A.

More preferably, the alkyl groups represented by $R^1$ to $R^3$ and $R^6$ to $R^8$ are each independently a methyl group, an isopropyl group, or a t-butyl group, particularly preferably a t-butyl group from among the preferred range of each substituent in the Substituent Group A.

More preferably, the aryl groups represented by $R^1$ to $R^3$ and $R^6$ to $R^8$ are each independently a phenyl group. The aryl groups represented by $R^1$ to $R^3$ and $R^6$ to $R^8$ may be substituted with substituents such as those in the Substituent Group A, and are preferably substituted. Examples of the aryl groups represented by $R^1$ to $R^3$ and $R^6$ to $R^8$ may be those substituted with an alkyl group, an aryl group, a heteroaryl group, an amino group, a fluorine atom, or a silyl group. Those substituted with an alkyl group are preferred. The alkyl group is preferably a methyl group, an isopropyl group, or a t-butyl group, more preferably a methyl group. When the aryl groups represented by $R^1$ to $R^3$ and $R^6$ to $R^8$ have substituents, the number of substituents is preferably 1 to 3, more preferably 2.

It is particularly preferable that the silyl groups represented by $R^1$ to $R^3$ and $R^6$ to $R^8$ are each independently a trimethylsilyl group from among the preferred range of each substituent in the Substituent Group A.

It is particularly preferable that the aryloxy groups represented by $R^1$ to $R^3$ and $R^6$ to $R^8$ are each independently a phenoxy group from among the preferred range of each substituent in the Substituent Group A.

Preferably, the number of substituents having a Hammett substituent constant $\sigma_p$ value or −0.15 or more in $R^1$ to $R^3$ and $R^6$ to $R^8$ in the general formula (1) is 0 to 4, more preferably 0 to 2, particularly preferably 0 or 2, even more preferably 0.

When $R^1$ to $R^3$ and $R^6$ to $R^8$ in the general formula (1) have substituents having a Hammett substituent constant $\sigma_p$ value of −0.15 or more, the positions of the substituents are not particularly limited. However, it is preferable to have the substituents in at least one of $R^2$ and $R^7$, more preferably in both of $R^2$ and $R^7$ from the viewpoint of inhibition of association, and durability.

In the general formula (1), $L^1$ represents a bivalent linking group. Examples of $L^1$ include an arylene group, a heteroarylene group, an alkenylene group, and an alkynylene group.

In the organic electroluminescent element of the present invention, $L^1$ preferably represents an arylene group or a heteroarylene group, more preferably an arylene group of a 6- to 18-membered ring, or a heteroarylene group of a 5- to 20-membered ring, particularly preferably an arylene group of a 6- to 12-membered ring, or a heteroarylene group of a 5- to 16-membered ring, particularly preferably an arylene group of 6 to 10 carbon atoms, or a heteroarylene group of a 5- to 10-membered ring, even more preferably a phenylene group, or a heteroarylene group of a 6-membered ring.

$L^1$ may be substituted with substituents other than $DG^1$, provided that such substitution does not depart from the gist of the present invention. In this case, the substituents are not particularly limited, and are preferably substituents having a Hammett substituent constant $\sigma_p$ value of less than 0.1, further preferably substituents having a $\sigma_p$ value of −0.6 to 0. Particularly, when $L^1$ represents an arylene group or a heteroarylene group, it is preferable that the only substituents of the arylene group or the heteroarylene group represented by $L^1$ are substituents having a Hammett substituent constant $\sigma_p$ value of less than 0.1.

Preferably, the substituents having a Hammett substituent constant $\sigma_p$ value of less than 0.1 as the substituents of $L^1$ other than $DG^1$ are fluorine atoms ($\sigma_p$ value of 0.06), alkyl groups, silyl groups, aryl groups, heteroaryl groups, —$NY^{31}Y^{32}$, —$OY^{33}$, or —$SY^{34}$ (where $Y^{31}$ to $Y^{34}$ each independently represent an alkyl group, an aryl group, or a heteroaryl group), more preferably alkyl groups, aryl groups, or heteroaryl groups. These may have further substituents. The preferred range of each substituent of $L^1$ other than $DG^1$ is the same as the preferred range of each substituent in the Substituent Group A.

In the present invention, it is preferable that $L^1$ in the general formula (1) does not have substituents other than $DG^1$.

In the general formula (1), n1 represents 1 or 2, and is preferably 1.

In the general formula (1), $DG^1$ represents a donor group.

As used herein, the donor group means an electron donating substituent, and a substituent that shows a negative $\sigma_p$ value in the Hammett equation.

In the organic electroluminescent element of the present invention, the donor group in the general formula (1) is preferably represented by —$NY^1Y^2$, —$OY^3$, or —$SY^4$ (where $Y^1$ to $Y^4$ each independently represent an alkyl group, an aryl group, or a heteroaryl group, and these may have further substituents, and $Y^1$ and $Y^2$ may bind to each other to form a ring), or by the following general formula (A).

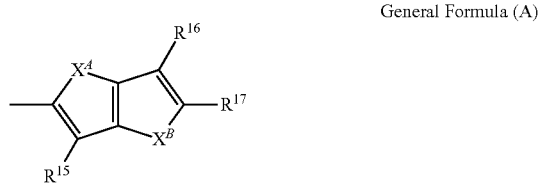

General Formula (A)

In the general formula (A), $X^A$ and $X^B$ each independently represent O, S, or $NY^{15}$, $R^{15}$ to $R^{17}$ each independently represent a hydrogen atom, an alkyl group, a silyl group, an aryl group, a heteroaryl group, —$NY^{11}Y^{12}$, —$OY^{13}$, or —$SY^{14}$ (where $Y^{11}$ to $Y^{15}$ each independently represent an alkyl group, an aryl group, or a heteroaryl group). These may have further substituents.

$X^A$ and $X^B$ each independently represent O, S, or $NY^{15}$, and $Y^{15}$ each independently represent an alkyl group, an aryl group, or a heteroaryl group. These may have further substituents. Examples of the further substituents include those in the Substituent Group A in the case of substituents on carbon atoms, and those in the Substituent Group B below in the case of substituents on nitrogen atoms.

$X^A$ and $X^B$ are preferably 0 or S, more preferably S.

Substituent Group B

An alkyl groups (preferably having 1 to 30 carbon atoms, more preferably having 1 to 20 carbon atoms, and particularly preferably having 1 to 10 carbon atoms, for example, methyl, ethyl, isopropyl, t-butyl, n-octyl, n-decyl, n-hexadecyl, cyclopropyl, cyclopentyl, cyclohexyl), an alkenyl group (preferably having 2 to 30 carbon atoms, more preferably 2 to 20 carbon atoms, and particularly preferably 2 to 10 carbon atoms, for example, vinyl, allyl, 2-butenyl, and 3-pentenyl), an alkynyl group (preferably having 2 to 30 carbon atoms, more preferably 2 to 20 carbon atoms, and particularly preferably 2 to 10 carbon atoms, for example, propargyl and 3-pentynyl), an aryl group (preferably having 6 to 30 carbon atoms, more preferably having 6 to 20 carbon atoms, and particularly preferably having 6 to 12 carbon atoms, for example, phenyl, p-methylphenyl, naphthyl, and anthranyl), a cyano group, and a heterocyclic group (including an aromatic heterocyclic group, and preferably having 1 to 30 carbon atoms, and more preferably having 1 to 12 carbon atoms, and examples of the hetero atom include a nitrogen atom, an oxygen atom, a sulfur atom, a phosphorus atom, a silicon atom, a selenium atom, and a tellurium atom, specifically pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, an azepinyl group, and a silolyl group).

These substituents may be further substituted, and examples of the further substituents include the groups selected from the Substituent Group B as described above. Further, the substituent substituted with the substituent may be further substituted, and examples of the further substituents include the groups selected from the Substituent Group B as described above. Further, the substituent substituted with the substituent that has been substituted with the substituent may be further substituted, and examples of the further substituents include the groups selected from the Substituent Group B as described above.

$R^{15}$ to $R^{18}$ each independently represent a hydrogen atom, an alkyl group, a silyl group, an aryl group, a heteroaryl group, —$NY^{11}Y^{12}$, —$OY^{13}$, or —$SY^{14}$, and $Y^{11}$ to $Y^{14}$ each independently represent an alkyl group, an aryl group, or a heteroaryl group. These may have further substituents. $R^{15}$ to $R^{18}$ are preferably hydrogen atoms, alkyl groups, aryl groups, or —$NY^{11}Y^{12}$, more preferably alkyl groups, or —$NY^{11}Y^{12}$.

Examples of the further substituents include those in the Substituent Group A in the case of substituents on carbon atoms, and those in the Substituent Group B in the case of substituents on nitrogen atoms. Having an alkyl group, a silyl group, an aryl group, or a heteroaryl group is preferred from the viewpoint of inhibition of association.

The donor group in the general formula (1) is preferably —$NY^1Y^2$, —$OY^3$, or a group represented by the general formula (A), more preferably —$NY^1Y^2$. It is further preferable, from the viewpoint of inhibition of association, that the donor group has an alkyl group, a silyl group, an aryl group, or a heteroaryl group.

As mentioned above, $Y^1$ to $Y^4$ in —$NY^1Y^2$, —$OY^3$, and —$SY^4$ each independently represent an alkyl group, an aryl group, or a heteroaryl group, and are preferably aryl groups.

The preferred range of each substituent represented by $Y^1$ to $Y^4$ is the same as the preferred range of each substituent in the Substituent Group A. Of these, $Y^1$ and $Y^2$ in —$NY^1Y^2$ preferably each independently represent a phenyl group, a naphthyl group, or a phenanthryl group, more preferably a phenyl group, or a naphthyl group, particularly preferably a phenyl group, or a 2-naphthyl group.

$Y^1$ and $Y^2$ in $-NY^1Y^2$ further may have a substituent. Example of the further substituents include those in the Substituent Group A in the case of substituents on carbon atoms, and those in the Substituent Group B in the case of substituents on nitrogen atoms. Having a deuterium atom, an alkyl group, a fluorine atom, a silyl group, an aryl group, or a heteroaryl group is preferable from the viewpoint of durability and inhibition of association. It is more preferable to include a deuterium atom, a methyl group, an isopropyl group, a t-butyl group, a fluorine atom, a phenyl group ($-C_6H_5$, $-C_6D_5$), a p-methylphenyl group (tolyl group), a p-isopropylphenyl group, a m-methylphenyl group, an o-methylphenyl group, a trimethylsilyl group, or a cyano group, more preferably a deuterium atom, a methyl group, an isopropyl group, a t-butyl group, a fluorine atom, a phenyl group ($-C_6H_5$, $-C_6D_5$), a p-methylphenyl group (tolyl group), a m-methylphenyl group, or an o-methylphenyl group, particularly preferably a methyl group. When $Y^1$ and $Y^2$ have further substituents, the number of further substituents is preferably 1 to 3, more preferably 1 or 2, particularly preferably 1 for $Y^1$ and $Y^2$.

In the general formula (1), $R^1$ to $R^3$, $R^5$ to $R^{10}$, $L^1$, and $DG^1$ are not bound to each other to form a ring. Specifically, the compounds of the present invention have improved heat resistance, because $L^1$ and $DG^1$ do not bind to any of $R^1$ to $R^3$ and $R^5$ to $R^{10}$ to form a ring.

In the present invention, the compounds represented by the general formula (1) are preferably compounds represented by the following general formula (2).

General Formula (2)

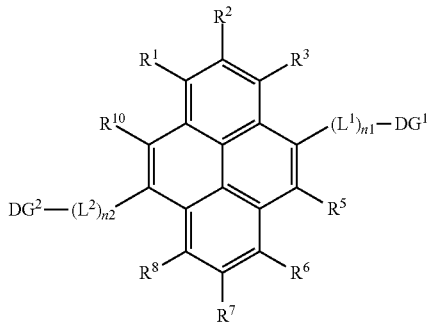

In the general formula (2), $R^1$ to $R^3$ and $R^6$ to $R^8$ each independently represent a hydrogen atom (including a deuterium atom) or a substituent having a Hammett substituent constant $\sigma_p$ value of $-0.15$ or more, $R^5$ and $R^{10}$ each independently represent a hydrogen atom or a substituent, $L^1$ and $L^2$ each independently represent a bivalent linking group, and $DG^1$ and $DG^2$ each independently represent a donor group. n1 and n2 each independently represent 1 or 2. However, $R^1$ to $R^3$, $R^5$ to $R^8$, $R^{10}$, $L^1$, $L^2$, $DG^1$ and $DG^2$ are not bound to each other to form a ring.

The preferred ranges of $R^1$ to $R^3$ and $R^6$ to $R^8$ in the general formula (2) are the same as the preferred ranges of $R^1$ to $R^3$ and $R^6$ to $R^8$ in the general formula (1).

The preferred ranges of $R^5$ and $R^{10}$ in the general formula (2) are the same as the preferred ranges of $R^5$ and $R^{10}$ in the general formula (1).

The preferred ranges of $L^1$ and $L^2$ in the general formula (2) are the same as the preferred ranges of $L^1$ and $L^2$ in the general formula (1).

The preferred ranges of $DG^1$ and $DG^2$ in the general formula (2) are the same as the preferred ranges of $DG^1$ and $DG^2$ in the general formula (1).

The preferred ranges of n1 and n2 in the general formula (2) are the same as the preferred ranges of n1 and n2 in the general formula (1).

In the present invention, the compounds represented by the general formula (2) are preferably compounds represented by the following general formula (3).

General Formula (3)

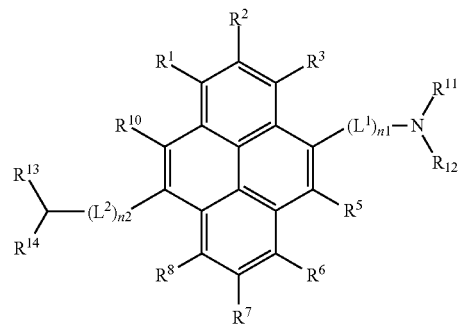

In the general formula (3), $R^1$ to $R^3$ and $R^6$ to $R^8$ each independently represent a hydrogen atom (including a deuterium atom) or a substituent having a Hammett substituent constant $\sigma_p$ value of $-0.15$ or more, $R^5$ and $R^{10}$ each independently represent a hydrogen atom or a substituent, $L^1$ and $L^2$ each independently represent a bivalent linking group, $R^{11}$ to $R^{14}$ each independently represent an alkyl group, an aryl group, or a heteroaryl group. n1 and n2 each independently represent 1 or 2. However, $R^1$ to $R^3$, $R^5$ to $R^8$, $R^{10}$ to $R^{14}$, $L^1$ and $L^2$ are not bound to each other to form a ring.

The preferred ranges of $R^1$ to $R^3$ and $R^6$ to $R^8$ in the general formula (3) are the same as the preferred ranges of $R^1$ to $R^3$ and $R^6$ to $R^8$ in the general formula (1).

The preferred ranges of $R^5$ and $R^{10}$ in the general formula (3) are the same as the preferred ranges of $R^5$ and $R^{10}$ in the general formula (1).

The preferred ranges of $L^1$ and $L^2$ in the general formula (3) are the same as the preferred ranges of $L^1$ and $L^2$ in the general formula (1).

The preferred ranges of n1 and n2 in the general formula (3) are the same as the preferred ranges of n1 and n2 in the general formula (1).

$R^{11}$ to $R^{14}$ in the general formula (3) each independently represent an alkyl group, an aryl group, or a heteroaryl group. The preferred ranges of $R^{11}$ and $R^{12}$ are the same as the preferred ranges of $Y^{11}$ and $Y^{12}$ in the description of $DG^1$ in the general formula (1). The preferred ranges of $R^{13}$ and $R^{14}$ are the same as the preferred ranges of $Y^{11}$ and $Y^{12}$ in the description of $DG^1$ in the general formula (1).

In the present invention, the compounds represented by the general formula (3) are preferably compounds represented by any one of the following general formulae (4) to (7).

General Formula (4)

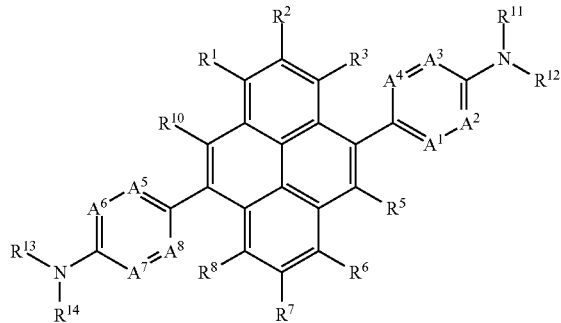

General Formula (5)

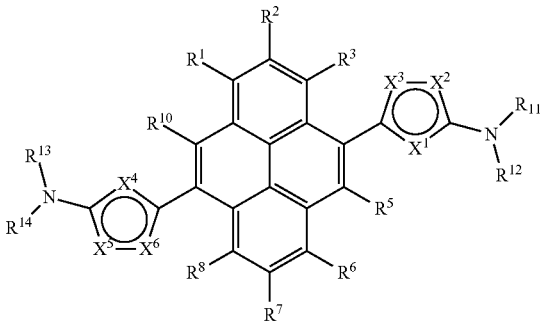

In the general formula (4), $R^1$ to $R^3$ and $R^6$ to $R^8$ each independently represent a hydrogen atom (including a deuterium atom) or a substituent having a Hammett substituent constant $\sigma_p$ value of −0.15 or more, $R^5$ and $R^{10}$ each independently represent a hydrogen atom or a substituent, $R^{11}$ to $R^{14}$ each independently represent an alkyl group, an aryl group, or a heteroaryl group. $A^1$ to $A^8$ each independently represent CRz (two adjacent CRz's may jointly form a five- or six-membered ring) or N, and Rz represents a hydrogen atom or a substituent. However, $R^1$ to $R^3$, $R^5$ to $R^8$, $R^{10}$ to $R^{14}$, and $A^1$ to $A^8$ are not bound to each other to form a ring.

The preferred ranges of $R^1$ to $R^3$ and $R^6$ to $R^8$ in the general formula (4) are the same as the preferred ranges of $R^1$ to $R^3$ and $R^6$ to $R^8$ in the general formula (1).

The preferred ranges of $R^5$ and $R^{10}$ in the general formula (4) are the same as the preferred ranges of $R^5$ and $R^{10}$ in the general formula (1).

$R^{11}$ to $R^{14}$ in the general formula (4) each independently represent an alkyl group, an aryl group, or a heteroaryl group. The preferred ranges of $R^{11}$ and $R^{12}$ are the same as the preferred ranges of $Y^{11}$ and $Y^{12}$ in the description of $DG^1$ in the general formula (1). The preferred ranges of $R^{13}$ and $R^{14}$ are the same as the preferred ranges pf $Y^{11}$ and $Y^{12}$ in the description of $DG^1$ in the general formula (1).

In the general formula (4), $A^1$ to $A^4$ each independently represent CRz (two adjacent CRz's may jointly form a five- or six-membered ring) or N, and Rz represents a hydrogen atom or a substituent. $A^1$ and $A^2$ may be fused to form an aromatic ring. Rz represents a hydrogen atom, an alkyl group, an aryl group, or a heteroaryl group, and these may have further substituents. Rz preferably represents a hydrogen atom, an alkyl group, an aryl group, or a heteroaryl group, and is more preferably a hydrogen atom. $A^1$ to $A^4$ are preferably each independently CH or N. The number of N atoms in $A^1$ to $A^4$ is preferably 0 to 3, more preferably 0 to 2, particularly preferably 0 or 1, even more preferably 0. Examples of the further substituents of $A^1$ to $A^4$ include those in the Substituent Group A in the case of substituents on carbon atoms, and those in the Substituent Group B in the case of substituents on nitrogen atoms.

In the general formula (4), $A^5$ to $A^8$ each independently represent CRz (two adjacent CRz's may jointly form a five- or six-membered ring) or N, and Rz represents a hydrogen atom or a substituent. The relationships and the preferred ranges of $A^5$ to $A^8$ are the same as the relationships and the preferred ranges of $A^1$ to $A^4$.

In the general formula (5), $R^1$ to $R^3$ and $R^6$ to $R^8$ each independently represent a hydrogen atom (including a deuterium atom) or a substituent having a Hammett substituent constant $\sigma_p$ value or −0.15 or more, $R^5$ and $R^{10}$ each independently represent a hydrogen atom or a substituent, $R^{11}$ to $R^{14}$ each independently represent an alkyl group, an aryl group, or a heteroaryl group. $X^1$ to $X^6$ each independently represent CRz (two adjacent CRz's may jointly form a five- or six-membered ring), —N═, NRy, O, or S, and Rz and Ry each independently represent a hydrogen atom or a substituent. However, $R^1$ to $R^3$, $R^5$ to $R^8$, $R^{10}$ to $R^{14}$, and $X^1$ to $X^6$ are not bound to each other to form a ring.

The preferred ranges of $R^1$ to $R^3$ and $R^6$ to $R^8$ in the general formula (5) are the same as the preferred ranges of $R^1$ to $R^3$ and $R^6$ to $R^8$ in the general formula (1).

The preferred ranges of $R^5$ and $R^{10}$ in the general formula (5) are the same as the preferred ranges of $R^5$ and $R^{10}$ in the general formula (1).

$R^{11}$ to $R^{14}$ in the general formula (5) each independently represent an alkyl group, an aryl group, or a heteroaryl group. The preferred ranges of $R^{11}$ and $R^{12}$ are the same as the preferred ranges of $Y^{11}$ and $Y^{12}$ in the description of $DG^1$ in the general formula (1). The preferred ranges of $R^{13}$ and $R^{14}$ are the same as the preferred ranges of $Y^{11}$ and $Y^{12}$ in the description of $DG^1$ in the general formula (1).

In the general formula (5), $X^1$ to $X^6$ each independently represent CRz (two adjacent CRz's may jointly form a five- or six-membered ring), —N═, NRy, O, or S.

Rz and Ry each independently represent a hydrogen atom or a substituent. Examples of the substituent Rz on carbon atoms include substituents in the Substituent Group A. Examples of the substituent Ry on nitrogen atoms include substituents in the Substituent Group B. The preferred range of Rz in the general formula (5) is the same as the preferred range of Rz in the general formula (4). The preferred range of Ry in the general formula (5) includes a hydrogen atom, or is the same as the preferred range of the Substituent Group B.

$X^1$ to $X^3$ mean linking groups forming the aromatic ring. For example, $X^1$ to $X^3$ are preferably represented by two atom linking groups each having three bonds, and a single atom linking group having two bonds in a resonance structure. Here, the two atom linking groups having three bonds in $X^1$ to $X^3$ are CRz or —N═, and the single atom linking group having two bonds in $X^1$ to $X^3$ is NRy, O, or S. The two atom linking groups having three bonds in $X^1$ to $X^3$ are preferably CH, CAr (Ar is an aryl group), or N, more preferably CH or N, particularly preferably CH. The single atom linking group having two bonds in $X^1$ to $X^3$ is preferably NR (R is an alkyl group), NAr (Ar is an aryl group), O, or S, more preferably O or S, particularly preferably O. Note that the position of the atom linking group having two bonds in $X^1$ to $X^3$ in a resonance structure is not particularly limited, and is preferably at $X^1$.

The relationships and the preferred ranges of $X^4$ to $X^5$ are the same as the relationships and the preferred ranges of $X^1$ to $X^3$. Note that the position of the atom linking group having two bonds in $X^4$ to $X^6$ in a resonance structure is not particularly limited, and is preferably at $X^4$.

General Formula (6)

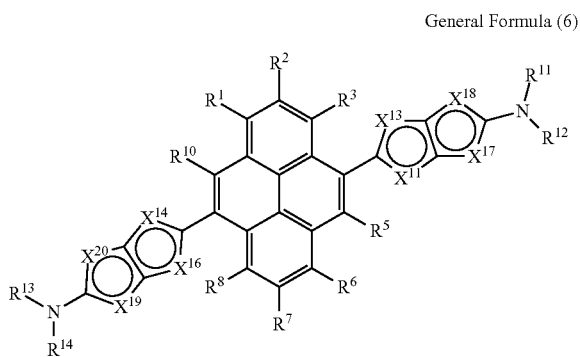

In the general formula (6), $R^1$ to $R^3$ and $R^6$ to $R^8$ each independently represent a hydrogen atom (including a deuterium atom) or a substituent having a Hammett substituent constant $\sigma_p$ value of −0.15 or more, $R^5$ and $R^{10}$ each independently represent a hydrogen atom or a substituent, $R^{11}$ to $R^{14}$ each independently represent an alkyl group, an aryl group, or a heteroaryl group. $X^{11}$, $X^{13}$, $X^{14}$, and $X^{16}$ to $X^{20}$ each independently represent CRz (two adjacent CRz's may jointly form a five- or six-membered ring), —N=, NRy, O, or S, Rz and Ry each independently represent a hydrogen atom or a substituent. However, $R^1$ to $R^3$, $R^5$ to $R^8$, $R^{10}$ to $R^{14}$, $X^{11}$, $X^{13}$, $X^{14}$, and $X^{16}$ to $X^{20}$ are not bound to each other to form a ring.

The preferred ranges of $R^1$ to $R^3$ and $R^6$ to $R^8$ in the general formula (6) are the same as the preferred ranges of $R^1$ to $R^3$ and $R^6$ to $R^8$ in the general formula (1).

The preferred ranges of $R^5$ and $R^{10}$ in the general formula (6) are the same as the preferred ranges of $R^5$ and $R^{10}$ in the general formula (1).

$R^{11}$ to $R^{14}$ in the general formula (6) each independently represent an alkyl group, an aryl group, or a heteroaryl group. The preferred ranges of $R^{11}$ and $R^{12}$ are the same as the preferred ranges of $Y^{11}$ and $Y^{12}$ in the description of $DG^1$ in the general formula (1). The preferred ranges of $R^{13}$ and $R^{14}$ are the same as the preferred ranges of $Y^{11}$ and $Y^{12}$ in the description of $DG^1$ in the general formula (1).

In the general formula (6), $X^{11}$, $X^{13}$, $X^{14}$, and $X^{16}$ to $X^{20}$ each independently represent CRz (two adjacent CRz's may jointly form a five- or six-membered ring), —N=, NRy, O, or S.

Rz and Ry each independently represent a hydrogen atom or a substituent. Examples of the substituent Rz on carbon atoms include substituents in the Substituent Group A. Examples of the substituent Ry on nitrogen atoms include substituents in the Substituent Group B. The preferred range of Rz in the general formula (6) is the same as the preferred range of Rz in the general formula (4). The preferred range of Ry in the general formula (6) includes a hydrogen atom, or is the same as the preferred range of the Substituent Group B.

$X^{11}$ and $X^{13}$ means linking groups forming the aromatic ring. For example, $X^{11}$ and $X^{13}$ are preferably represented by a single atom linking group having three bonds, and a single atom linking group having two bonds in a resonance structure. Here, the single atom linking group having three bonds in $X^{11}$ and $X^{13}$ are CRz or —N=, and the single atom linking group having two bonds in $X^{11}$ and $X^{13}$ is NRy, O, or S. The single atom linking group having three bonds in $X^{11}$ and $X^{13}$ are preferably CH, CAr (Ar is an aryl group), or N, more preferably CH or N, particularly preferably CH. The single atom linking group having two bonds in $X^{11}$ and $X^{13}$ is preferably O or S, more preferably S. Note that the position of the atom linking group having two bonds in $X^{11}$ and $X^{13}$ in a resonance structure is not particularly limited, and is preferably at $X^{11}$.

The relationship and the preferred ranges of $X^{18}$ and $X^{17}$ are the same as the relationship and the preferred ranges of $X^{11}$ and $X^{13}$. Note that the position of the atom linking group having two bonds in $X^{18}$ and $X^{17}$ in a resonance structure is not particularly limited, and is preferably at $X^{18}$.

The relationship and the preferred ranges of $X^{14}$ and $X^{16}$ are the same as the relationship and the preferred ranges of $X^{11}$ and $X^{13}$. Note that the position of the atom linking group having two bonds in $X^{14}$ and $X^{16}$ in a resonance structure is not particularly limited, and is preferably at $X^{14}$.

The relationship and the preferred ranges of $X^{19}$ and $X^{20}$ are the same as the relationship and the preferred ranges of $X^{11}$ and $X^{13}$. Note that the position of the atom linking group having two bonds in $X^{19}$ and $X^{20}$ in a resonance structure is not particularly limited, and is preferably at $X^{19}$.

General Formula (7)

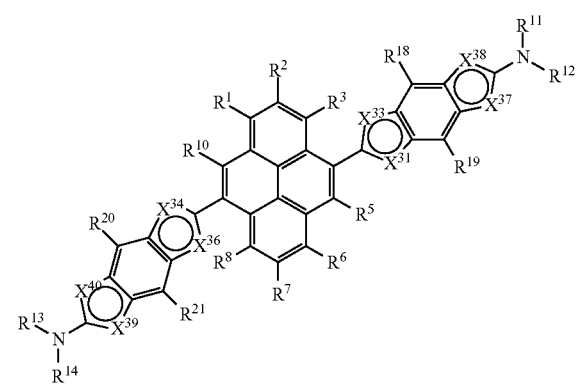

In the general formula (7), $R^1$ to $R^3$ and $R^6$ to $R^8$ each independently represent a hydrogen atom (including a deuterium atom), or a substituent having a Hammett substituent constant p value of −0.15 or more, $R^5$ and $R^{10}$ each independently represent a hydrogen atom or a substituent, $R^{11}$ to $R^{14}$ each independently represent an alkyl group, an aryl group, or a heteroaryl group. $R^{18}$ to $R^{21}$ each independently represent a hydrogen atom, a fluorine atom, an alkyl group, a silyl group, an aryl group, a heteroaryl group, —$NY^{21}Y^{22}$, —$OY^{23}$, or —$SY^{24}$ (where $Y^{21}$ to $Y^{24}$ each independently represent an alkyl group, an aryl group, or a heteroaryl group). These may have further substituents. $X^{31}$, $X^{33}$, $X^{34}$, and $X^{36}$ to $X^{40}$ each independently represent CRz (two adjacent CRz's may jointly form a five- or six-membered ring), —N=, NRy, O, or S, Rz and Ry each independently represent a hydrogen atom or a substituent. However, $R^1$ to $R^3$, $R^5$ to $R^8$, $R^{10}$ to $R^{14}$, $R^{18}$ to $R^{21}$, $X^{31}$, $X^{33}$, $X^{34}$, and $X^{36}$ to $X^{40}$ are not bound to each other to form a ring.

The preferred ranges of $R^1$ to $R^3$ and $R^6$ to $R^8$ in the general formula (7) are the same as the preferred ranges of $R^1$ to $R^3$ and $R^6$ to $R^8$ in the general formula (1).

The preferred ranges of $R^5$ and $R^{10}$ in the general formula (7) are the same as the preferred ranges of $R^5$ and $R^{10}$ in the general formula (1).

$R^{11}$ to $R^{14}$ in the general formula (7) each independently represent an alkyl group, an aryl group, or a heteroaryl group. The preferred ranges of $R^{11}$ and $R^{12}$ are the same as the preferred ranges of $Y^{11}$ and $Y^{12}$ in the description of $DG^1$ in the general formula (1). The preferred ranges of $R^{13}$ and $R^{14}$ are the same as the preferred ranges of $Y^{11}$ and $Y^{12}$ in the description of $DG^1$ in the general formula (1).

In the general formula (7), $X^{31}$, $X^{33}$, $X^{34}$, and $X^{36}$ to $X^{40}$ each independently represent CRz (two adjacent CRz's may jointly form a five- or six-membered ring), —N=, NRy, O, or S.

Rz and Ry each independently represent a hydrogen atom or a substituent. Examples of the substituent Rz on carbon atoms include substituents in the Substituent Group A. Examples of the substituent Ry on nitrogen atoms include substituents in the Substituent Group B. The preferred range of Rz in the general formula (7) is the same as the preferred range of Rz in the general formula (4). The preferred range of Ry in the general formula (7) includes a hydrogen atom, or is the same as the preferred range of the Substituent Group B.

$X^{31}$ and $X^{33}$ means linking groups forming the aromatic ring. For example, $X^{31}$ and $X^{33}$ are preferably represented by a single atom linking group having three bonds, and a single atom linking group having two bonds in a resonance structure. Here, the single atom linking group having three bonds in $X^{31}$ and $X^{33}$ are CRz or —N=, and the single atom linking group having two bonds in $X^{31}$ and $X^{33}$ is NRy, O, or S. The single atom linking group having three bonds in $X^{31}$ and $X^{33}$ are preferably CH, CAr (Ar is an aryl group), or N, more preferably CH or N, particularly preferably CH. The single atom linking group having two bonds in $X^{31}$ and $X^{33}$ is preferably O or S, more preferably S. Note that the position of the atom linking group having two bonds in $X^{31}$ and $X^{33}$ in a resonance structure is not particularly limited, and is preferably at $X^{31}$.

The relationship and the preferred ranges of $X^{38}$ and $X^{37}$ are the same as the relationship and the preferred ranges of $X^{31}$ and $X^{33}$. Note that the position of the atom linking group having two bonds in $X^{38}$ and $X^{37}$ in a resonance structure is not particularly limited, and is preferably at $X^{38}$.

The relationship and the preferred ranges of $X^{34}$ and $X^{36}$ are the same as the relationship and the preferred ranges of $X^{31}$ and $X^{33}$. Note that the position of the atom linking group having two bonds in $X^{34}$ and $X^{36}$ in a resonance structure is not particularly limited, and is preferably at $X^{34}$.

The relationship and the preferred ranges of $X^{39}$ and $X^{40}$ are the same as the relationship and the preferred ranges of $X^{31}$ and $X^{33}$. Note that the position of the atom linking group having two bonds in $X^{39}$ and $X^{40}$ in a resonance structure is not particularly limited, and is preferably at $X^{39}$.

$R^{18}$ and $R^{19}$ each independently represent a hydrogen atom, a fluorine atom, an alkyl group, a silyl group, an aryl group, a heteroaryl group, —$NY^{21}Y^{22}$, —$OY^{23}$, —$SY^{24}$ (where $Y^{21}$ to $Y^{24}$ each independently represent an alkyl group, an aryl group, or a heteroaryl group). These may have further substituents. $R^{18}$ and $R^{19}$ each independently represent preferably a hydrogen atom, a fluorine atom, an alkyl group, an aryl group, or —$NY^{21}Y^{22}$, more preferably a hydrogen atom, a fluorine atom, an alkyl group, or an aryl group. The preferred range of each substituent represented by $Y^{21}$ to $Y^{24}$ is the same as the preferred range of each substituent in the Substituent Group A.

Examples of the further substituents of $R^{18}$ and $R^{19}$ include those in the Substituent Group A in the case of the substituents on carbon atoms, and those in the Substituent Group B in the case of the substituents on nitrogen atoms. However, $R^{18}$ and $R^{19}$ are preferably substituents having a Hammett substituent constant $\sigma_p$ value of 0.1 or less, and more preferably include a substituent having a $\sigma_p$ value of −0.5 to 0.1.

The preferred ranges of $R^{20}$ and $R^{21}$ are the same as the preferred ranges of $R^{18}$ and $R^{19}$.

The compounds represented by the general formula (1) are preferably linking groups represented by the general formula (4) or (5) from among the compounds represented by the general formulae (4) to (7) from the viewpoint of sufficiently obtaining the effect of the donor group connected to the pyrene skeleton via $L^1$ (or $L^2$), more preferably linking groups represented by the general formula (4).

The maximum luminous wavelength of the organic electroluminescent element using the compounds represented by the general formula (1) typically ranges from 400 nm to 480 nm, preferably 420 nm to 470 nm, further preferably 430 nm to 460 nm. In the present invention, it is preferable to use particularly the compounds represented by the general formulae (4) to (7) as the compounds represented by the general formula (1), because it makes the maximum luminous wavelength of the organic electroluminescent element from about 430 nm to 460 nm, and provides blue emission of particularly high color purity. The maximum luminous wavelength of the organic electroluminescent element using the compounds represented by the general formula (1) is most preferably 440 nm or more and less than 455 nm from the viewpoint of obtaining blue emission having high color purity.

The compound represented by the general formula (1) preferably has a molecular weight of 1,000 or less, more preferably 900 or less, even more preferably 850 or less. By lowering the molecular weight, the sublimation temperature can be lowered, and therefore, the thermal decomposition of the compound at a time of deposition can be prevented. Further, by shortening the deposition time, energy required for deposition can be suppressed.

Specific examples of the compounds represented by the general formula (1) are shown below. However, the compounds of the general formula (1) that can be used in the present invention should not be construed to be limited to the specific examples.

Compound 1
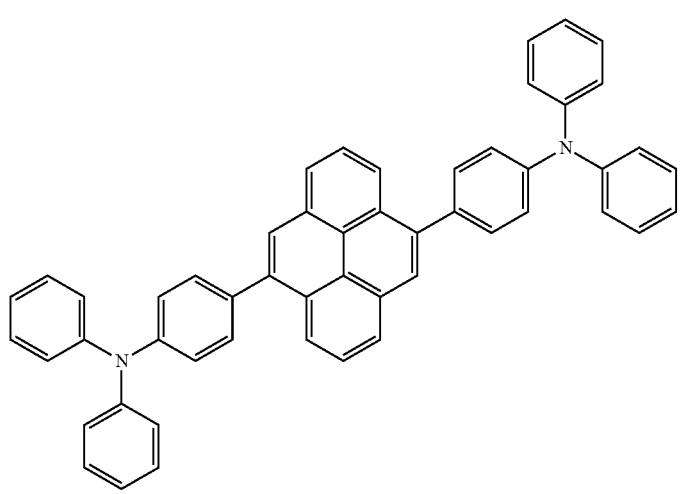
Compound 2
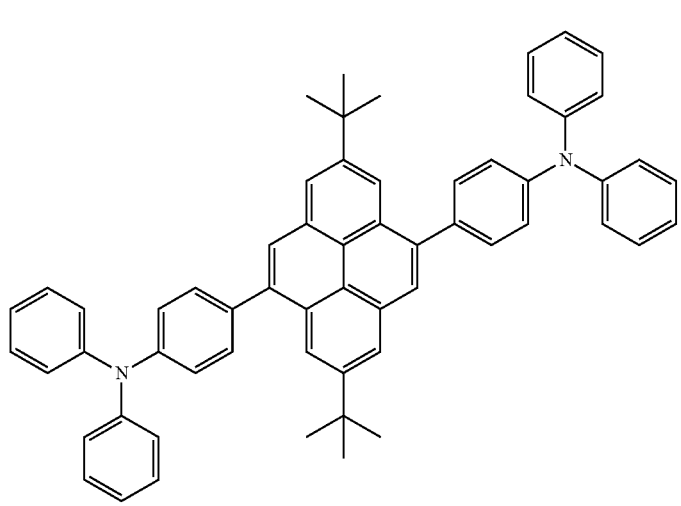
Compound 3
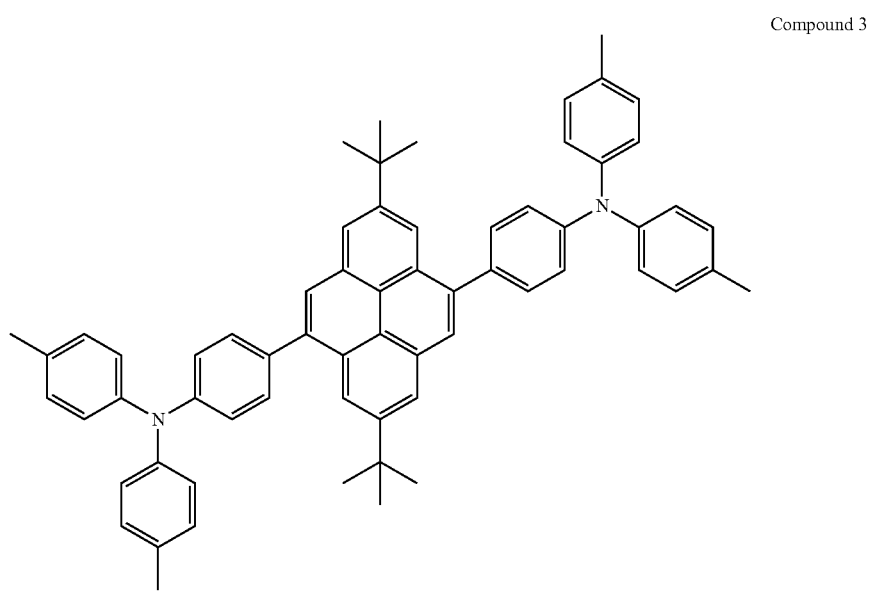

Compound 4
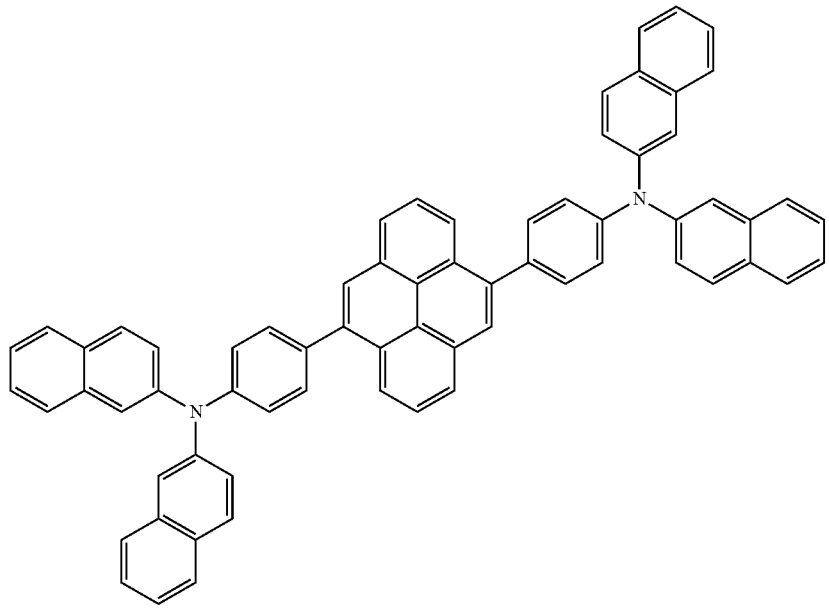
Compound 5
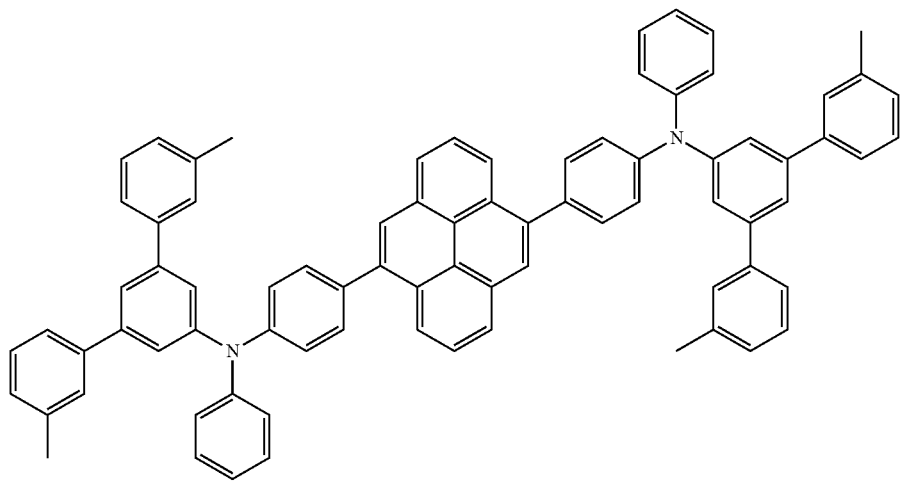
Compound 6
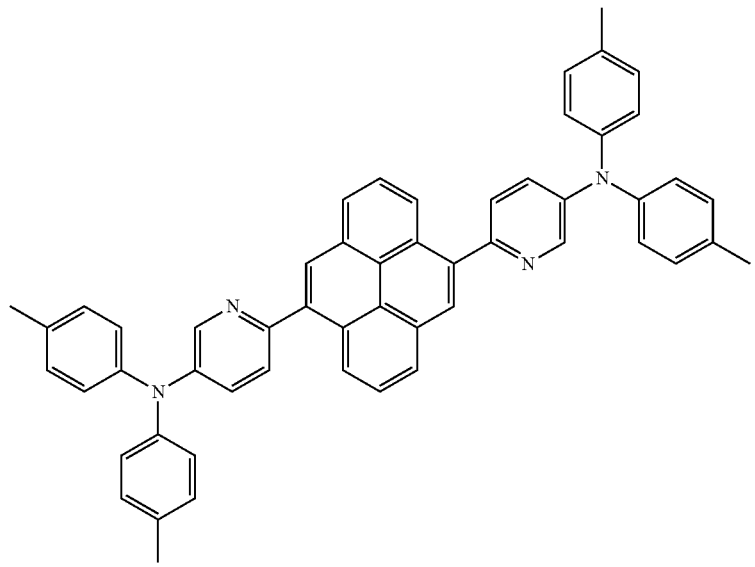

Compound 7
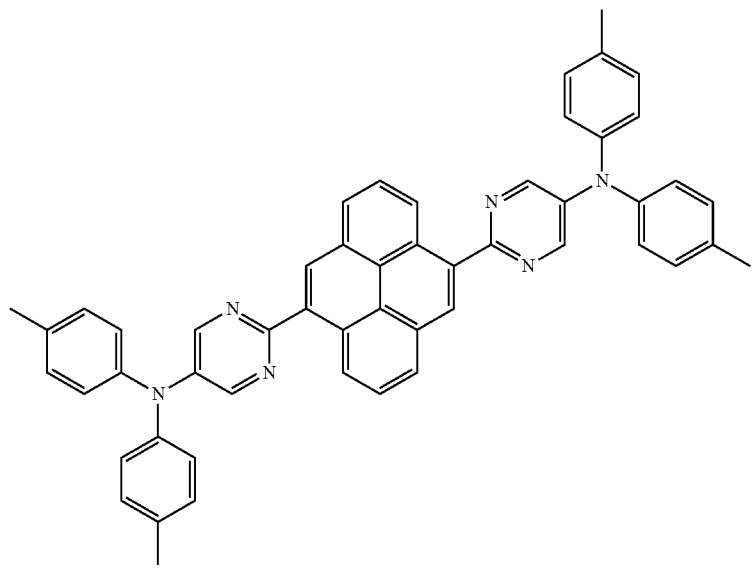
Compound 8
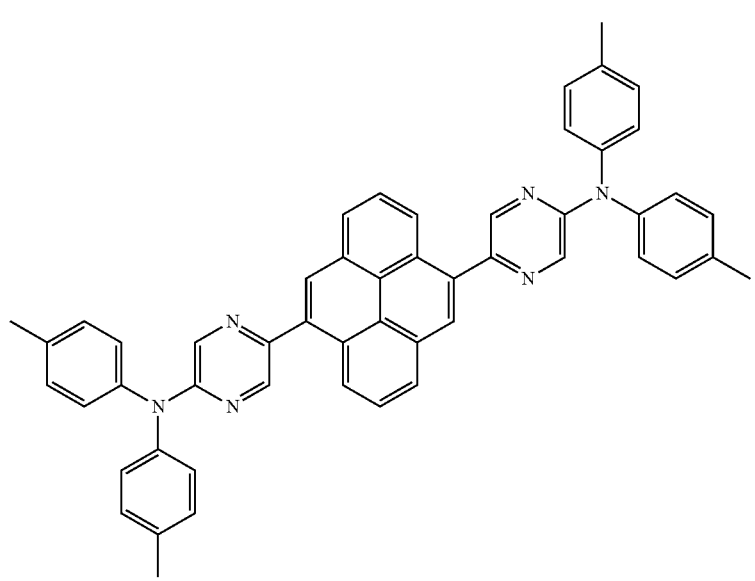

-continued
Compound 9
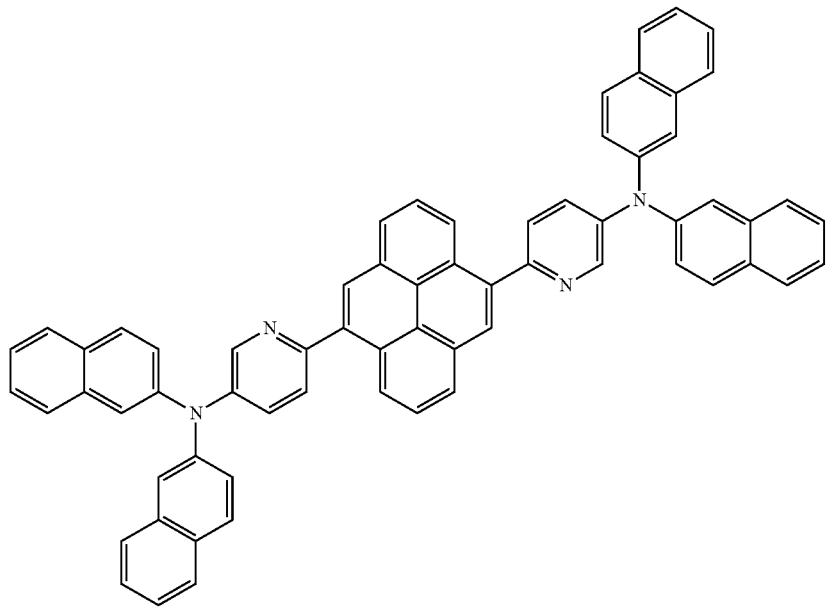
Compound 10
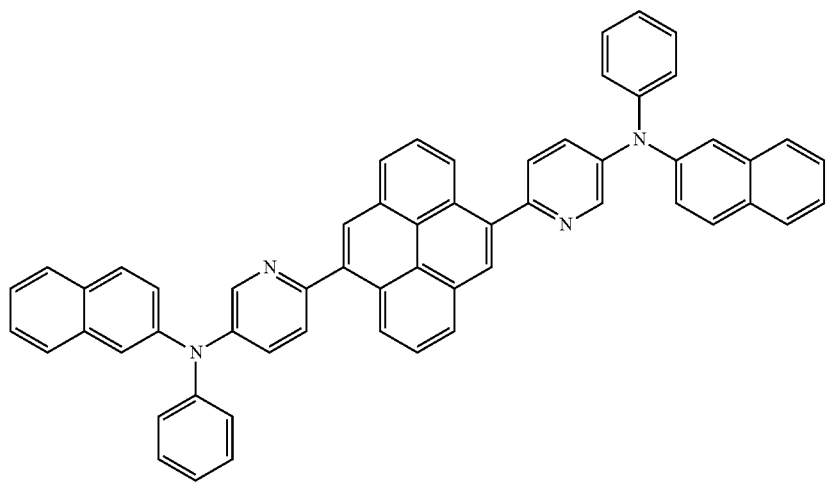
Compound 11
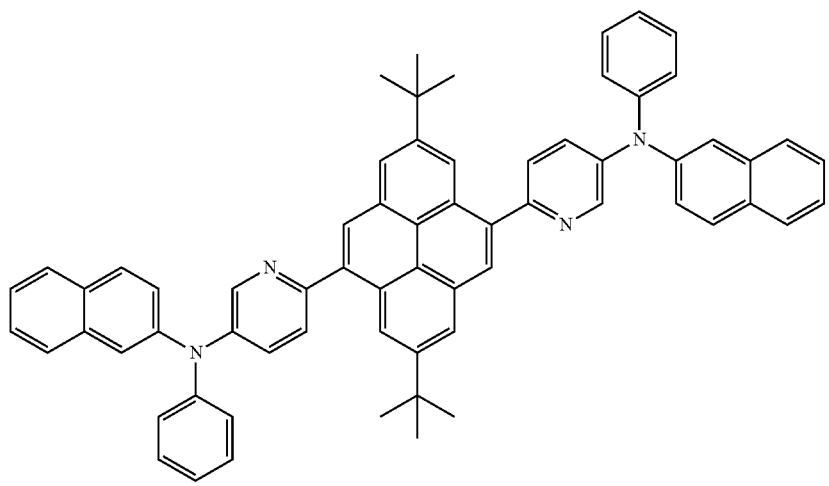

Compound 12
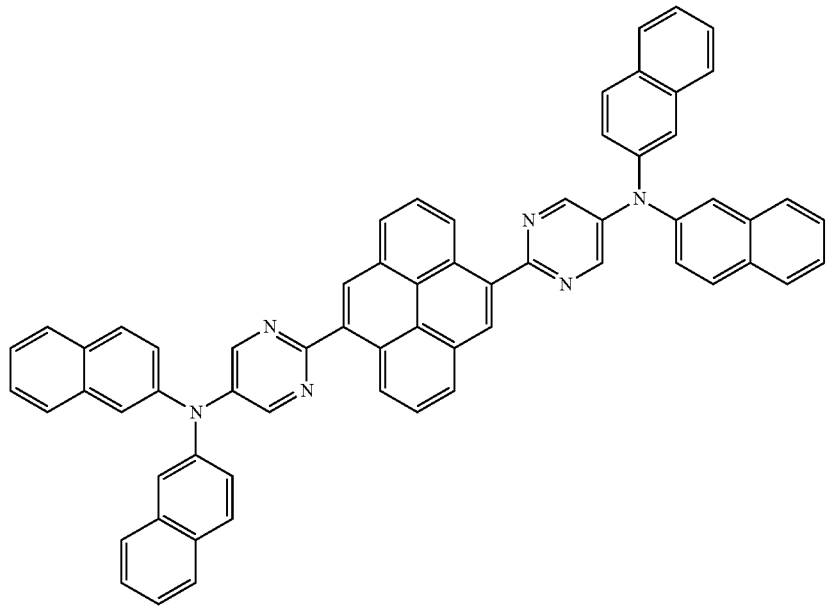
Compound 13
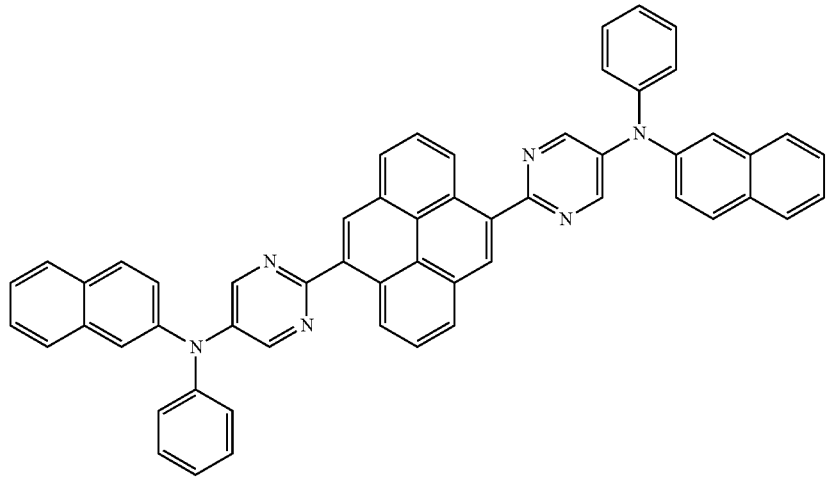
Compound 14
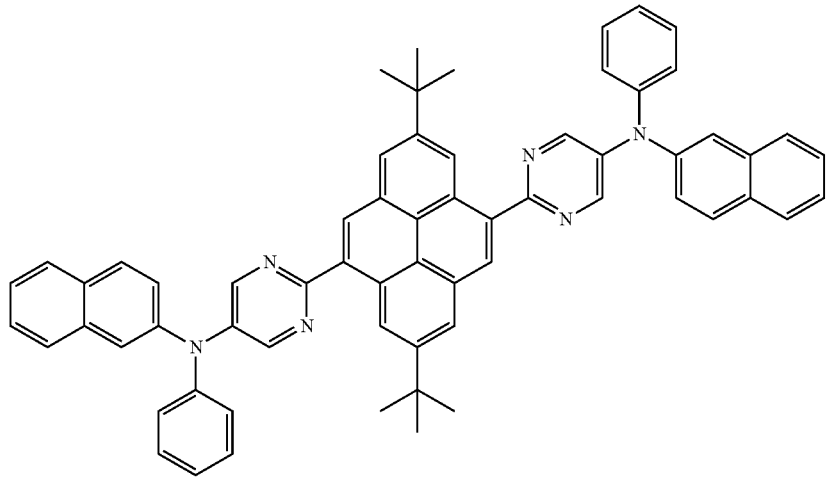

-continued
Compound 15
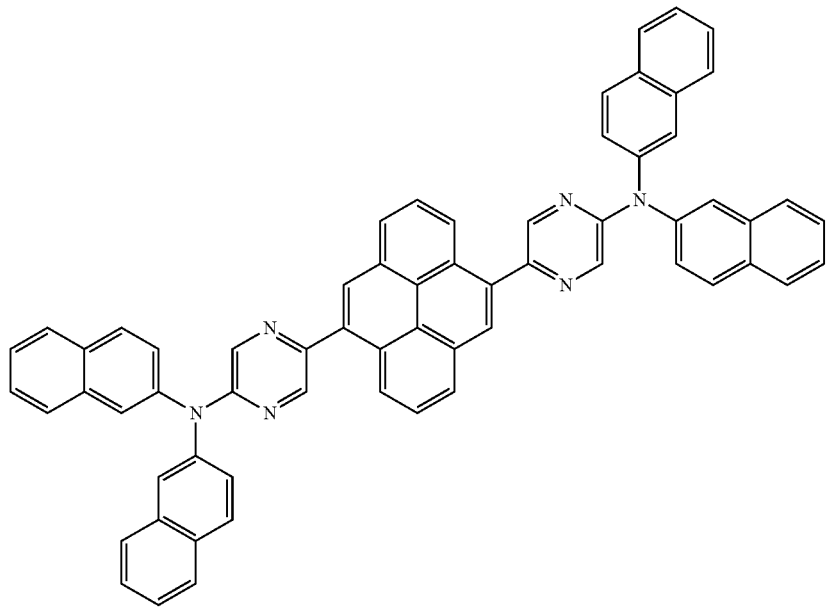
Compound 16
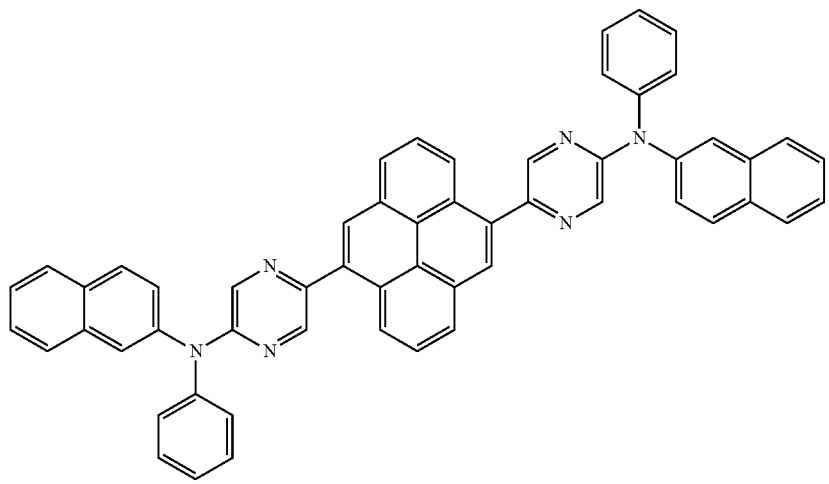
Compound 17
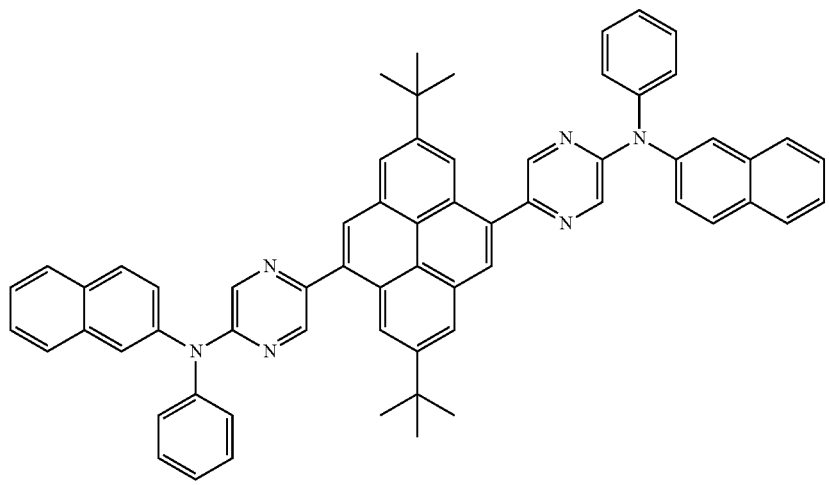

Compound 18
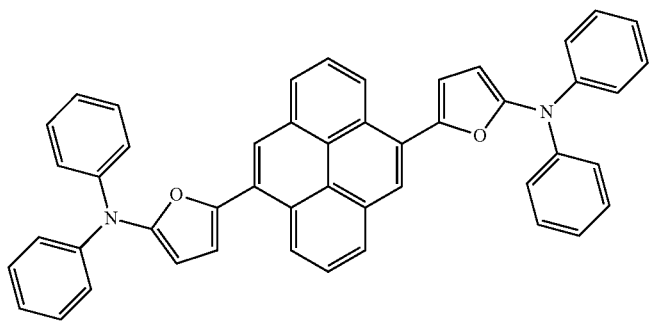
Compound 19
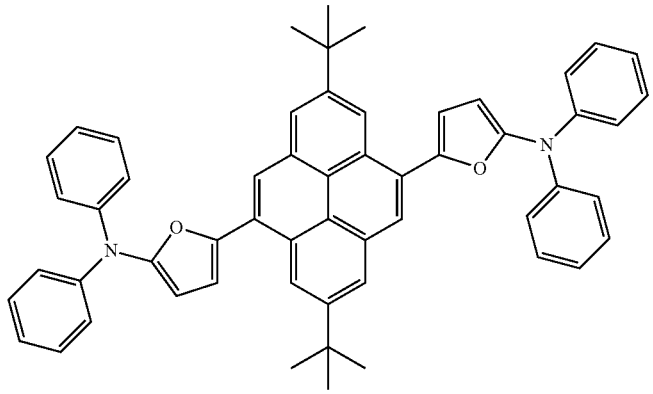
Compound 20
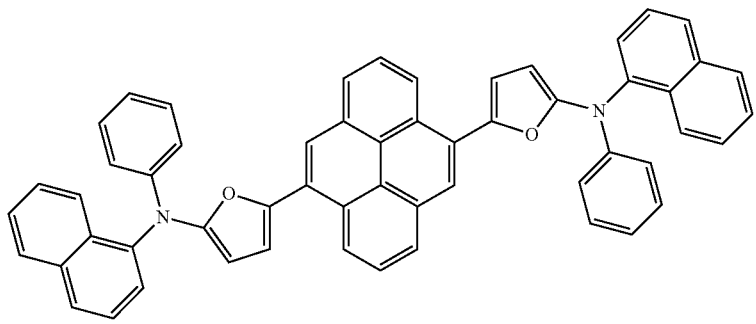
Compound 21
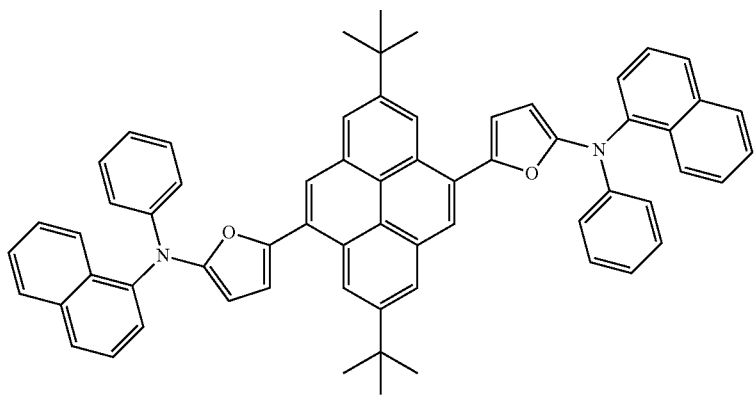

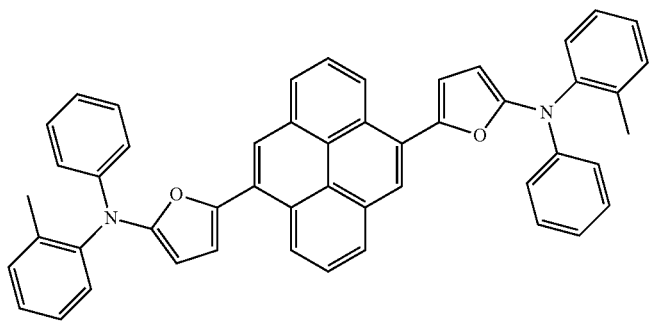
Compound 22
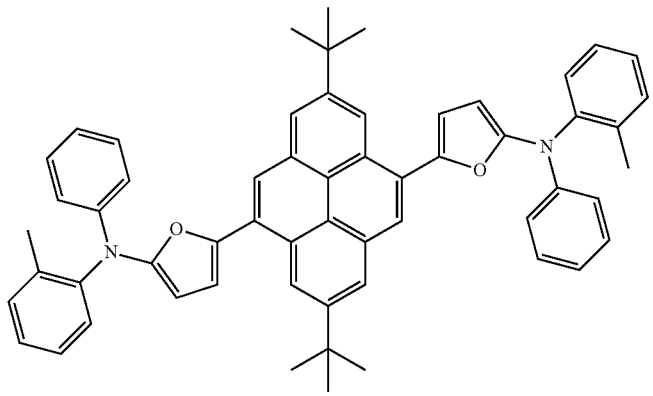
Compound 23
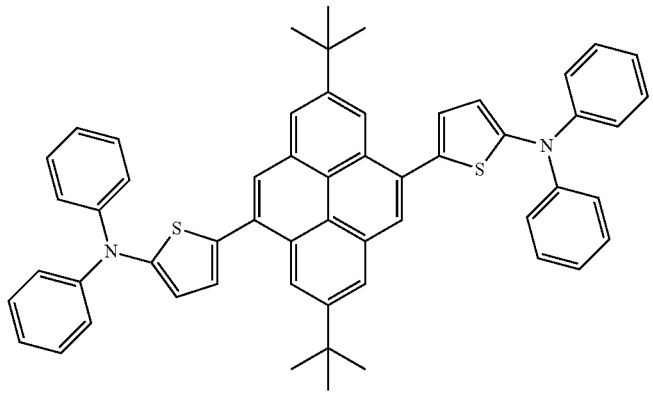
Compound 24
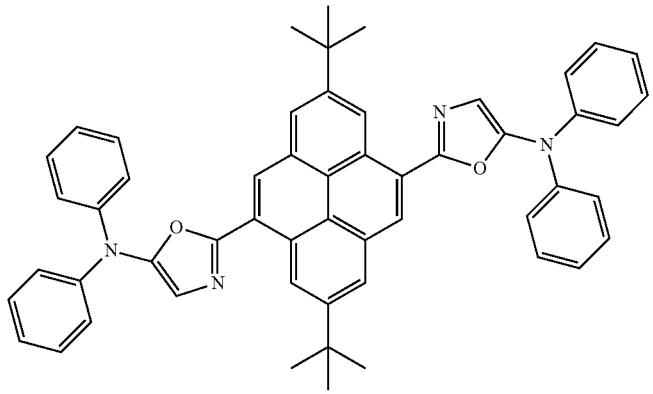
Compound 25

Compound 26
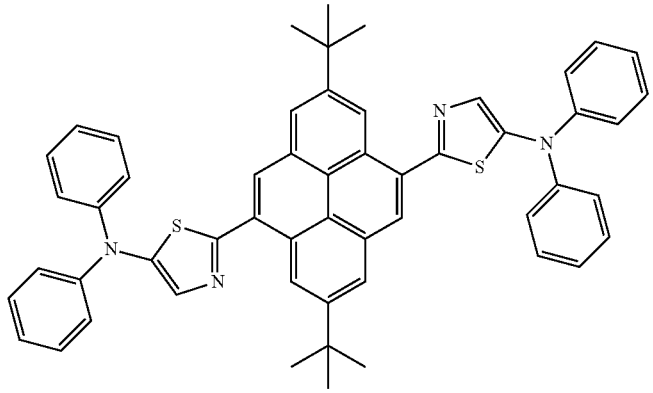
Compound 27
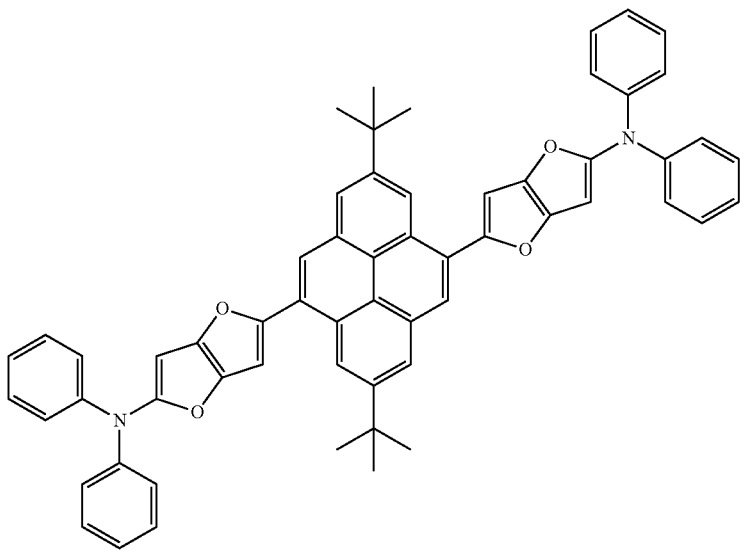
Compound 28
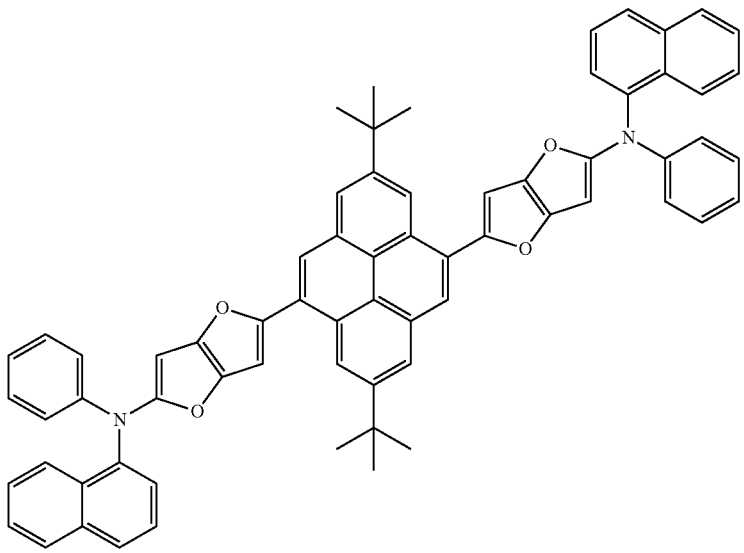

Compound 29
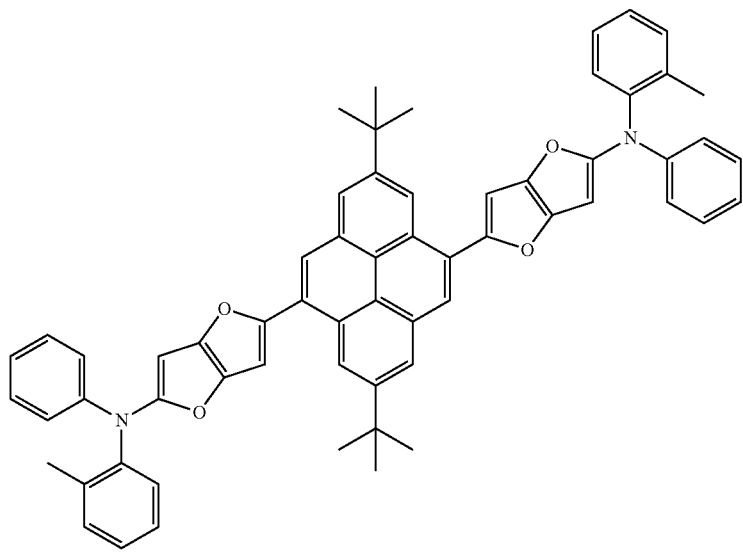
Compound 30
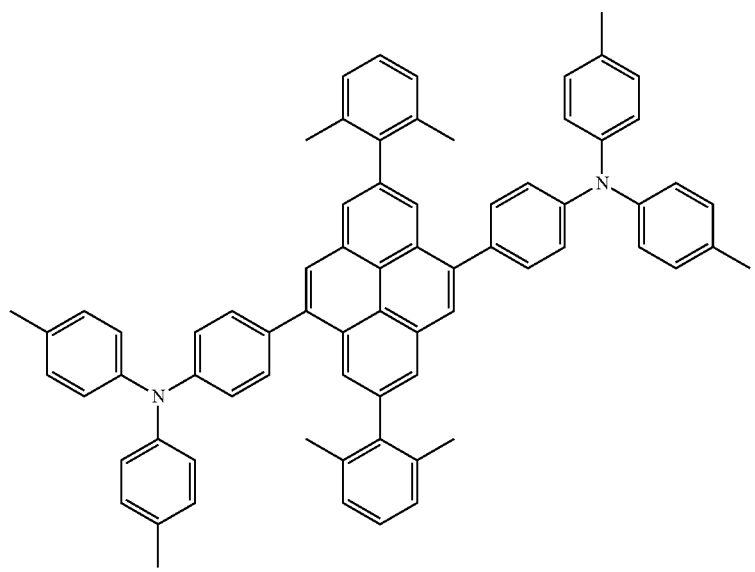
Compound 31
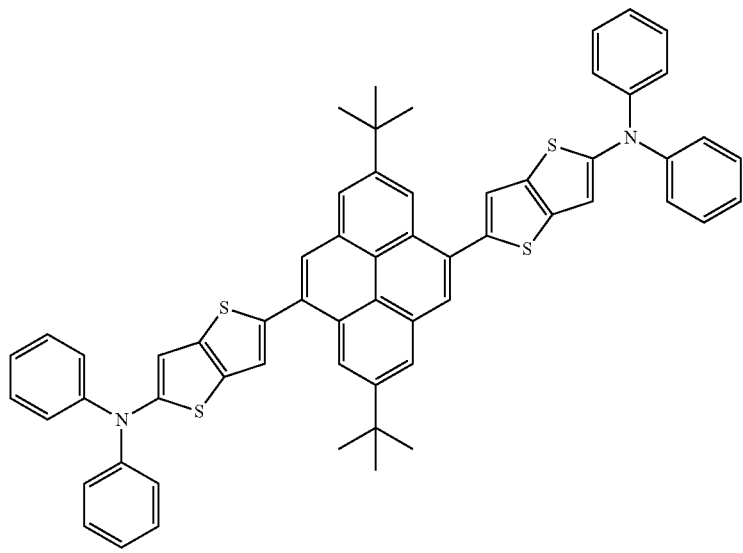

Compound 32
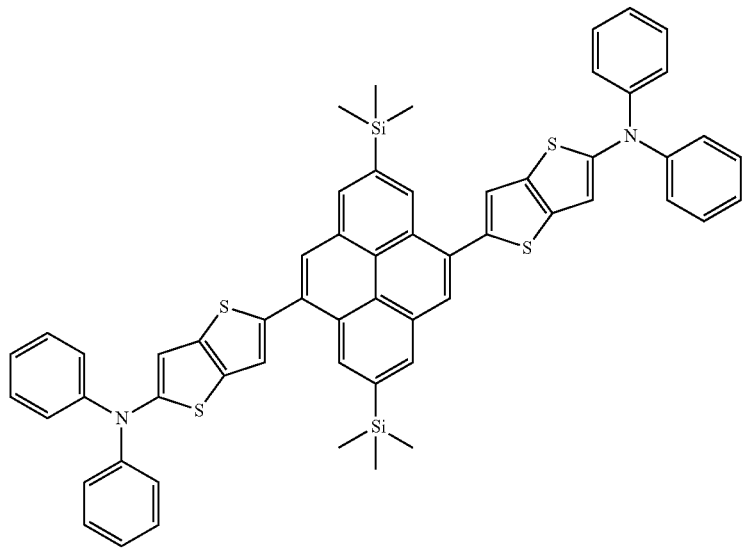
Compound 33
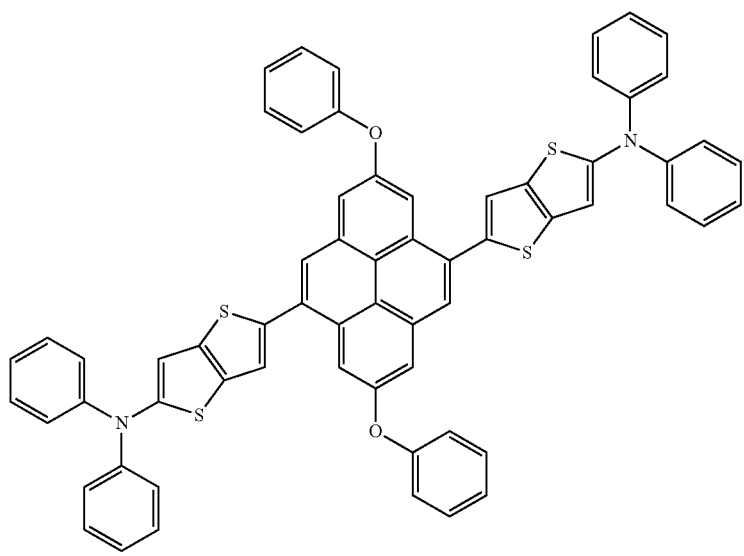
Compound 34
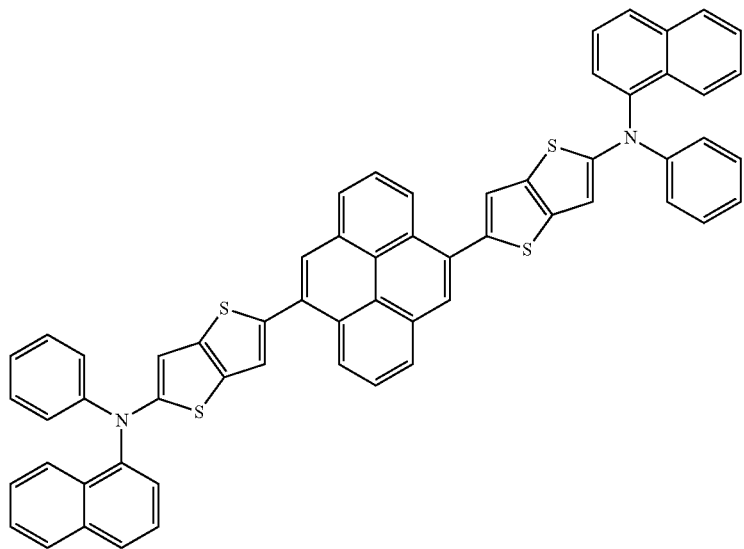

Compound 35
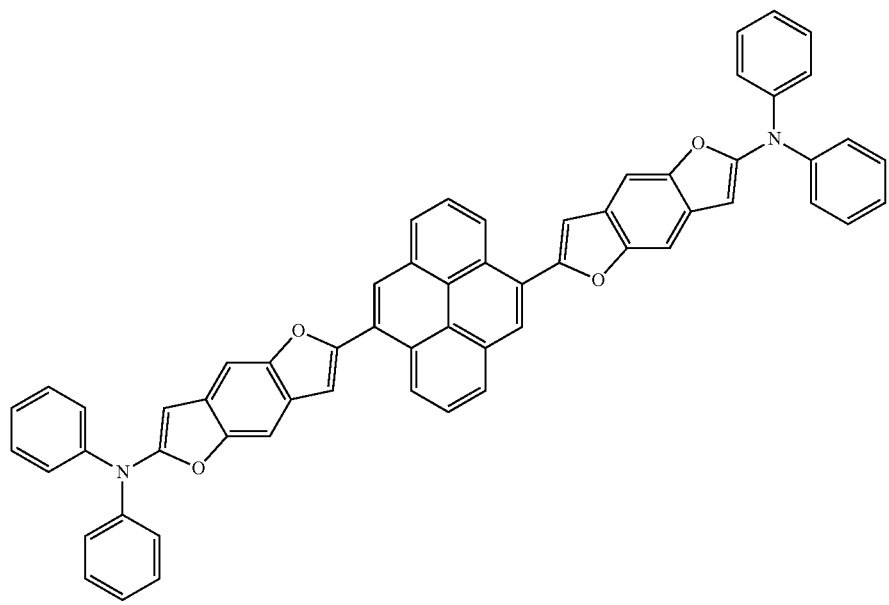
Compound 36
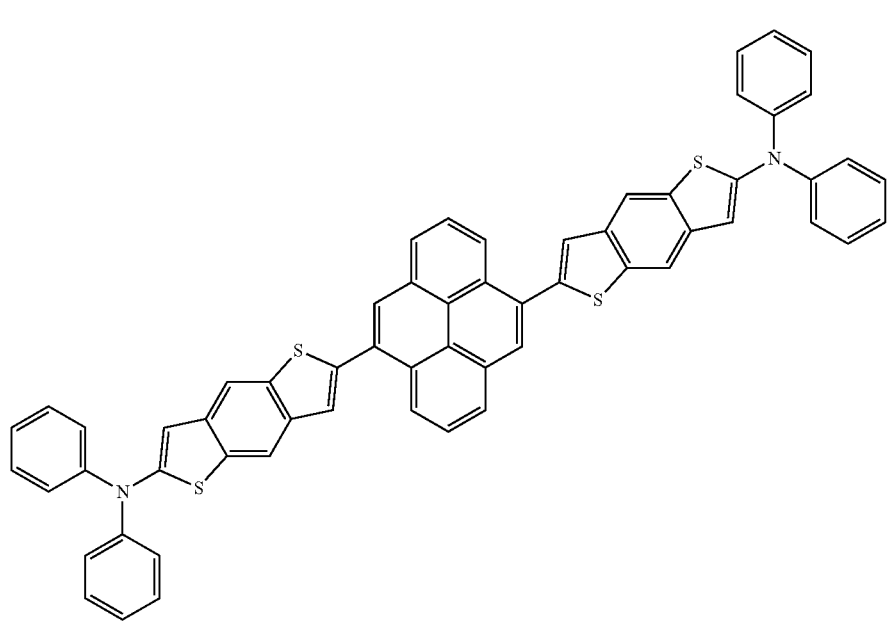
Compound 37
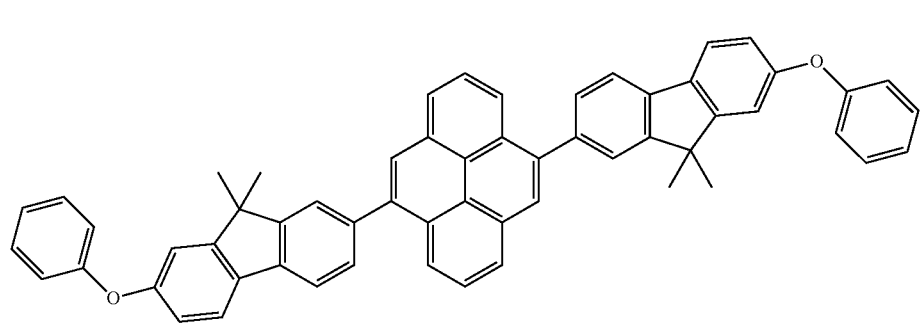

Compound 38
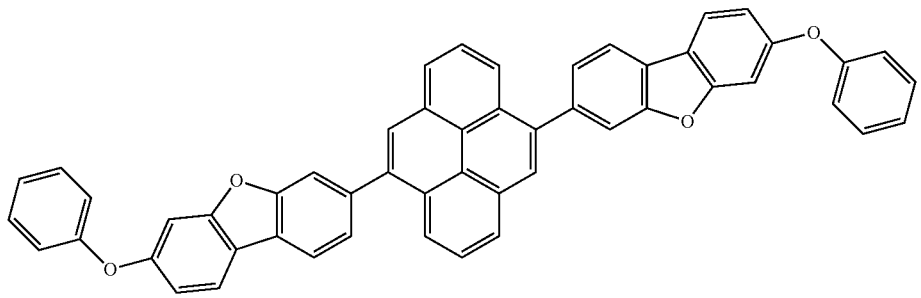
Compound 39
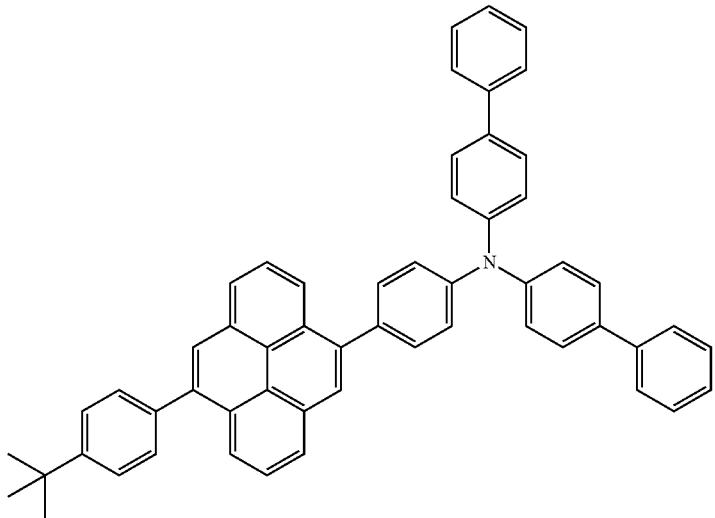
Compound 40
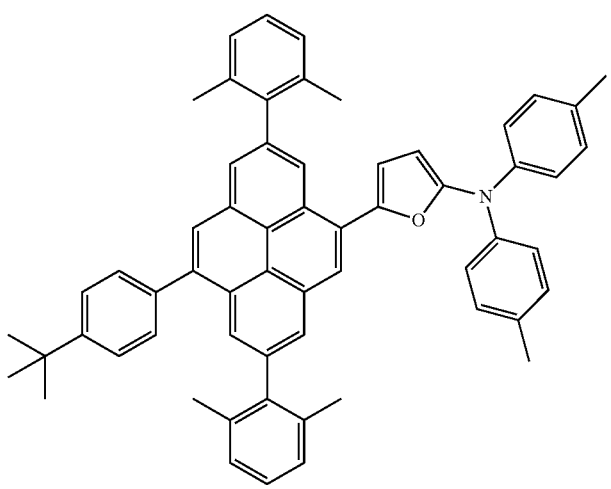

Compound 41
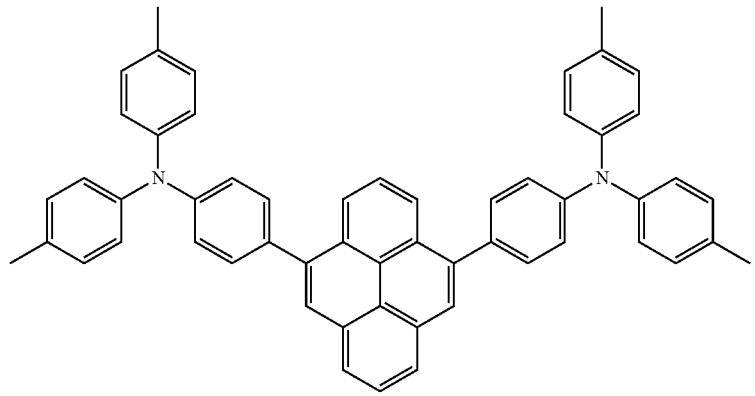
Compound 42
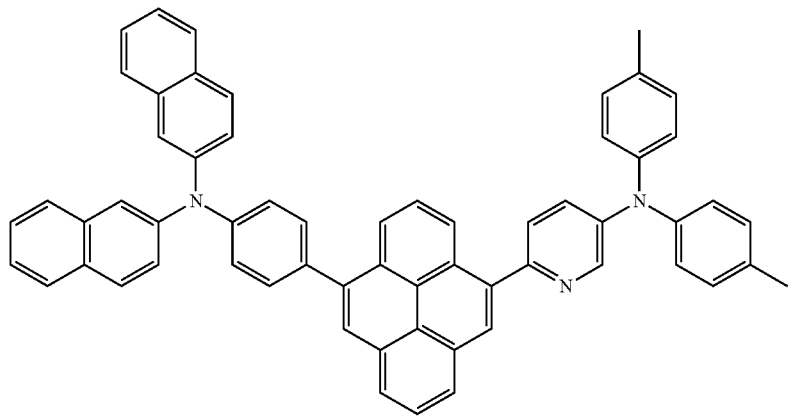
Compound 43
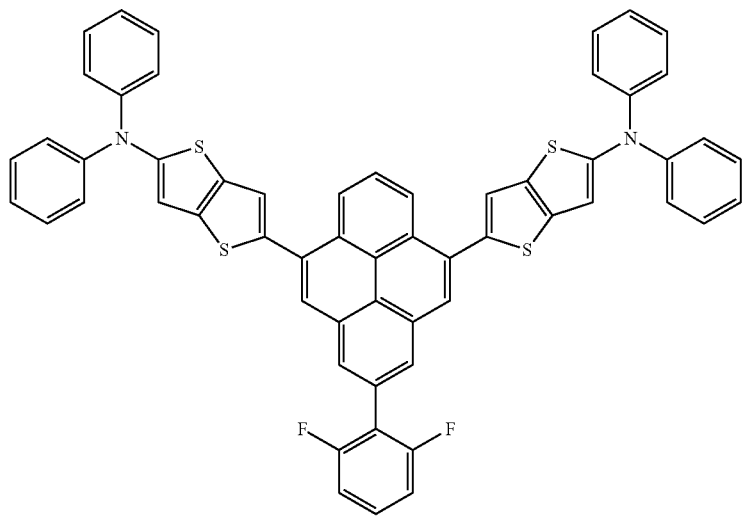

Compound 44
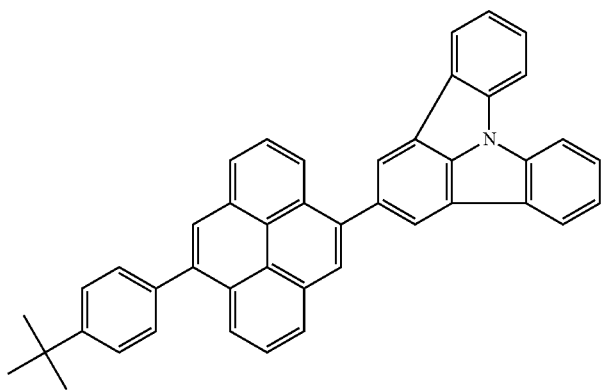
Compound 45
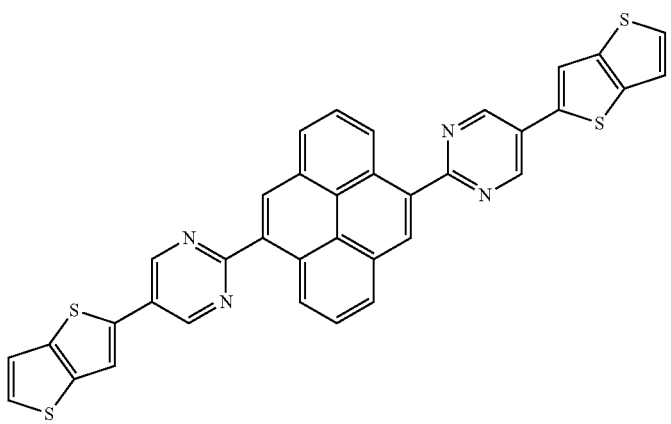
Compound 46
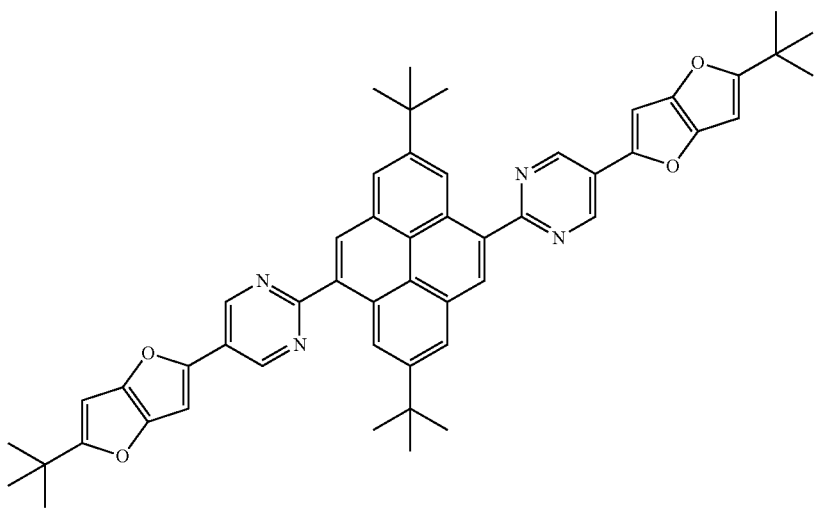

The compounds represented by the general formula (1) can be synthesized by combining known reactions, specifically by using the methods described in US2010/0244665 and KR10/2011/0057008. The following describes representative examples of specific synthesis procedures for the compounds represented by the general formula (1).
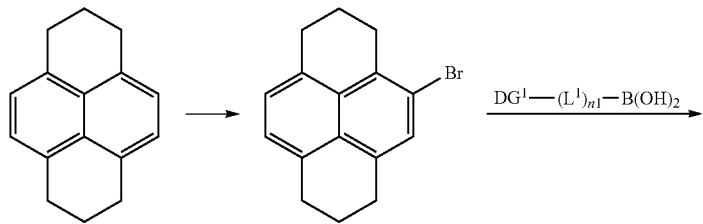
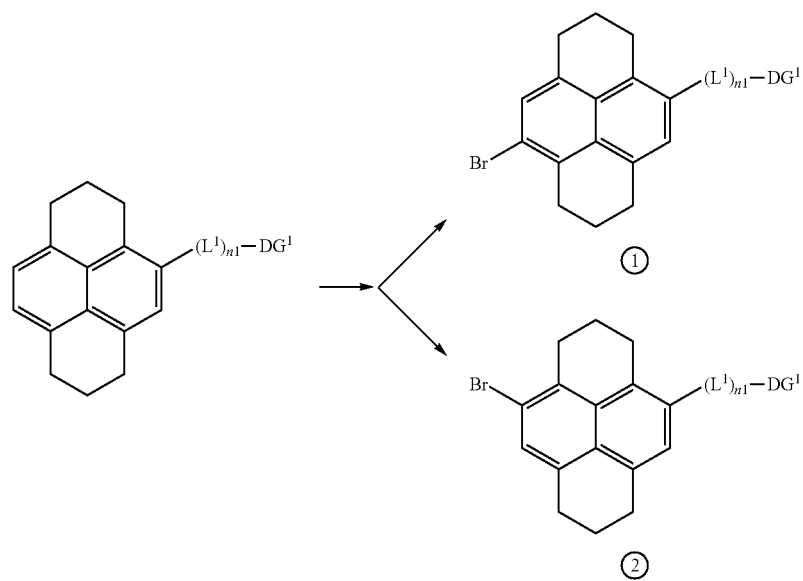
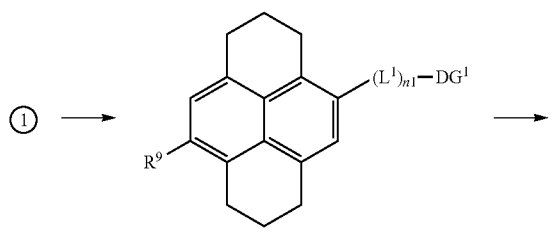

-continued
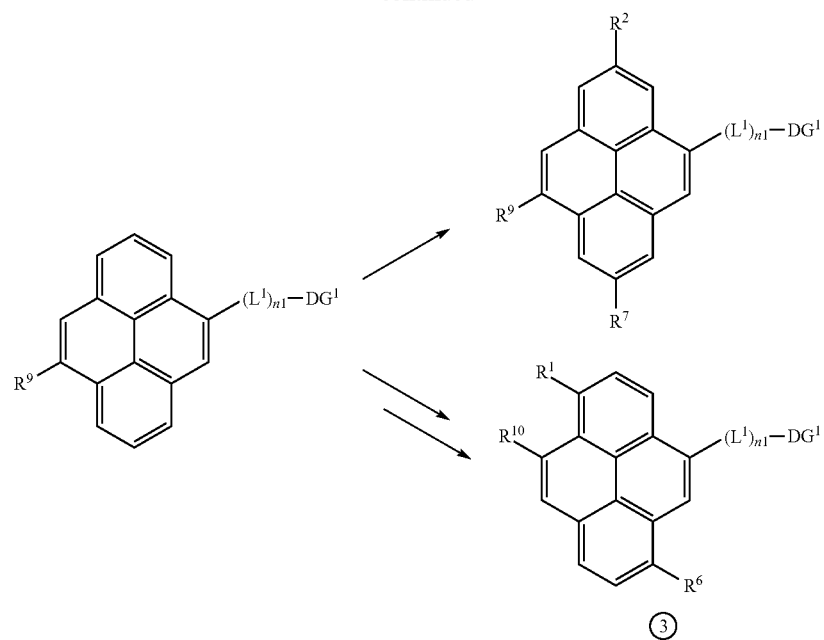
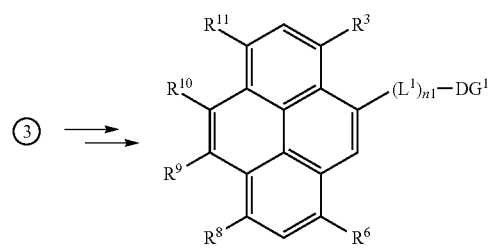
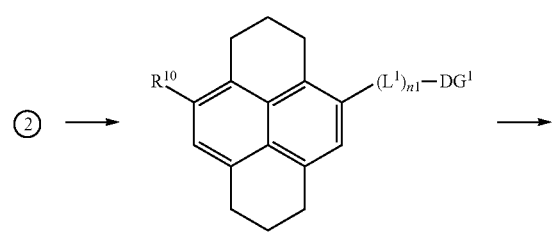

-continued

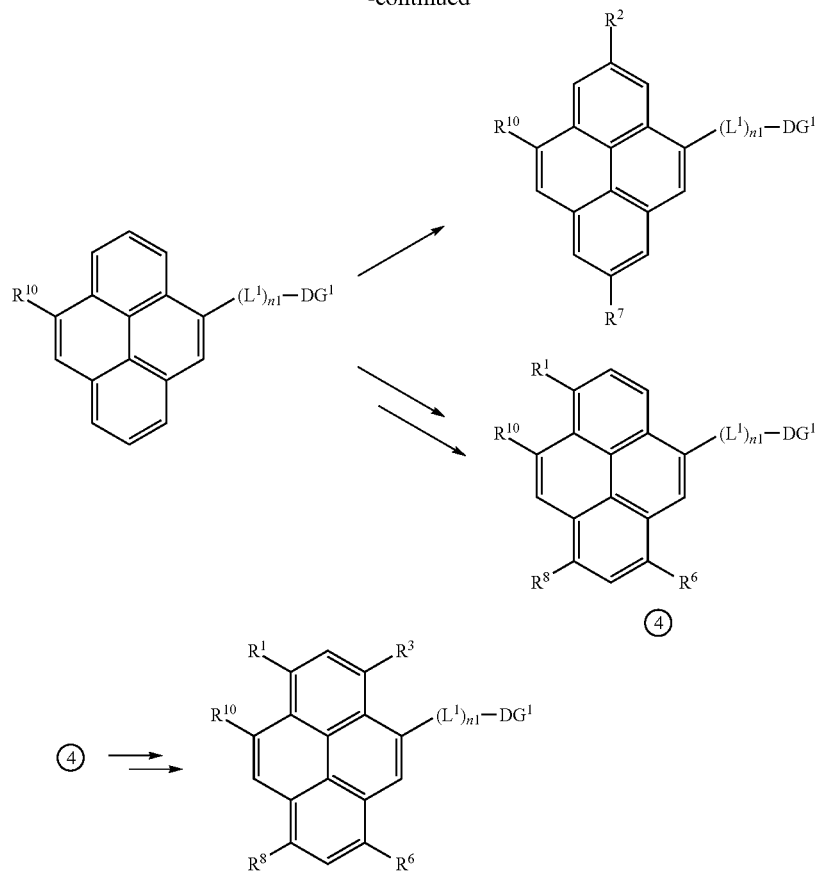

Each step can be performed by using the synthesis methods and the reaction conditions described in US2010/0244665 and KR10/2011/0057008.

After the synthesis, purification is preferably carried out by column chromatography, recrystallization, or the like, and then by sublimation purification. By the sublimation purification, organic impurities can be separated and inorganic salts, residual solvents, or the like can be removed effectively.

When the compounds represented by the general formula (1) are used as light emitting material, the light emitting material in the thin-film state preferably has a maximum luminous wavelength of less than 460 nm, more preferably 400 nm or more and less than 460 nm, particularly preferably 420 nm or more and less than 455 nm, still more preferably 430 nm or more and less than 455 nm, and most preferably 440 nm or more and less than 455 nm from the viewpoint of obtaining blue emission of high color purity.

Organic Electroluminescent Element

The organic electroluminescent element of the present invention includes a substrate, a pair of electrodes disposed on the substrate and that includes an anode and a cathode, and an organic layer disposed between the electrodes, wherein the organic layer contains a compound represented by the general formula (1).

The configuration of the organic electroluminescent element of the present invention is not particularly limited. FIG. 1 shows one example of the configuration of the organic electroluminescent element of the present invention. The organic electroluminescent element 10 of FIG. 1 has an organic layer between a pair of electrodes (an anode 3 and a cathode 9) on a substrate 2.

The element configuration of the organic electroluminescent element, the substrate, the cathode, and the anode are described in detail in, for example, JP-A-2008-270736, and the detailed description thereon in the publication can be applied to the present invention.

Hereinbelow, preferred embodiments of the organic electroluminescent element of the present invention will be described in detail in the order of the substrate, the electrodes, the organic layer, the protective layer, the sealing enclosure, a driving method, a light emitting wavelength, and applications.

Substrate

The organic electroluminescent element of the present invention has a substrate.

The substrate used in the present invention is preferably a substrate that does not scatter or diminish light starting from the organic layer. In the case of the organic material, those having excellent heat resistance, dimensional stability, solvent resistance, electricity insulating properties, and processibility are preferred.

Electrodes

The organic electroluminescent element of the present invention has a pair of electrodes including an anode and a cathode, disposed on the substrate.

In terms of the properties of the light emitting element, at least one electrode of a pair of electrodes, the anode and the cathode, is preferably transparent or semi-transparent.

Anode

The anode is usually anyone having a function as an electrode of supplying holes into an organic layer, and is not particularly limited in its shape, structure, size, or the like. Further, depending on the use and purpose of the light emitting element, the anode can be suitably selected from the known electrode materials. As described above, the anode is usually provided as a transparent anode.

Cathode

The cathode is usually any one having a function as an electrode of injecting electrons to an organic layer, and is not particularly limited in its shape, structure, size, or the like. Further, depending on the use and purpose of the light emitting element, the cathode can be suitably selected from the known electrode materials.

Organic Layer

The organic electroluminescent element of the present invention preferably has one or more organic layers disposed between the electrodes and that include a light emitting layer, wherein the light emitting layer contains a host material, and at least one compound represented by the foregoing general formula (1).

The organic layer is not particularly limited and can be suitably selected depending on the use and purpose of the organic electroluminescent element. However, the organic layer is preferably formed on a transparent electrode or a semi-transparent electrode. In this case, the organic layer is formed on the whole surface or one surface of the transparent electrode or the semi-transparent electrode.

The shape, the size, the thickness, or the like of the organic layer are not particularly limited, and can be suitably selected depending on the purpose.

Hereinbelow, the configuration of the organic layer, the method for forming an organic layer, preferred embodiments of the respective layers constituting the organic layer, and the materials used in the respective layers in the organic electroluminescent element of the present invention will be described in detail in order.

Configuration of Organic Layer

In the organic electroluminescent element of the present invention, the organic layer includes a light emitting layer. The organic layer preferably includes a charge transporting layer. The charge transporting layer refers to a layer in which charges move when voltage is applied to the organic electroluminescent element. Specific examples thereof include a hole injecting layer, a hole transporting layer, an electron blocking layer, a light emitting layer, a hole blocking layer, an electron transporting layer, and an electron injecting layer. When the charge transporting layer is a hole injecting layer, a hole transporting layer, an electron blocking layer, or a light emitting layer, an organic electroluminescent element with low cost as well as high efficiency can be prepared.

The compound represented by the general formula (1) is preferably contained in the light emitting layer in one or more organic layers disposed between the electrodes of the organic electroluminescent element.

The compound represented by the general formula (1) may be contained in other organic layers of the organic electroluminescent element of the present invention, provided that it does not depart from the gist of the present invention. Examples of the organic layer which may contain the compound represented by the general formula (1), other than the light emitting layer, include a hole injecting layer, a hole transporting layer, an electron transporting layer, an electron injecting layer, an exciton blocking layer, and a charge blocking layer (a hole blocking layer, an electron blocking layer, and the like); preferably any one of an exciton blocking layer, a charge blocking layer, an electron transporting layer, and an electron injecting layer; and more preferably an exciton blocking layer, a charge blocking layer, and an electron transporting layer.

When the compound represented by the general formula (1) is contained in the light emitting layer, the compound represented by the general formula (1) is contained in the amount of preferably 0.1 to 100% by mass, more preferably 1 to 50% by mass, and still more preferably 2 to 20% by mass, based on the total mass of the light emitting layer. Particularly preferably, the compound is contained in 3 to 10% by weight.

In a case where the compound represented by the general formula (1) is contained in the organic layer other than the light emitting layer, the compound represented by the general formula (1) is contained in the amount of preferably 70 to 100% by mass, more preferably 80 to 100% by mass, and still more preferably 90 to 100% by mass, based on the total mass of the organic layer.

Method for Forming Organic Layer

The respective organic layers in the organic electroluminescent element of the present invention can be suitably formed by any of dry film forming methods such as a deposition method and a sputtering method, wet type film forming methods (solution coating methods) such as a transfer method, a printing method, a spin-coating method, and a bar coating method.

In the organic electroluminescent element of the present invention, the organic layer disposed between the pair of electrodes is preferably formed by the deposition of a composition that includes at least one layer of the compound represented by the general formula (1).

Light Emitting Layer

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting. However, the light emitting layer in the present invention is not necessarily limited to the light emitting by such a mechanism.

The light emitting layer in the organic electroluminescent element of the present invention may be constituted with only a light emitting material such as the compound of the general formula (1) or may be constituted as a mixed layer of a host material and a light emitting material. The light emitting material may be made of a single kind or two or more kinds. The host material is preferably a charge transport material. The host material may be made of a single kind or two or more kinds. Examples thereof include a configuration in which an electron-transporting host material and a hole-transporting host material are mixed. Furthermore, the light emitting layer may contain a material which does not have charge transporting properties and which does not emit light.

Moreover, the light emitting layer may be made of a single layer or two or more layers. The respective layers may include the same light emitting materials or host materials, and may also include different materials from each other. In a case where plural light emitting layers are present, the respective light emitting layers may emit light in a different luminous color from each other.

The thickness of the light emitting layer is not particularly limited, but it is usually from 2 nm to 300 nm, and among these, from the viewpoint of external quantum efficiency, it is more preferably from 5 nm to 100 nm, and still more preferably from 10 nm to 50 nm.

In the organic electroluminescent element of the present invention, it is more preferable that the light emitting layer contains the compound represented by the general formula (1) and the compound represented by the general formula (1) is used as a light emitting material of the light emitting layer. The host material used in the present specification is a compound which usually plays a role in injecting or transporting charges in the light emitting layer and is also a compound which does not substantially emit light in itself. As used herein, it is meant by the terms "which does not substantially emit light" that the amount of light emitting from the compound which does not substantially emit light is preferably 5% or less, more preferably 3% or less, and still more preferably 1% or less of the total amount of light emitting in the whole of the element. The compound represented by the general formula (1) may also be used as the host material of the light emitting layer.

Light Emitting Material

In the organic electroluminescent element of the present invention, the compound represented by the general formula (1) is preferably used as a light emitting material, but even in this case, it can also be used in combination with a light emitting material other than the compound represented by the general formula (1). In addition, in the organic electroluminescent element of the present invention, even in a case where the compound represented by the general formula (1) is used as a host material of a light emitting layer or a case where it is used in the organic layer other than the light emitting layer, a light emitting material other than the compound represented by the general formula (1) may be used in the light emitting layer.

The light emitting material that can be used in the present invention is a fluorescent light emitting material. In addition, the light emitting layer in the present invention can contain two or more light emitting materials in order to improve color purity or widen a light emitting wavelength region.

The fluorescent light emitting material that can be used in the organic electroluminescent element of the present invention is described in detail in, for example, Paragraph Nos. [0100] to [0164] of JP-A-2008-270736, and Paragraph Nos. [0088] to [0090] of JP-A-2007-266458, the detailed description of which can be applied to the present invention.

The kind of the fluorescent light emitting material that can be used in the present invention is not particularly limited, but examples thereof include those other than the compound represented by the general formula (1), for example, benzoxazole, benzimidazole, benzothiazole, styrylbenzene, polyphenyl, diphenylbutadiene, tetraphenylbutadiene, naphthalimide, coumarin, pyrane, perinone, oxadiazole, aldazine, pyralizine, cyclopentadiene, bis-styrylanthracene, quinacridone, pyrrolopyridine, thiadiazolopyridine, cyclopentadiene, styrylamine, aromatic fused polycyclic compounds (anthracene, phenanthroline, pyrene, perylene, rubrene, pentacene, and the like), a variety of metal complexes typified by metal complexes of 8-quinolinol, pyrromethene complexes, and rare-earth complexes, polymer compounds such as polythiophene, polyphenylene, and polyphenylenevinylene, organic silanes, and derivatives thereof.

In addition, the compound described in [0082] of JP-A-2010-111620 can also be used as a light emitting material.

The light emitting layer in the organic electroluminescent element of the present invention may be constituted with only a light emitting material or may be constituted as a mixed layer of a host material and a light emitting material. The light emitting material may be made of a single kind or two or more kinds. The host material is preferably a charge transport material. The host material may be made of a single kind or two or more kinds. Examples thereof include a configuration in which an electron-transporting host material and a hole-transporting host material are mixed. Furthermore, the light emitting layer may contain a material which does not have charge transporting properties and which does not emit light.

Moreover, the light emitting layer may be made of a single layer or two or more layers. The respective layers may include the same light emitting materials or host materials, and may also include different materials from each other. In a case where plural light emitting layers are present, the respective light emitting layers may emit light in different luminous colors from each other.

Host Material

The host material is a compound that usually plays a role in injecting or transporting charges in the light emitting layer and is also a compound which does not substantially emit light in itself. As used herein, it is meant by the terms "which does not substantially emit light" that the amount of light emitting from the compound which does not substantially emit light is preferably 5% or less, more preferably 3% or less, and still more preferably 1% or less of the total amount of light emitting in the whole of the element.

Examples of the host material that can be used in the organic electroluminescent element of the present invention include the following compounds.

Conductive high-molecular oligomers such as pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin-based compounds, aromatic hydrocarbon compounds with fused rings (fluorene, naphthalene, phenanthrene, triphenylene, and the like), polysilane-based compounds, poly (N-vinylcarbazole), aniline-based copolymers, thiophene oligomers, and polythiophene, organic silanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, phthalocyanine, and a variety of metal complexes typified by metal complexes of 8-quinolinol derivatives and metal complexes having metal phthalocyanine, benzoxazole, or benzothiazole as a ligand thereof, and derivatives thereof (which may have a substituent or a fused ring). In addition, the compounds described in [0081] or [0083] of JP-A-2010-111620 can also be used.

Among these, carbazole, dibenzothiophene, dibenzofuran, arylamine, aromatic hydrocarbon compounds with fused rings, and metal complexes are preferred, and aromatic hydrocarbon compounds with fused rings are particularly preferable since they are stable. As the aromatic hydrocarbon compounds with fused rings, naphthalene-based compounds, anthracene-based compounds, phenanthrene-based compounds, triphenylene-based compounds, and pyrene-based compounds are preferred; anthracene-based compounds and pyrene-based compounds are more preferred; and anthracene-based compounds are particularly preferred. As the anthracene-based compounds, those described in [0033] to [0064] of WO 2010/134350 are particularly preferred, and examples thereof include Compounds H-1 and H-2 as described later.

In the organic electroluminescent element of the present invention, the host material contained in the light emitting layer preferably has a hydrocarbon fused ring structure of 10 to 50 carbon atoms.

The hydrocarbon fused ring structure of 10 to 50 carbon atoms is preferably naphthalene, phenanthrene, benzo[c]phenanthrene, anthracene, pyrene, triphenylene, or chrysene, more preferably naphthalene, phenanthrene, benzo[c]phenanthrene, or anthracene, most preferably anthracene. Specifically, the hydrocarbon fused ring structure of 10 to 50 carbon atoms in the host material is further preferably an anthracene skeleton. Further, it is particularly preferable that the hydrocarbon fused ring structure of 10 to 50 carbon atoms is a compound configured from only carbon, and hydrogen or deuterium.

The host material that can be used in the light emitting layer in the organic electroluminescent element of the present invention may be a host material having hole transporting properties or a host material having electron transporting properties.

In the light emitting layer, the singlet lowest excited energy ($S_1$ energy) in the film state of the host material is preferably higher than the $S_1$ energy of the light emitting material in views of color purity, luminous efficiency, and driving durability. The $S_1$ of the host material is preferably higher than the $S_1$ of the light emitting material by 0.1 eV or more, more preferably by 0.2 eV or more, and still more preferably by 0.3 eV or more.

When $S_1$ in the film state of the host material is lower than $S_1$ of the light emitting material, the light emitting is lost, and thus, the host material is required to have higher $S_1$ than the $S_1$ of the light emitting material. Further, even in a case where $S_1$ of the host material is higher than the $S_1$ of the light emitting material, a small difference in the $S_1$ of the both leads to partial reverse energy movement from the light emitting material to the host material, which causes reduction in efficiency, color purity, or durability. Therefore, there is a demand for a host material having a sufficiently high $S_1$, and high chemical stability and carrier injecting/transporting properties.

Furthermore, the content of the host compound in the light emitting layer in the organic electroluminescent element of the present invention is not particularly limited, but from the viewpoint of luminous efficiency and driving voltage, it is preferably from 15 to 98% by mass, more preferably 80 to 97% by mass based on the total mass of the compounds forming the light emitting layer. When the light emitting layer includes plural kinds of host compounds containing the compound represented by the general formula (1), the content of the compound represented by the general formula (1) is preferably from 50 to 99% by mass based on the total host compounds.

Other Layers

The organic electroluminescent element of the present invention may contain layers other than the light emitting layer.

Examples of the organic layer other than the light emitting layer which may be included in the organic layer include a hole injecting layer, a hole transporting layer, a blocking layer (a hole blocking layer, an exciton blocking layer, and the like), and an electron transporting layer. Examples of the specific layer configuration include those below, but the present invention is not limited to these configurations.

Anode/hole transporting layer/light emitting layer/electron transporting layer/cathode, Anode/hole transporting layer/light emitting layer/blocking layer/electron transporting layer/cathode, Anode/hole transporting layer/light emitting layer/blocking layer/electron transporting layer/electron injecting layer/cathode, Anode/hole injecting layer/hole transporting layer/light emitting layer/blocking layer/electron transporting layer/cathode, Anode/hole injecting layer/hole transporting layer/light emitting layer/electron transporting layer/electron injecting layer/cathode, Anode/hole injecting layer/hole transporting layer/light emitting layer/blocking layer/electron transporting layer/electron injecting layer/cathode, Anode/hole injecting layer/hole transporting layer/blocking layer/light emitting layer/blocking layer/electron transporting layer/electron injecting layer/cathode.

The organic electroluminescent element of the present invention preferably includes at least one layer of organic layers that are preferably disposed between the (A) anode and the light emitting layer. Examples of the organic layer that is preferably disposed between the (A) anode and the light emitting layer include an hole injecting layer, a hole transporting layer, and an electron blocking layer from the anode side.

The organic electroluminescent element of the present invention preferably includes at least one layer of organic layers that are preferably disposed between the (B) cathode and the light emitting layer. Examples of the organic layer that is preferably disposed between the (B) cathode and the light emitting layer include an electron injecting layer, an electron transporting layer, and a hole blocking layer from the cathode side.

Specifically, an example of the preferred embodiments of the organic electroluminescent element of the present invention is the embodiment shown in FIG. 1, in which a hole injecting layer 4, a hole transporting layer 5, a light emitting layer 6, a hole blocking layer 7, and an electron transporting layer 8 are laminated in this order as the organic layer from the anode 3 side.

Hereinbelow, these layers other than the light emitting layer which the organic electroluminescent element of the present invention may have will be described.

(A) Organic Layer Preferably Disposed Between Anode and Light Emitting Layer

First, (A) the organic layer preferably disposed between the anode and the light emitting layer will be described.

(A-1) Hole Injecting Layer and Hole Transporting Layer

The hole injecting layer and the hole transporting layer are layers having a function of receiving holes from the anode or the anode side and transporting them to the cathode side.

The light emitting element of the present invention preferably includes at least one layer of organic layers between the light emitting layer and the anode, and the organic layer preferably includes at least one of compounds out of the compounds represented by the following general formulae (Sa-1), (Sb-1), and (Sc-1).

General Formula (Sa-1)

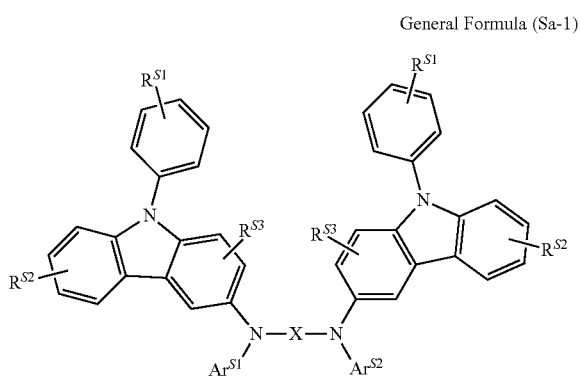

(wherein X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, or a substituted or unsubstituted heterocyclic group having 2 to 30 carbon atoms, or a group formed by a combination of these groups. $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocyclic ring having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms).

General Formula (Sb-1)

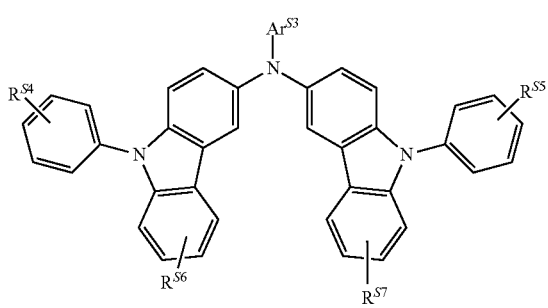

(wherein $R^{S4}$, $R^{S5}$, $R^{S6}$, and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocyclic ring having 2 to 30 carbon atoms, a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$, and $R^{S7}$ may be bonded to each other to form a saturated carbocycle or an unsaturated carbocycle. $Ar^{S3}$ represents a substituted or unsubstituted aryl group having 6 to 30 carbon atoms, or a substituted or unsubstituted heteroaryl group having 2 to 30 carbon atoms).

General Formula (Sc-1)

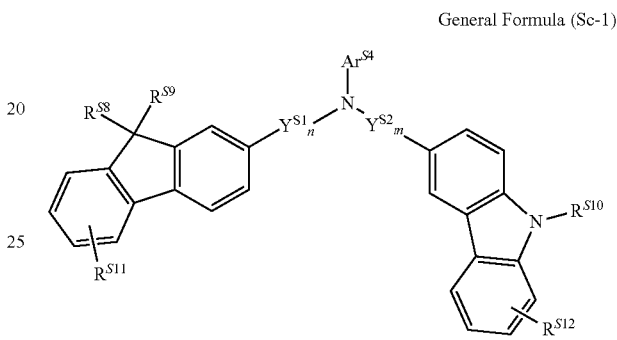

(wherein $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocyclic ring having 2 to 30 carbon atoms, a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ each independently represent a substituted or unsubstituted alkylene group having 1 to 30 carbon atoms, or a substituted or unsubstituted arylene group having 6 to 30 carbon atoms. n and m each independently represent an integer of 0 to 5).

The general formula (Sa-1) will be described.

In the general formula (Sa-1), X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, or a substituted or unsubstituted heterocyclic group having 2 to 30 carbon atoms, or a group formed by a combination of these groups. X is preferably a substituted or unsubstituted arylene group having 6 to 30 carbon atoms, more preferably a substituted or unsubstituted phenylene, a substituted or unsubstituted biphenylene, and a substituted or unsubstituted naphthylene, and still more preferably a substituted or unsubstituted biphenylene.

$R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocyclic ring having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S1}$, $R^{S2}$, and $R^{S3}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms. $Ar^{S1}$ and $Ar^{S2}$ are preferably a substituted or unsubstituted phenyl group.

Next, the general formula (Sb-1) will be described.

In the general formula (Sb-1), $R^{S4}$, $R^{S5}$, $R^{S6}$ and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocyclic ring having 2 to 30 carbon atoms, or a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$ and $R^{S7}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S4}$, $R^{S5}$, $R^{S6}$ and $R^{S7}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S3}$ represents a substituted or unsubstituted aryl group having 6 to 30 carbon atoms, or a substituted or unsubstituted heteroaryl group having 2 to 30 carbon atoms. $Ar^{S3}$ is preferably a substituted or unsubstituted phenyl group.

Next, the general formula (Sc-1) will be described.

In the general formula (Sc-1), $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S8}$ and $R^{S9}$ are preferably a substituted or unsubstituted alkyl group having 1 to 30 carbon atoms, or a substituted or unsubstituted aryl group having 6 to 30 carbon atoms, and more preferably a methyl group or a phenyl group. $R^{S10}$ is a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ is preferably a substituted or unsubstituted aryl group having 6 to 30 carbon atoms, and more preferably a phenyl group. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocyclic ring having 2 to 30 carbon atoms, a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to forma saturated carbocycle or an unsaturated carbocycle. Examples of the saturated carbocycle or the unsaturated carbocycle include naphthalene, azulene, anthracene, fluorene, and phenalene. $R^{S11}$ and $R^{S12}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ represent substituted or unsubstituted alkylene having 1 to 30 carbon atoms, or substituted or unsubstituted arylene having 6 to 30 carbon atoms. $Y^{S1}$ and $Y^{S2}$ are preferably substituted or unsubstituted arylene having 6 to 30 carbon atoms, and more preferably substituted or unsubstituted phenylene. n is an integer of 0 to 5, preferably 0 to 3, more preferably 0 to 2, and still more preferably 0. m is an integer of 0 to 5, preferably 0 to 3, more preferably 0 to 2, and still more preferably 1.

The general formula (Sa-1) is preferably a compound represented by the following general formula (Sa-2).

General Formula (Sa-2)

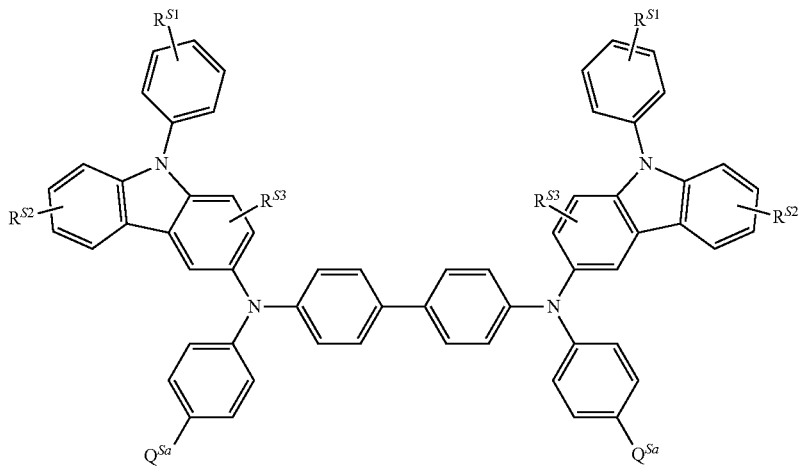

(wherein $R^{S1}$, $R^{S2}$ and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocyclic ring having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, $R^{S3}$ may be bonded to each other to form a saturated carbocycle or an unsaturated carbocycle. $Q^{Sa}$ each independently represent a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocyclic ring having 2 to 30 carbon atoms, or a substituted or unsubstituted amino group).

The general formula (Sa-2) will be described. $R^{S1}$, $R^{S2}$, and $R^{S3}$ have the same definitions as those in the general formula (Sa-1), and their preferred ranges are also the same. Each $Q^{Sa}$ independently represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocyclic ring having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably a hydrogen atom or a substituted or unsubstituted alkyl group having 1 to 30 carbon atoms, and still more preferably a hydrogen atom.

The general formula (Sb-1) is preferably a compound represented by the following general formula (Sb-2).

General Formula (Sb-2)

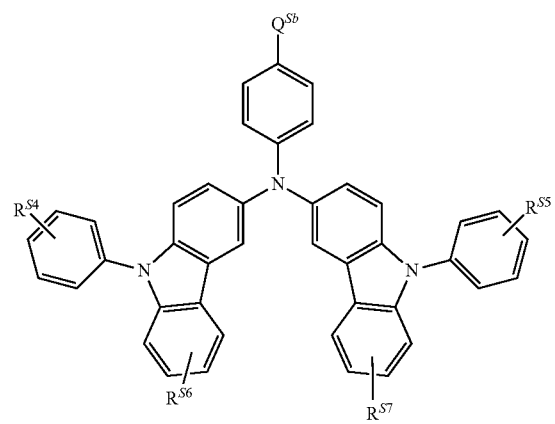

(wherein $R^{S4}$, $R^{S5}$, $R^{S6}$ and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocyclic ring having 2 to 30 carbon atoms, a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$ and $R^{S7}$ may be bonded to each other to form a saturated carbocycle or an unsaturated carbocycle. $Q^{Sb}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocyclic ring having 2 to 30 carbon atoms, or a substituted or unsubstituted amino group).

The general formula (Sb-2) will be described. $R^{S4}$, $R^{S5}$, $R^{S6}$ and $R^{S7}$ have the same definitions as those in the general formula (Sb-1), and their preferred ranges are also the same. $Q^{Sb}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocyclic ring having 2 to 30 carbon atoms, or a substituted or unsubstituted amino group. $Q^{Sb}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably a hydrogen atom, or a substituted or unsubstituted alkyl group having 1 to 30 carbon atoms, and still more preferably a hydrogen atom.

The general formula (Sc-1) is preferably a compound represented by the following general formula (Sc-2).

General Formula (Sc-2)

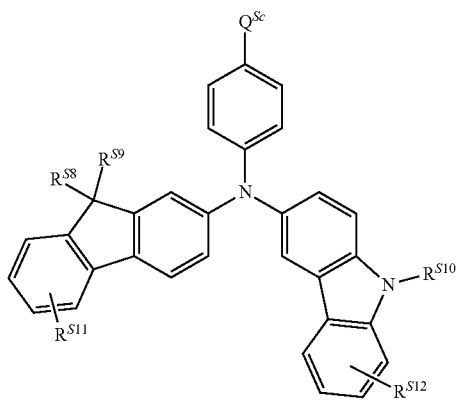

(wherein $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocyclic ring having 2 to 30 carbon atoms, or a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to forma saturated carbocycle or an unsaturated carbocycle. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocyclic ring having 2 to 30 carbon atoms, or a substituted or unsubstituted amino group).

The general formula (Sc-2) will be described. $R^{S8}$, $R^{S9}$, $R^{S10}$, $R^{S11}$ and $R^{S12}$ have the same definitions as those in the general formula (Sc-1), and their preferred ranges are also the same. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocyclic ring having 2 to 30 carbon atoms, or a substituted or unsubstituted amino group. $Q^{Sc}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably a hydrogen atom, or a substituted or unsubstituted aryl group having 6 to 30 carbon atoms, and still more preferably a phenyl group.

Specific examples of the compounds represented by the general formulae (Sa-1), (Sb-1), and (Sc-1) include the following ones. However, the present invention is not limited to the following specific examples.

1

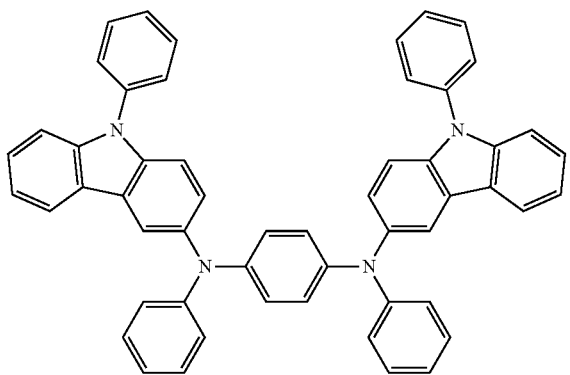

2

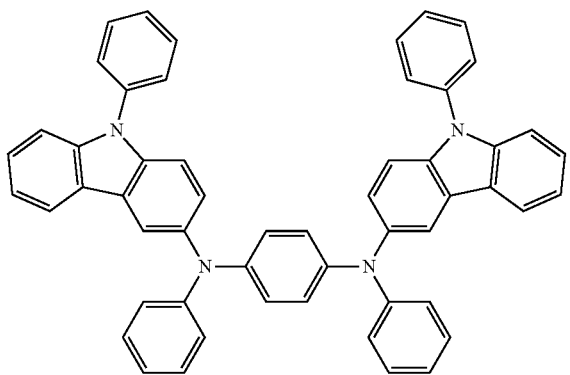

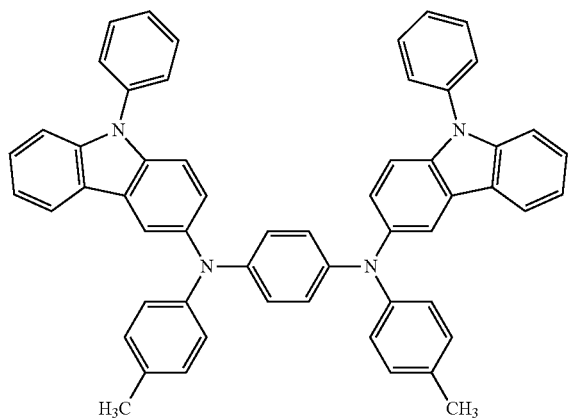
3
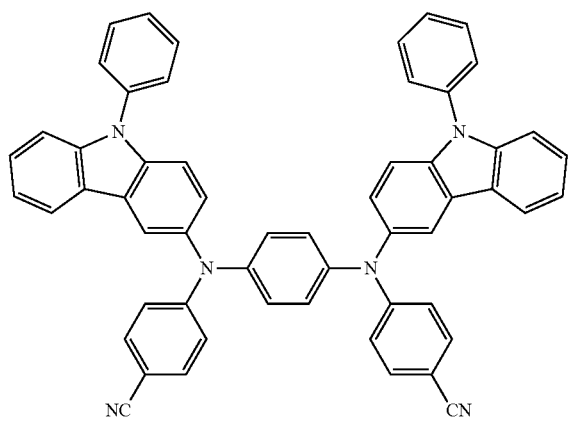
4
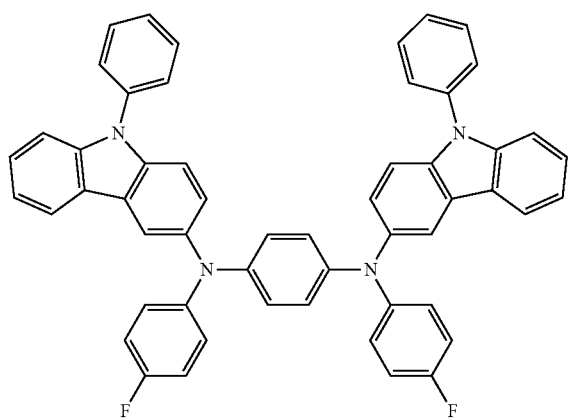
5
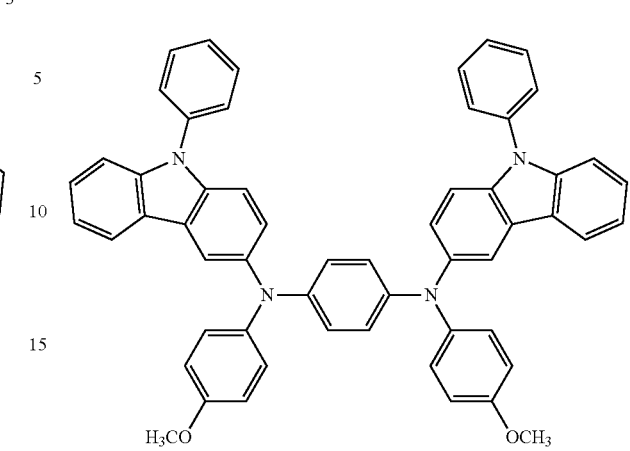
6
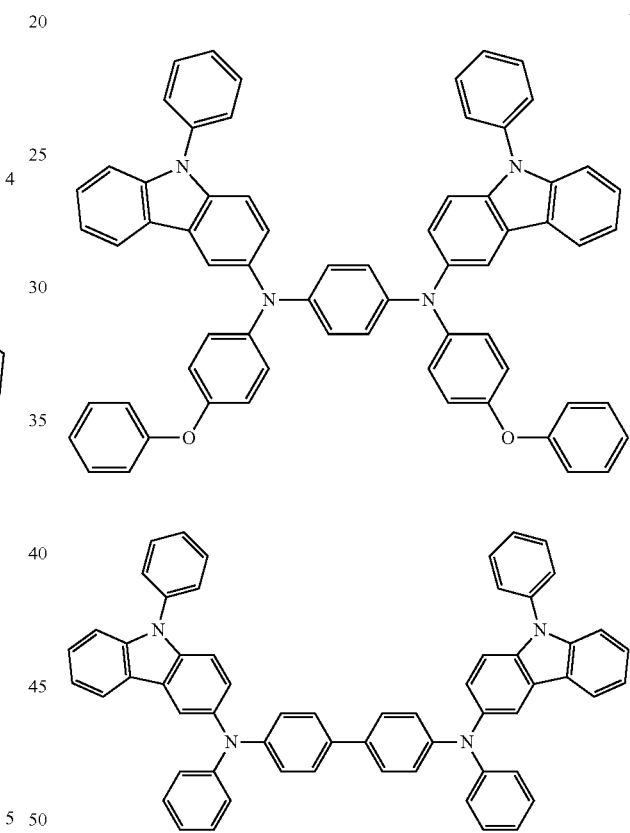

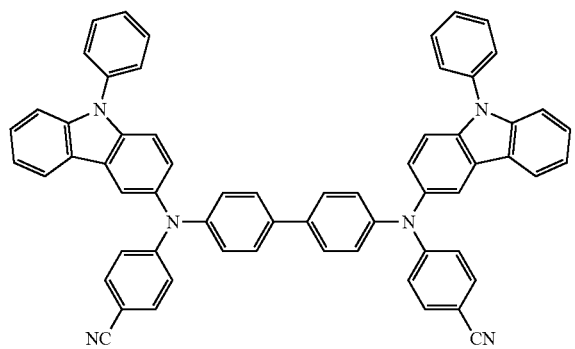
10
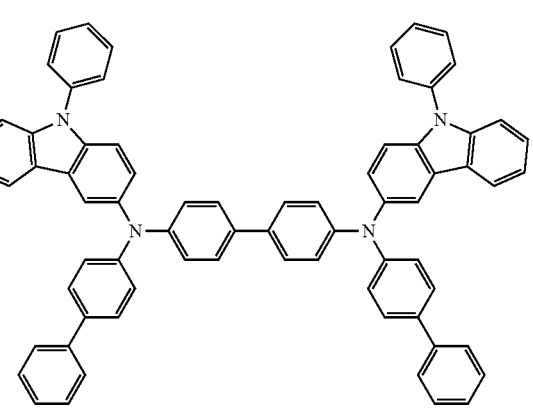
14
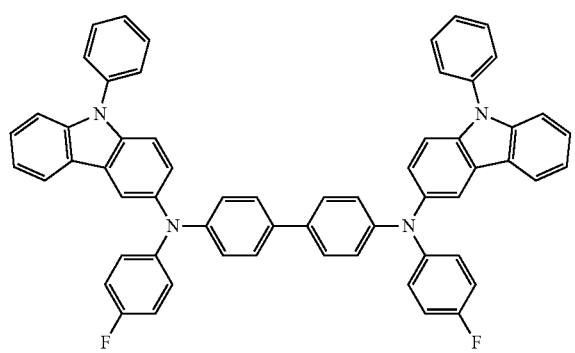
11
12
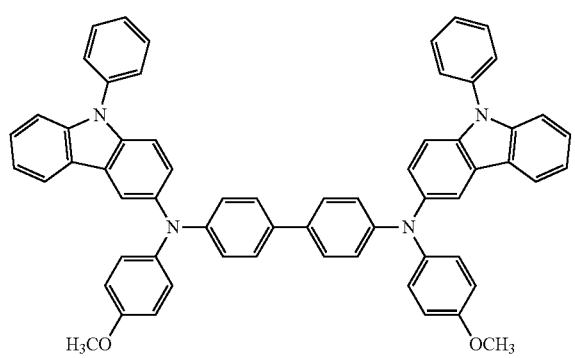
13
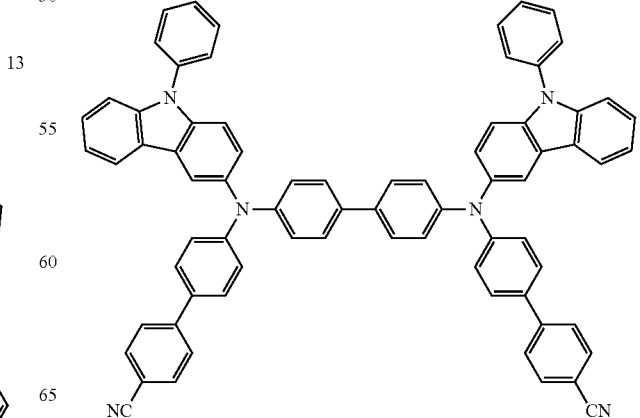
15
16

17
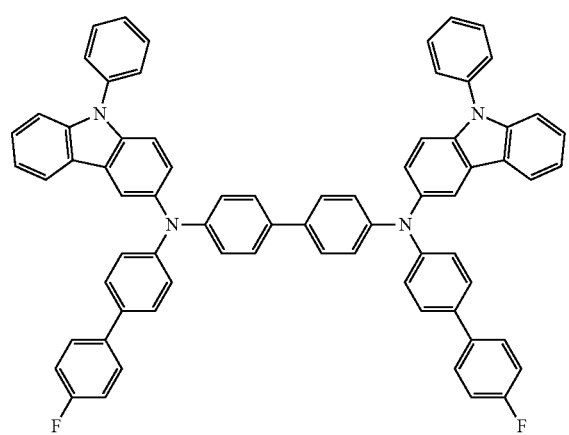
18
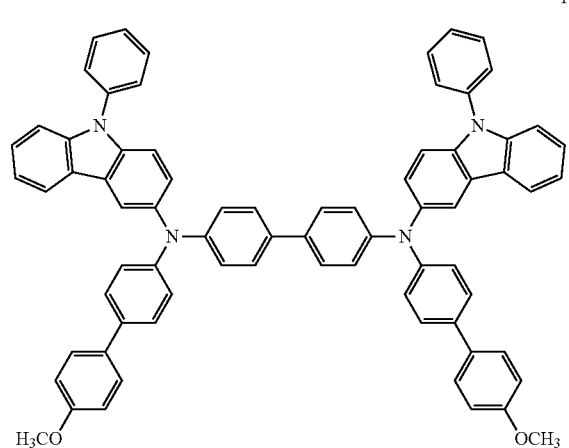
19
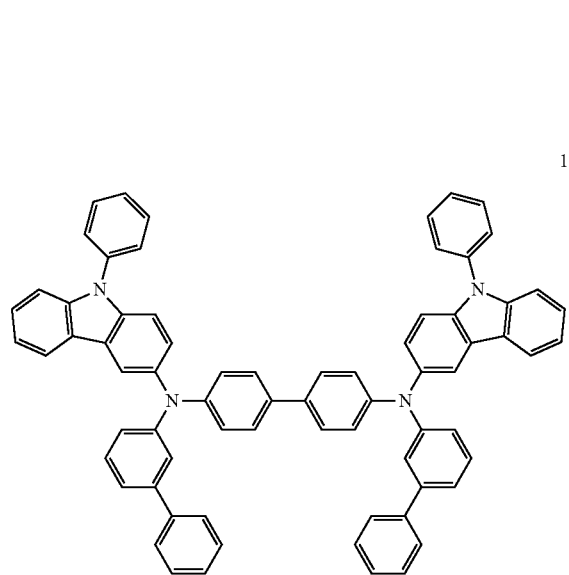
20
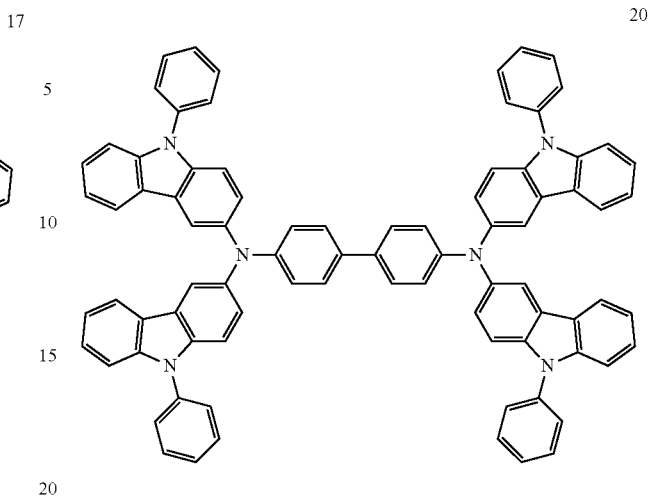
21
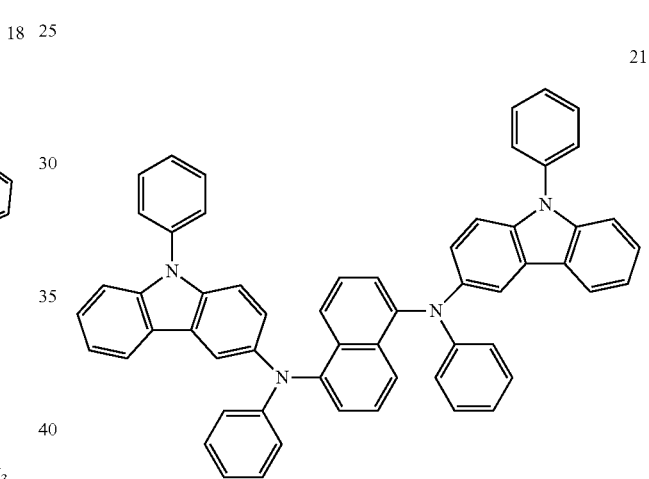
22
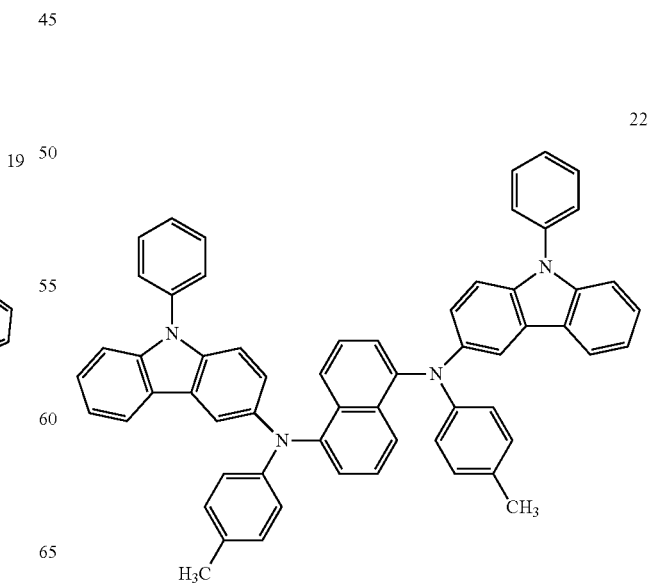

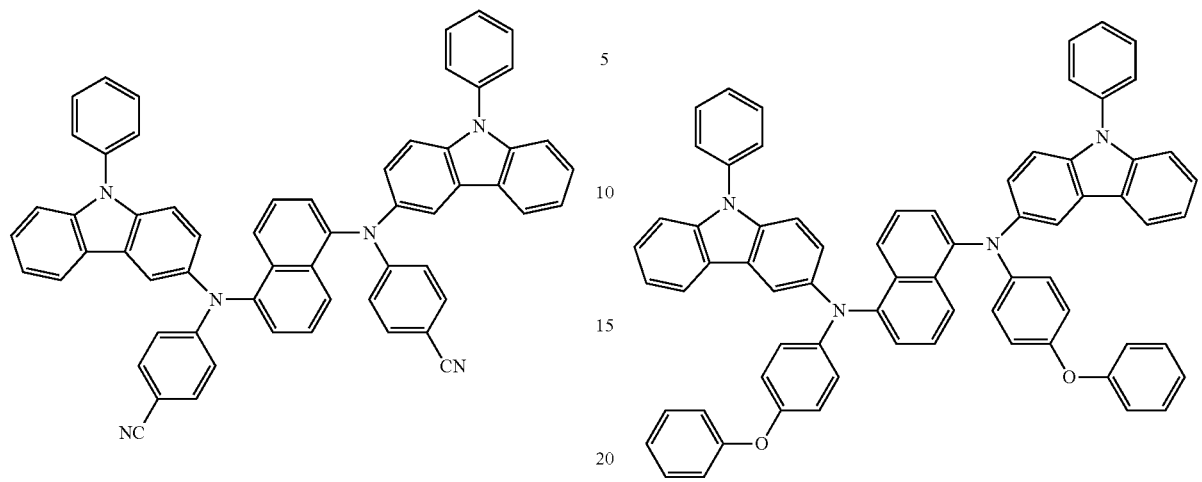
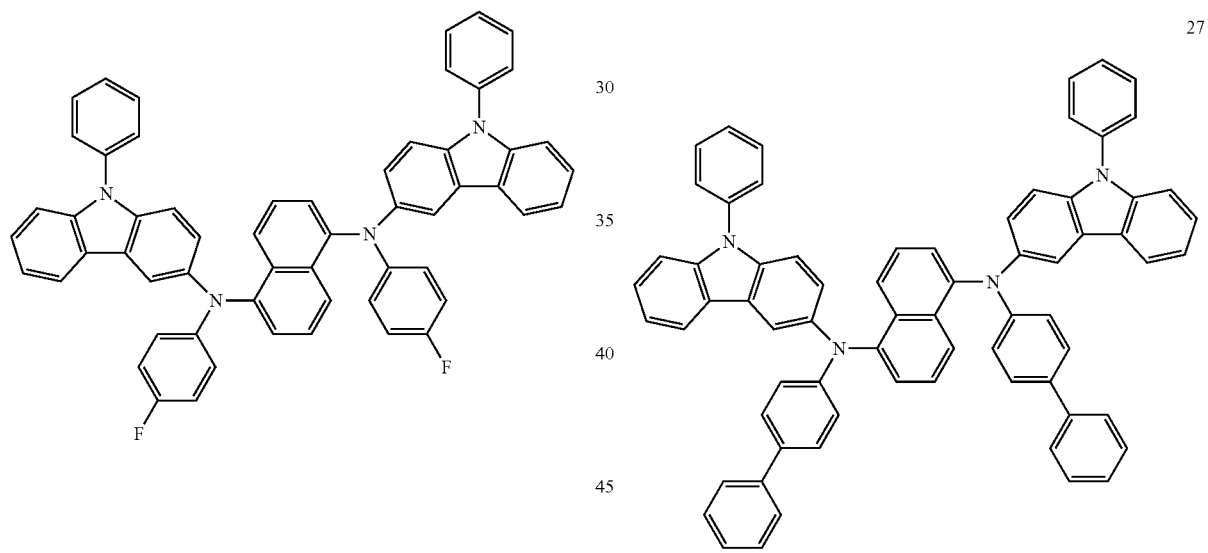
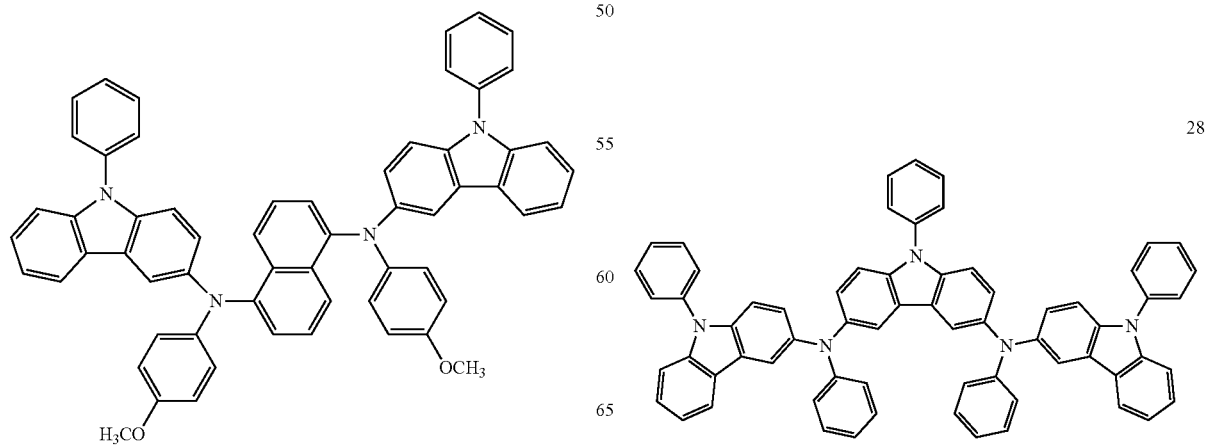

29
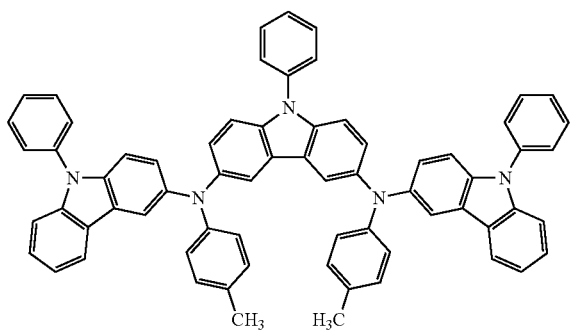
30
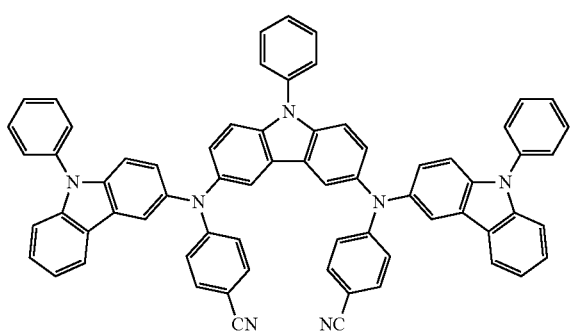
33
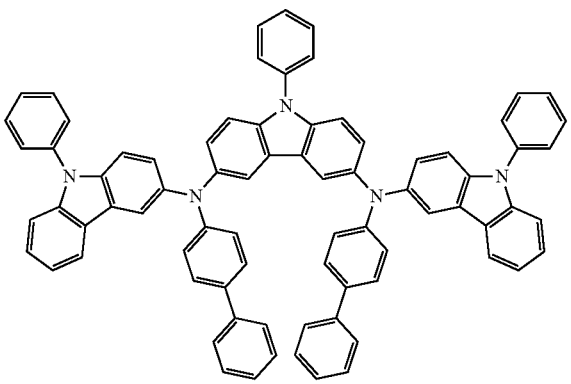
34
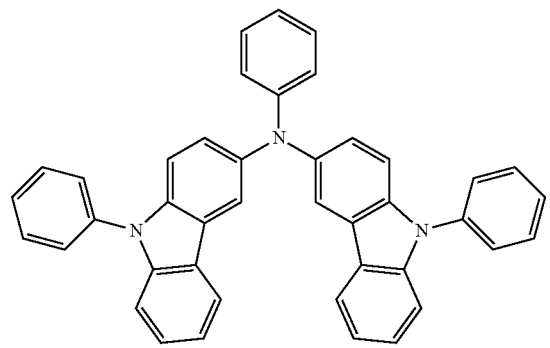
35
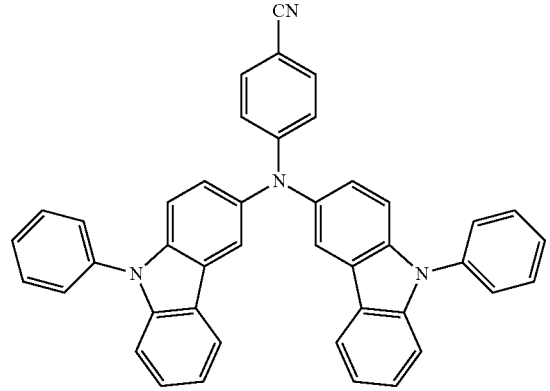
36
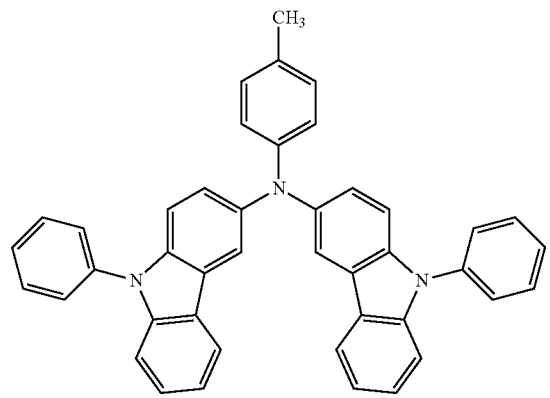

37
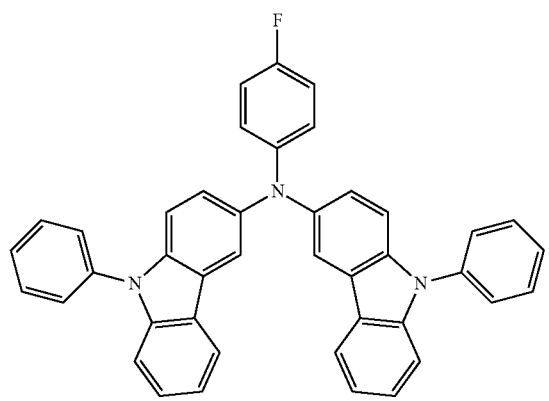
38
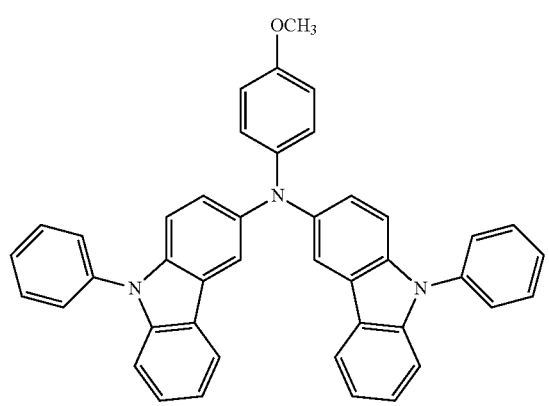
39
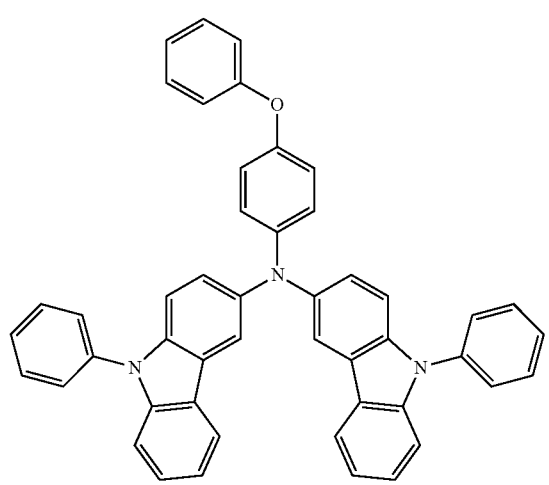
40
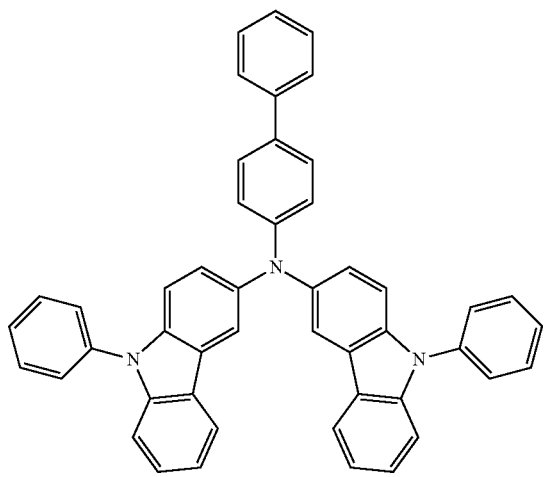
41
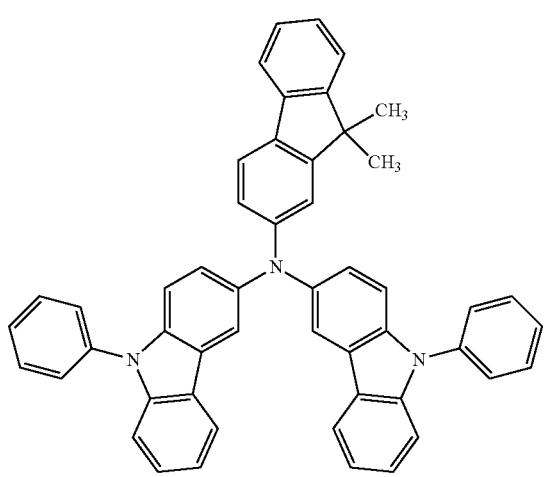
42
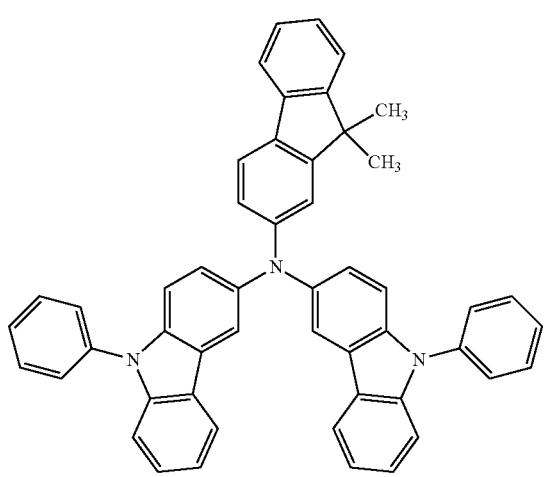

43
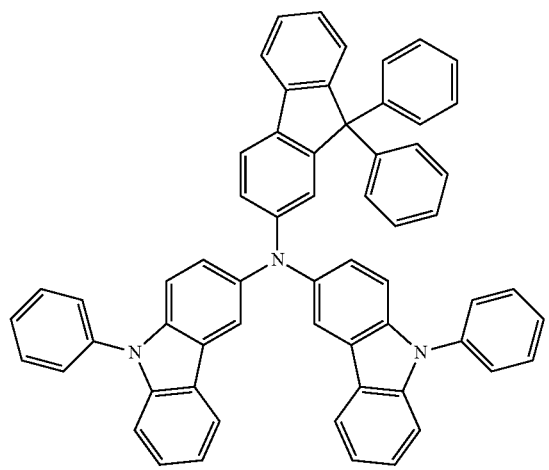
44
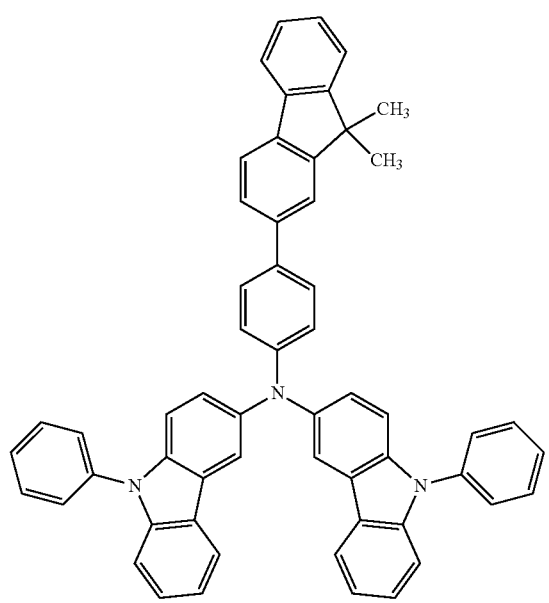
45
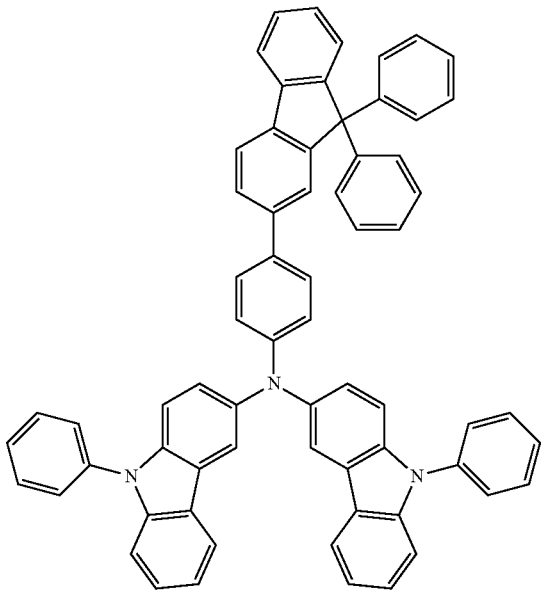
46
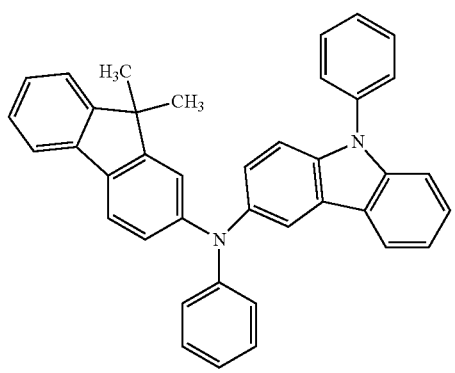
47
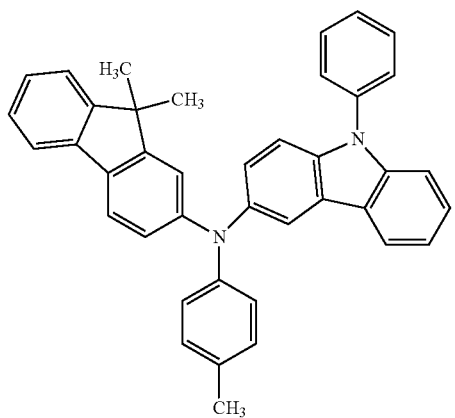

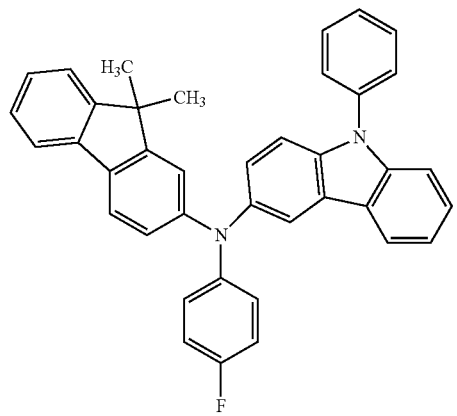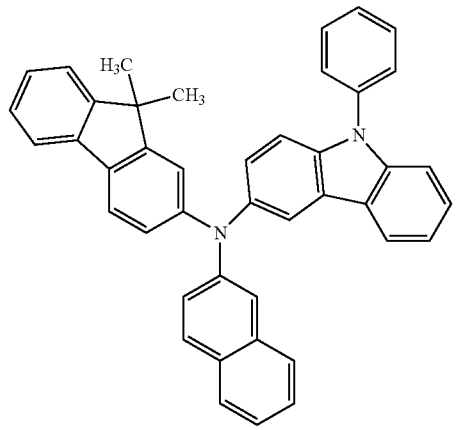

54
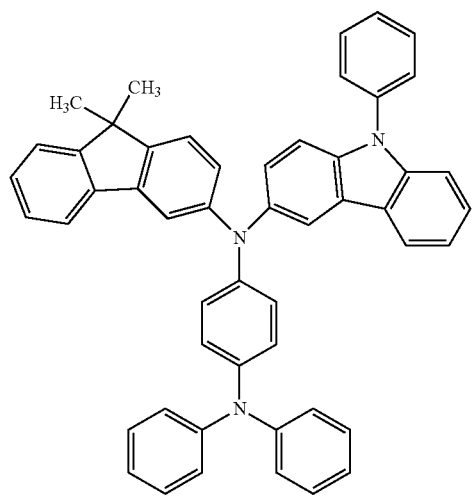
55
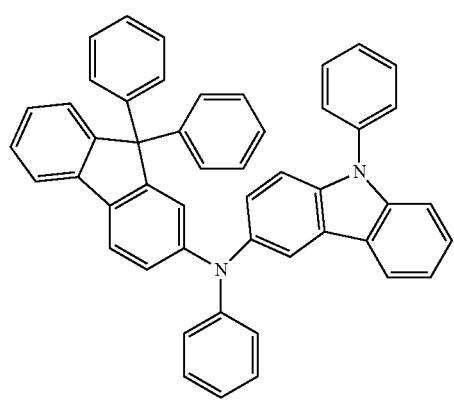
56
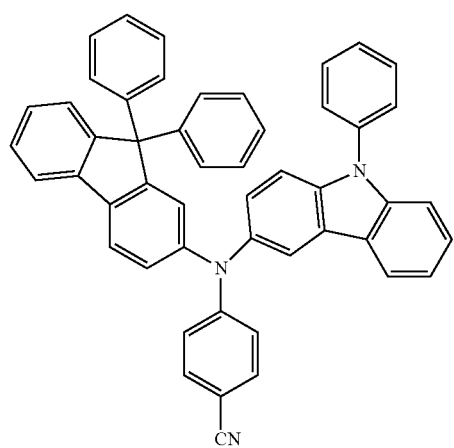
57
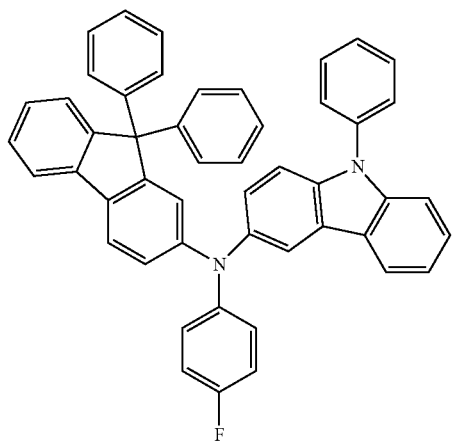
58
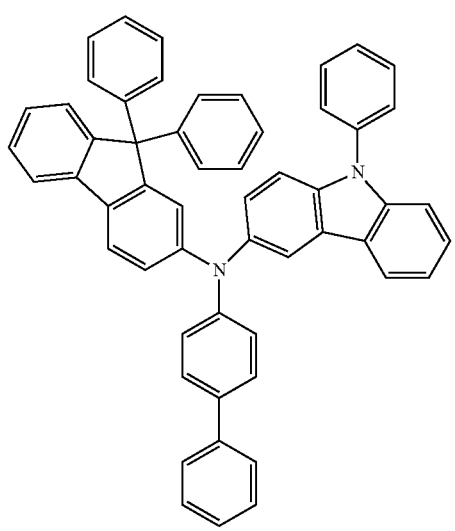
59
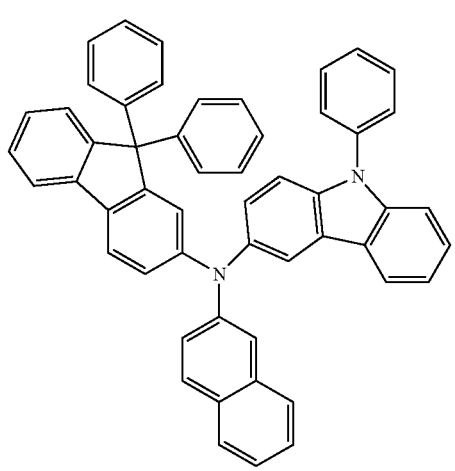

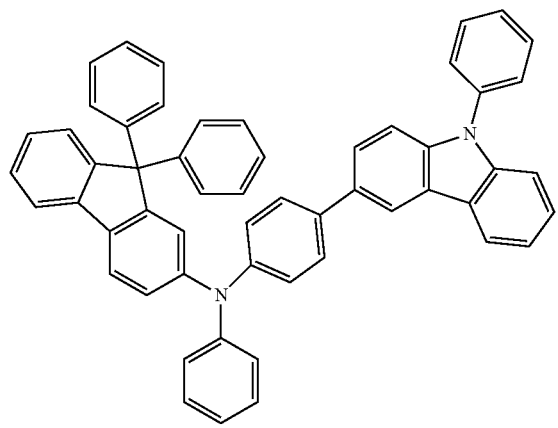

60

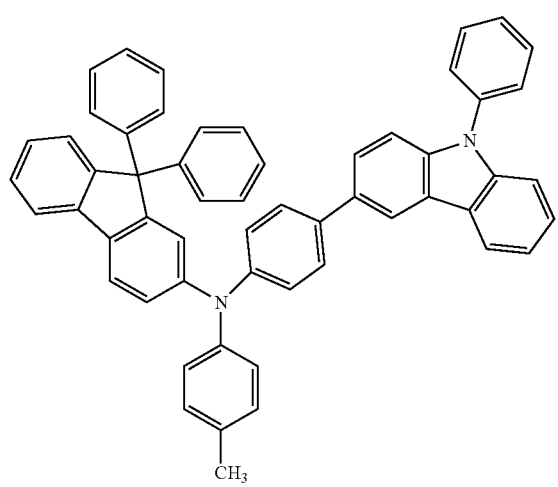

61

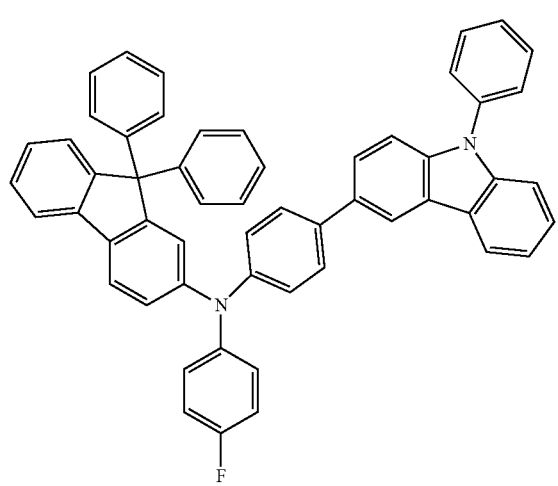

62

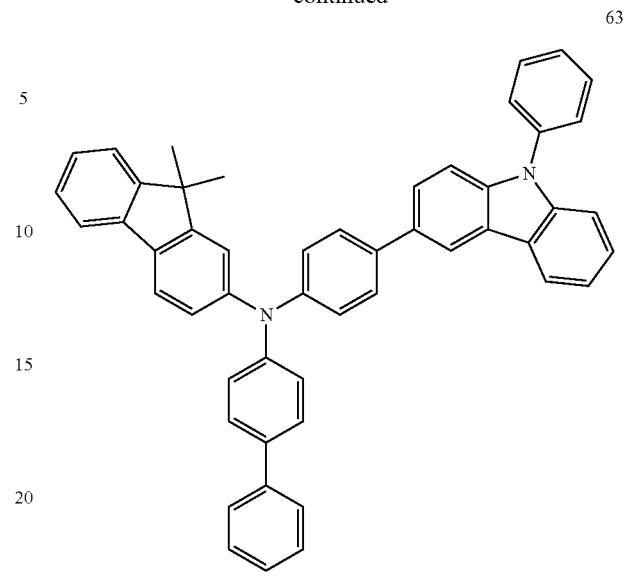

63

The compound represented by the general formula (Sa-1), (Sb-1), or (Sc-1) can be synthesized by the method described in JP-A-2007-318101. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the light emitting element of the present invention, the compound represented by the general formula (Sa-1), (Sb-1), or (Sc-1) is preferably included in the organic layer between the light emitting layer and the anode, and among these, it is more preferably included in the layer on the anode side adjacent to the light emitting layer, and it is particularly preferably a hole transporting material included in the hole transporting layer.

The compound represented by the general formula (Sa-1), (Sb-1), or (Sc-1) is preferably contained in the amount of 70 to 100% by mass, and more preferably 85 to 100% by mass, based on the total mass of the organic layer added.

Compound Represented by General Formula (M-3)

The organic electroluminescent element of the present invention is a material which is particularly preferably used in an organic layer, preferably disposed between the (A) anode and the light emitting layer, and examples thereof include at least one kind of the compound represented by the following general formula (M-3).

The compound represented by the general formula (M-3) is more preferably contained in the organic layer adjacent to the light emitting layer between the light emitting layer and the anode, but it is not limited in its uses and may be further contained in any of other layers in the organic layer. The layer to which the compound represented by the general formula (M-3) is introduced may be any one or plural layers of a light emitting layer, a hole injecting layer, a hole transporting layer, an electron transporting layer, an electron injecting layer, and a charge blocking layer.

The organic layer adjacent to the light emitting layer between the light emitting layer and the anode, which contains the compound represented by the general formula (M-3), is more preferably an electron blocking layer or a hole transporting layer.

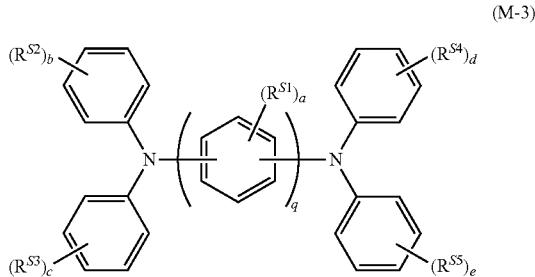

(M-3)

In the general formula (M-3), $R^{S1}$ to $R^{S5}$ each independently represent an alkyl group, a cycloalkyl group, an alkenyl group, an alkynyl group, —CN, a perfluoroalkyl group, a trifluorovinyl group, —$CO_2R$, —C(O)R, —$NR^2$, —$NO_2$, —OR, a halogen atom, an aryl group, or an heteroaryl group, and may also have a substituent Z. R's each independently represent a hydrogen atom, an alkyl group, a perhaloalkyl group, an alkenyl group, an alkynyl group, a heteroalkyl group, an aryl group, or a heteroaryl group. When plural $R^{S1}$'s to $R^{S5}$'s are present, they may be bonded to each other to form a ring and further have a substituent Z.

a represents an integer of 0 to 4, and when plural $R^{S1}$'s are present, they may be the same as or different from each other and may be bonded to each other to form a ring. b to e each independently represent an integer of 0 to 5, and when each of plural $R^{S2}$'s to $R^{S5}$'s are present, they may be the same as or different from each other, and any two out of them may be bonded to each other to form a ring.

q is an integer of 1 to 5, and when q is 2 or more, the plural $R^{S1}$'s may be the same as or different from each other, and may be bonded to each other to form a ring.

The alkyl group may have a substituent and may be saturated or unsaturated. Examples of the group which may be used for substitution include the above-described substituents Z. Examples of the alkyl group represented by $R^{S1}$ to $R^{S5}$ preferably include alkyl groups having 1 to 8 carbon atoms in total, and more preferably alkyl groups having 1 to 6 carbon atoms in total, for example, a methyl group, an ethyl group, an i-propyl group, a cyclohexyl group, and a t-butyl group.

The cycloalkyl group may have a substituent, and may be saturated or unsaturated. Examples of the group which may be used for substitution include the above-described substituents Z. Examples of the cycloalkyl group represented by $R^{S1}$ to $R^{S5}$ preferably include cycloalkyl groups having a number of the ring members of 4 to 7, and more preferably cycloalkyl groups having 5 to 6 carbon atoms in total, for example, a cyclopentyl group and a cyclohexyl group.

Examples of the alkenyl group represented by $R^{S1}$ to $R^{S5}$ include ones preferably having 2 to 30 carbon atoms, more preferably 2 to 20 carbon atoms, and particularly preferably 2 to 10 carbon atoms, for example, vinyl, allyl, 1-propenyl, 1-isopropenyl, 1-butenyl, 2-butenyl, and 3-pentenyl.

Examples of the alkynyl group represented by $R^{S1}$ to $R^{S5}$ include ones preferably having 2 to 30 carbon atoms, more preferably 2 to 20 carbon atoms, and particularly preferably 2 to 10 carbon atoms, for example, ethynyl, propargyl, 1-propynyl, and 3-pentynyl.

Examples of the perfluoroalkyl group represented by $R^{S1}$ to $R^{S5}$ include those in which all the hydrogen atoms of the above-described alkyl group are substituted with fluorine atoms.

Preferred examples of the aryl group represented by $R^{S1}$ to $R^{S5}$ include a substituted or unsubstituted aryl group having 6 to 30 carbon atoms, for example, a phenyl group, a tolyl group, a biphenyl group, a terphenyl group.

The heteroaryl group represented by $R^{S1}$ to $R^{S5}$ is preferably a heteroaryl group having 5 to 8 carbon atoms, and more preferably a 5- or 6-membered substituted or unsubstituted heteroaryl group, and examples thereof include a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a triazolyl group, a benzothiazolyl group, an isothiazolyl group, a benzisothiazolyl group, a thiadiazolyl group, an isoxazolyl group, a benzisoxazolyl group, a pyrrolidinyl, piperidinyl group, a piperadinyl group, an imidazolidinyl group, a thiazolinyl group, a sulfolanyl group, a carbazolyl group, a dibenzofuryl group, a dibenzothienyl group, and a pyridindolyl group. Preferred examples thereof include a pyridyl group, a pyrimidinyl group, an imidazolyl group, and a thienyl group, and more preferably a pyridyl group and a pyrimidinyl group.

$R^{S1}$ to $R^{S5}$ are preferably a hydrogen atom, an alkyl group, a cyano group, a trifluoromethyl group, a perfluoroalkyl group, a dialkylamino group, a fluoro group, an aryl group, a heteroaryl group, more preferably a hydrogen atom, an alkyl group, a cyano group, a trifluoromethyl group, a fluoro group, and an aryl group, and still more preferably a hydrogen atom, an alkyl group, and an aryl group. As the substituent Z, an alkyl group, an alkoxy group, a fluoro group, a cyano group, and a dialkylamino group are preferred, and a hydrogen atom and an alkyl group are more preferred.

Any two of $R^{S1}$ to $R^{S5}$ may be bonded to form a fused 4- to 7-membered ring, and the fused 4- to 7-membered ring is cycloalkyl, aryl, or heteroaryl, and the fused 4- to 7-membered ring may further have a substituent Z. The definitions and preferred ranges of the cycloalkyl, aryl, and heteroaryl thus formed are the same as for the cycloalkyl group, the aryl group, and the heteroaryl group defined by $R^{S1}$ to $R^{S5}$.

In a case where the compound represented by the general formula (M-3) is used in a hole transporting layer, the compound represented by the general formula (M-3) is preferably contained in the amount of 50 to 100% by mass, more preferably 80 to 100% by mass, and particularly preferably 95 to 100% by mass.

In addition, in a case where the compound represented by the general formula (M-3) is used in plural organic layers, the compound is preferably contained in an amount of the above-described range in each layer.

The thickness of the hole transporting layer including the compound represented by the general formula (M-3) is preferably from 1 nm to 500 nm, more preferably from 3 nm to 200 nm, and still more preferably from 5 nm to 100 nm. Further, the hole transporting layer is preferably provided to be adjacent to the light emitting layer.

Specific examples of the compound represented by the general formula (M-3) are shown below, but the present invention is not limited thereto.

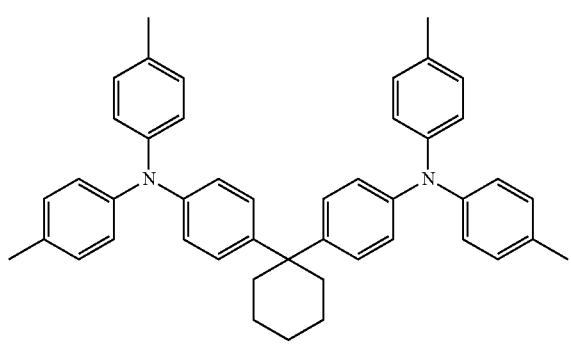
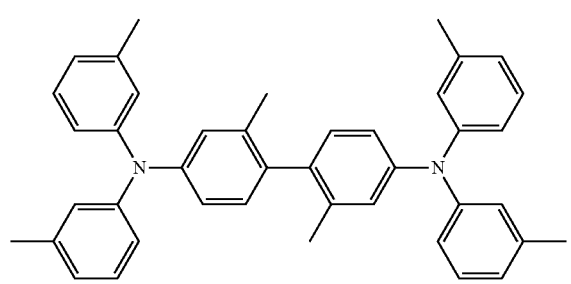
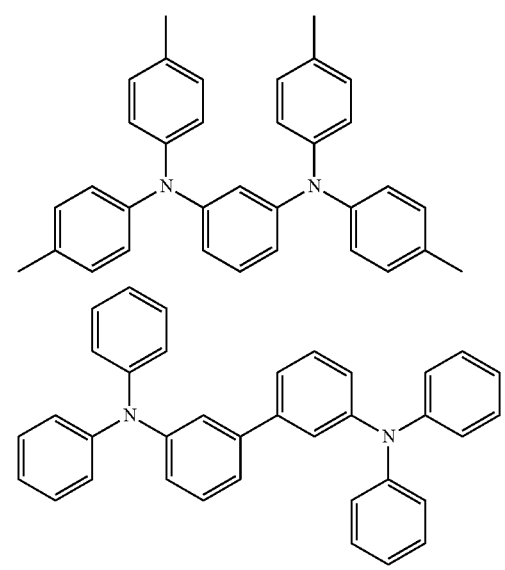
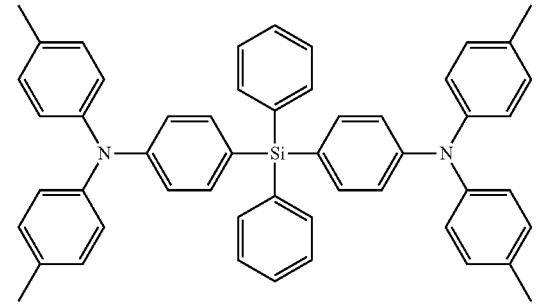
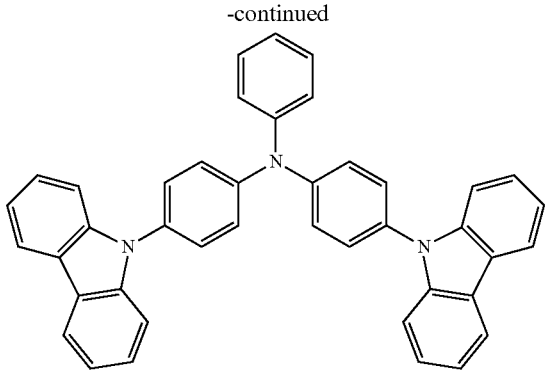
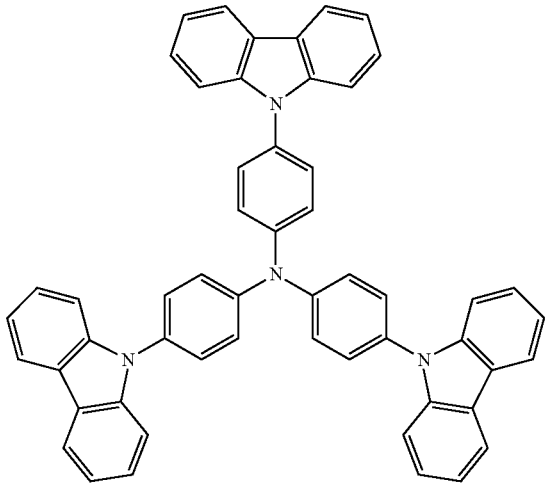
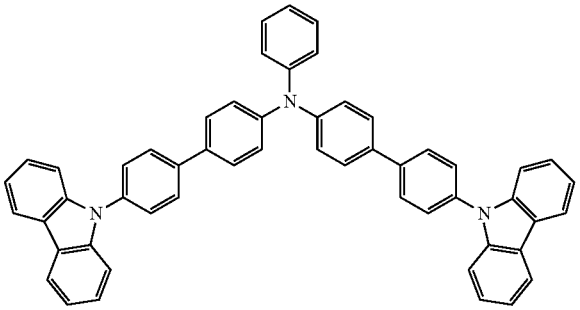
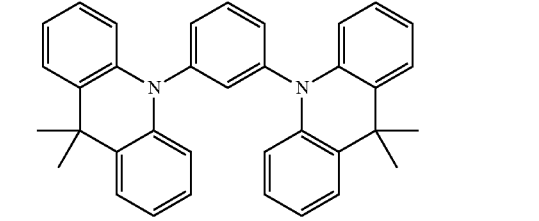
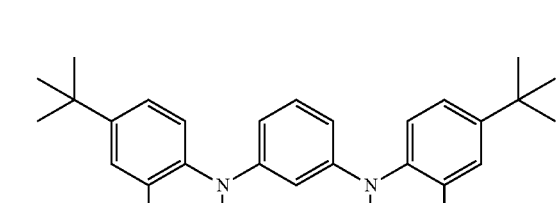

97
-continued
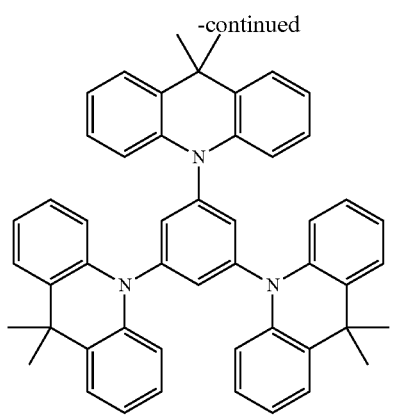
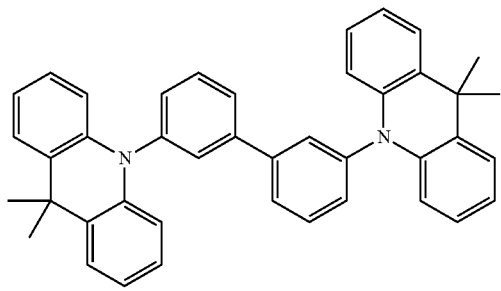
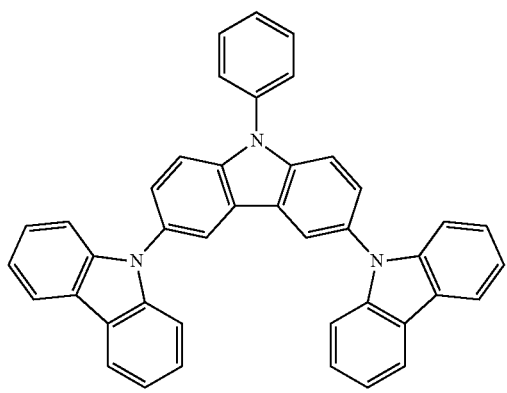
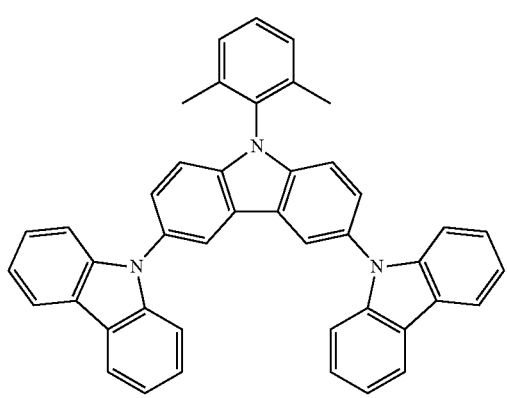
98
-continued
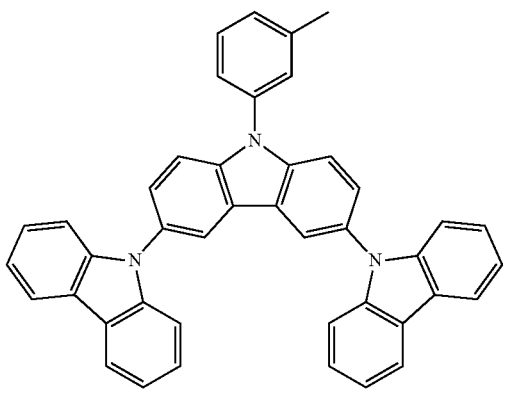
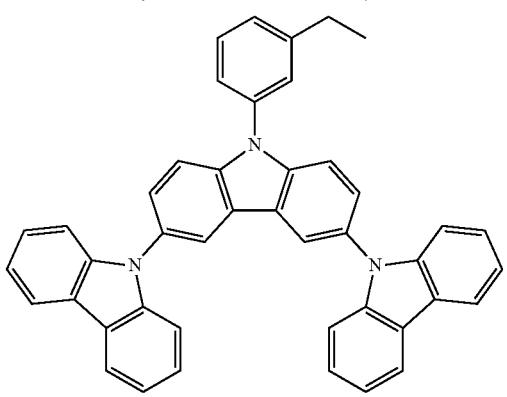
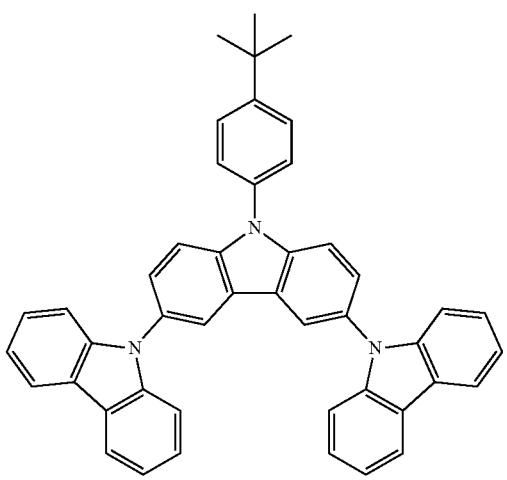
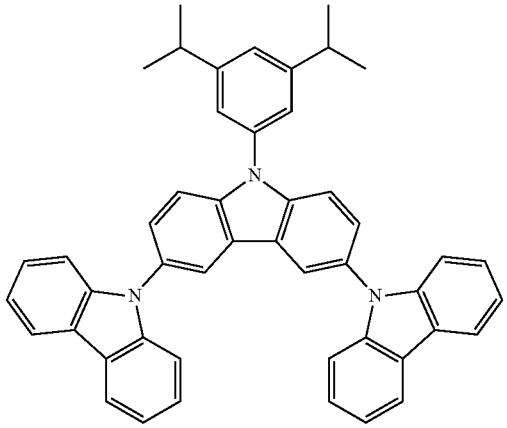

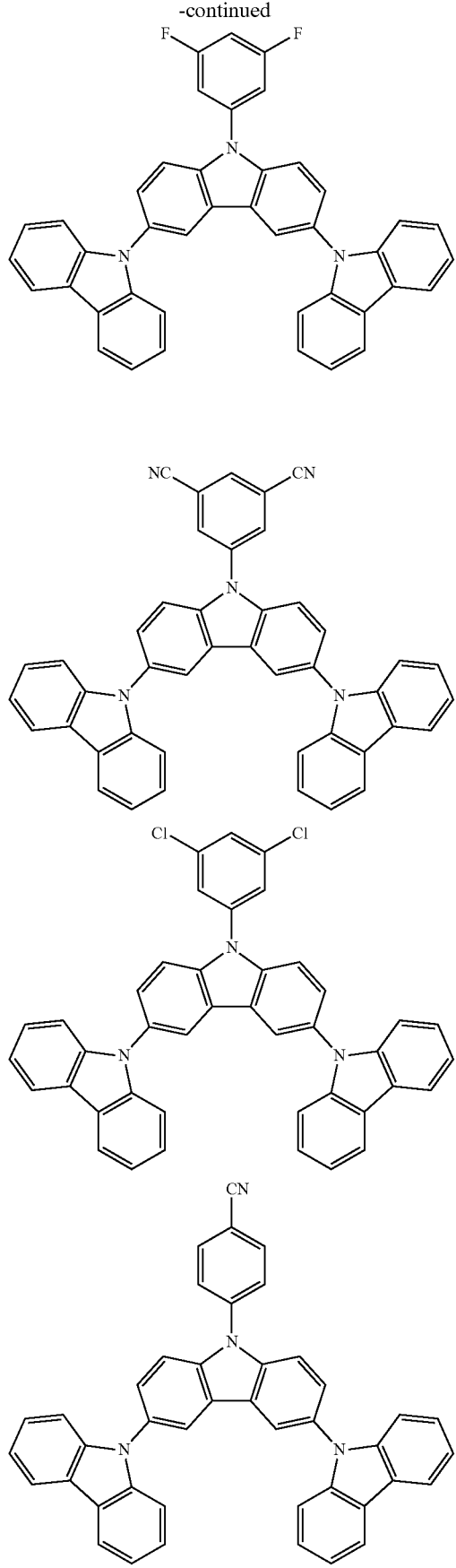
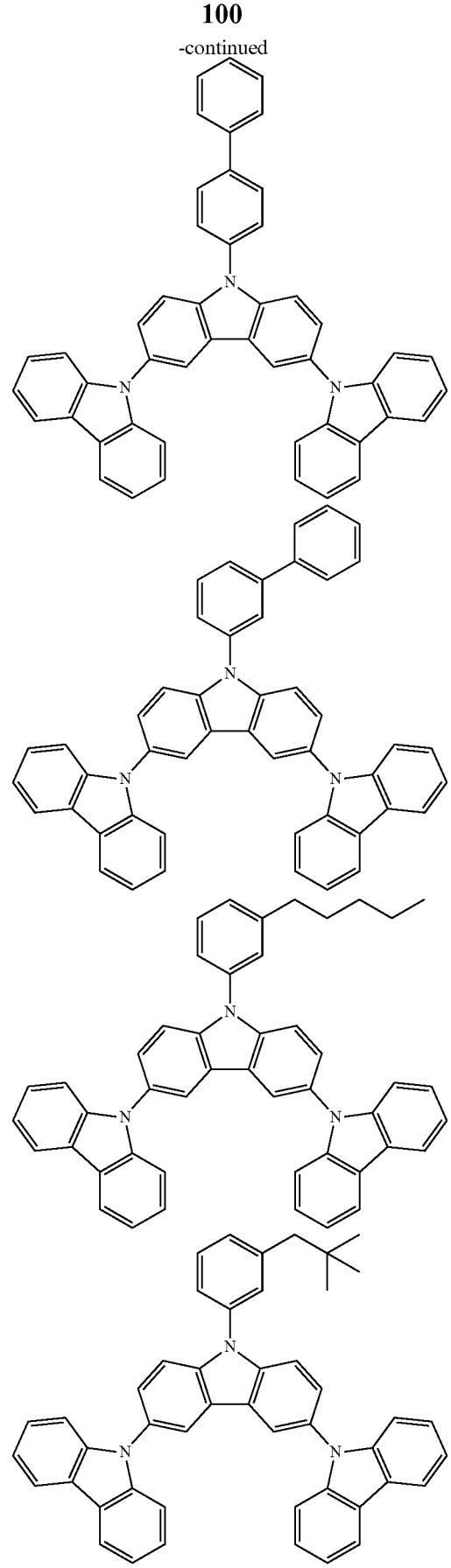

101
-continued
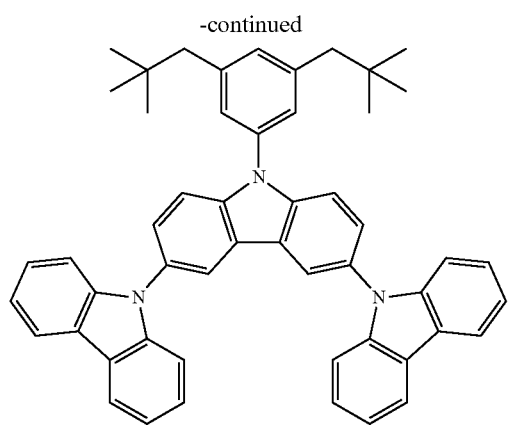
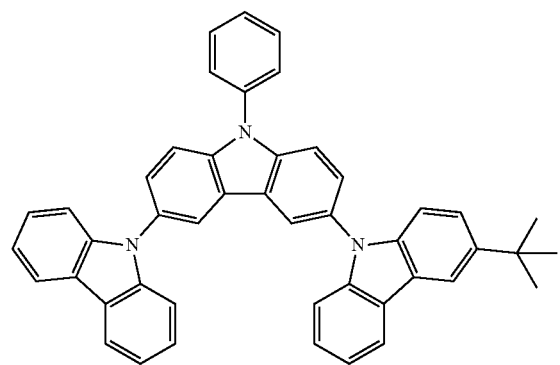
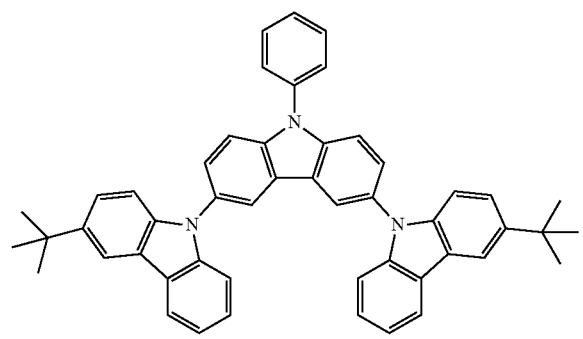
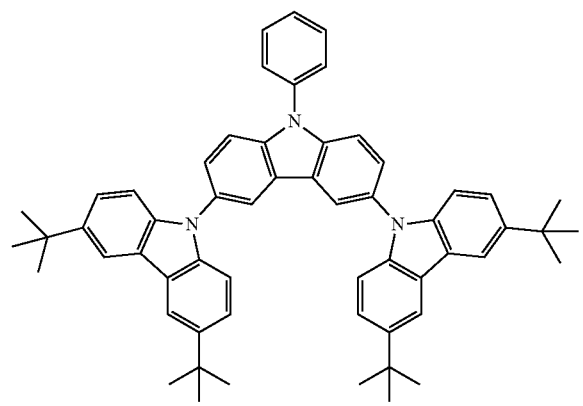
102
-continued
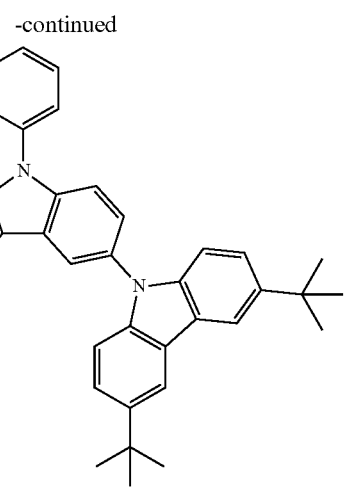
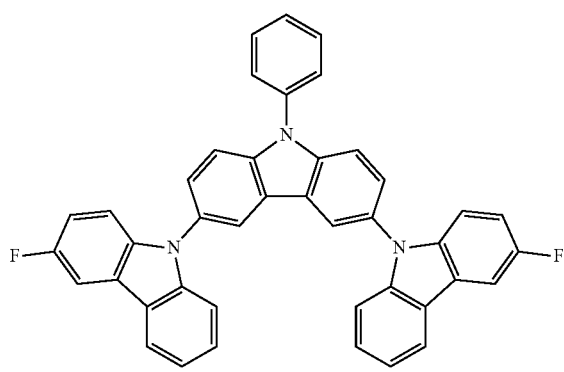
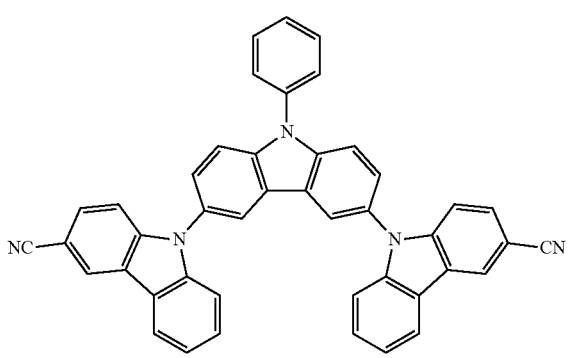
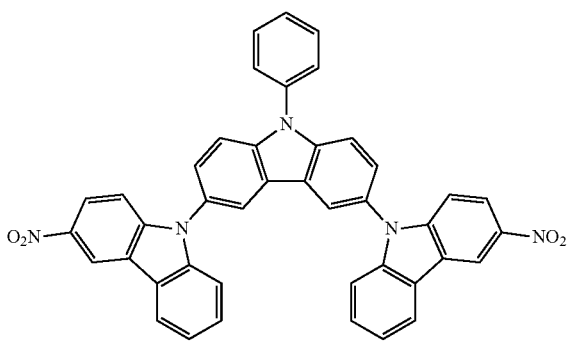

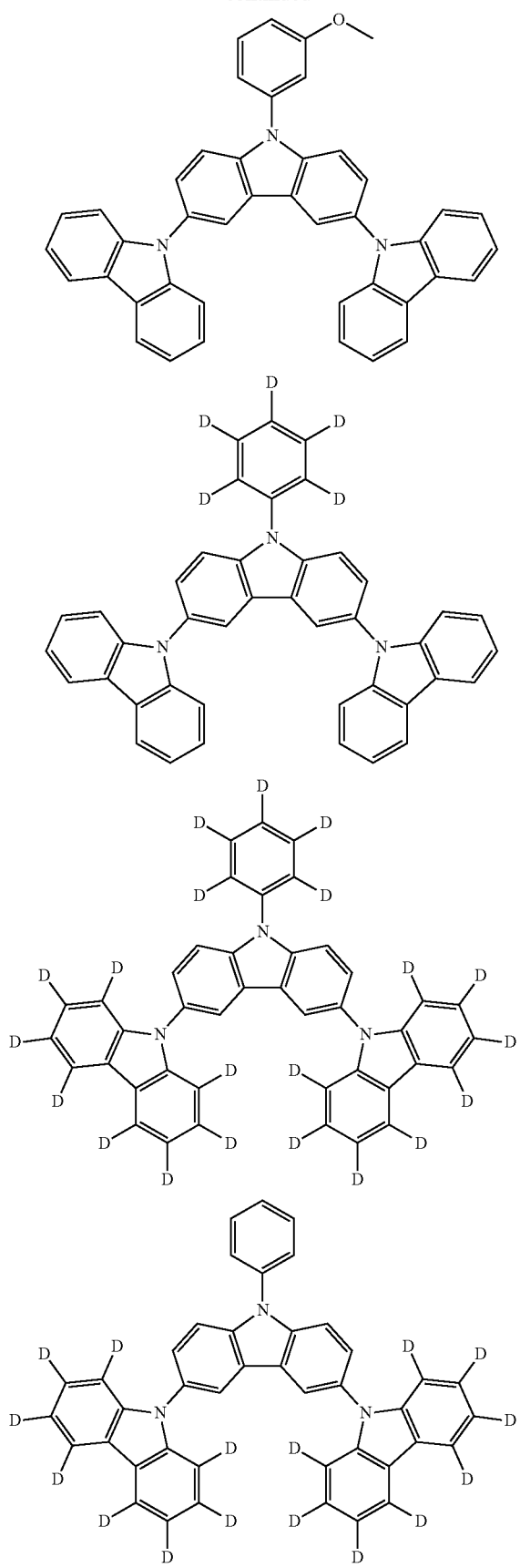
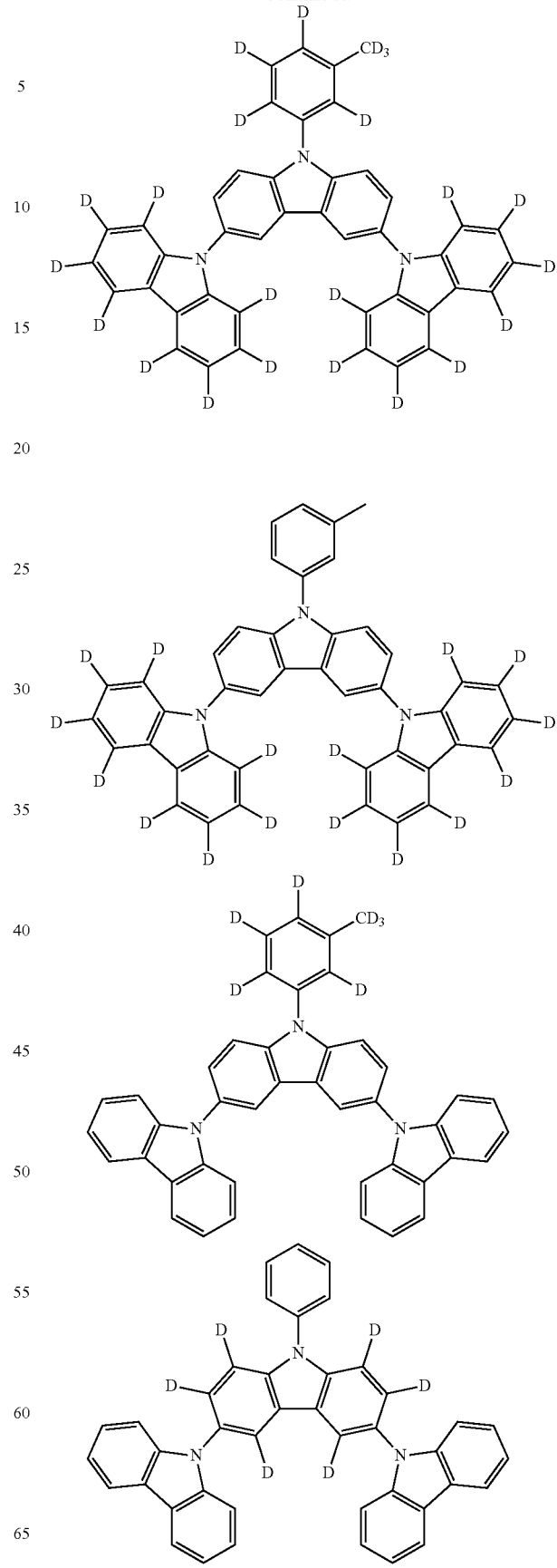

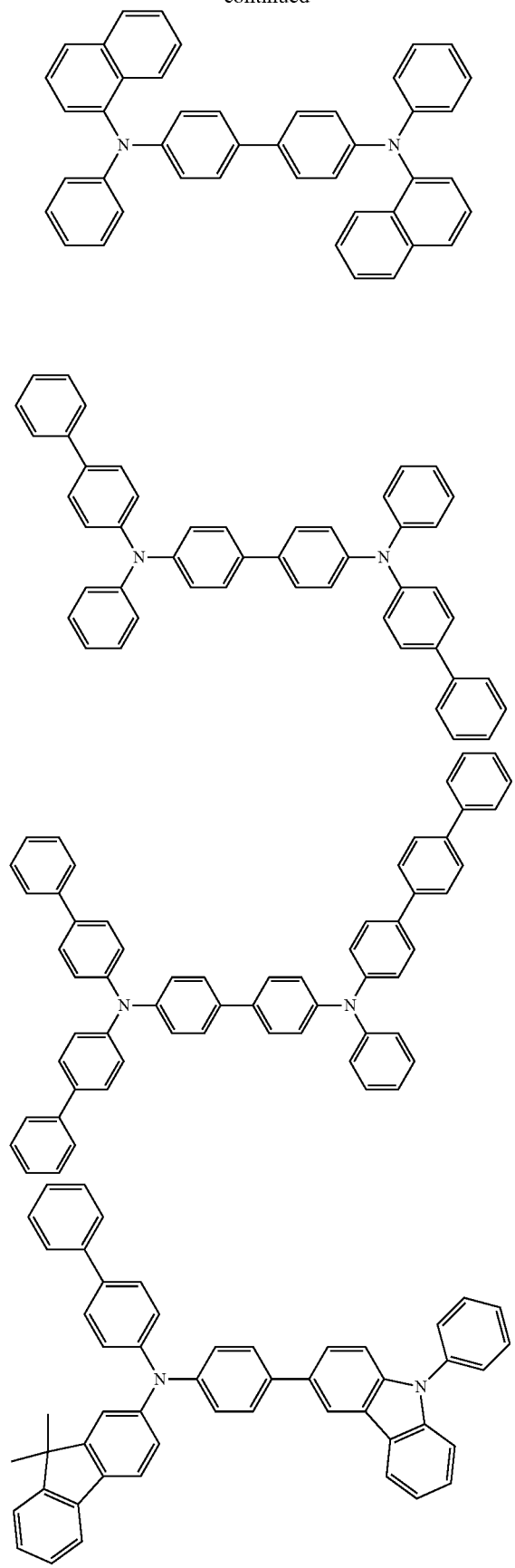
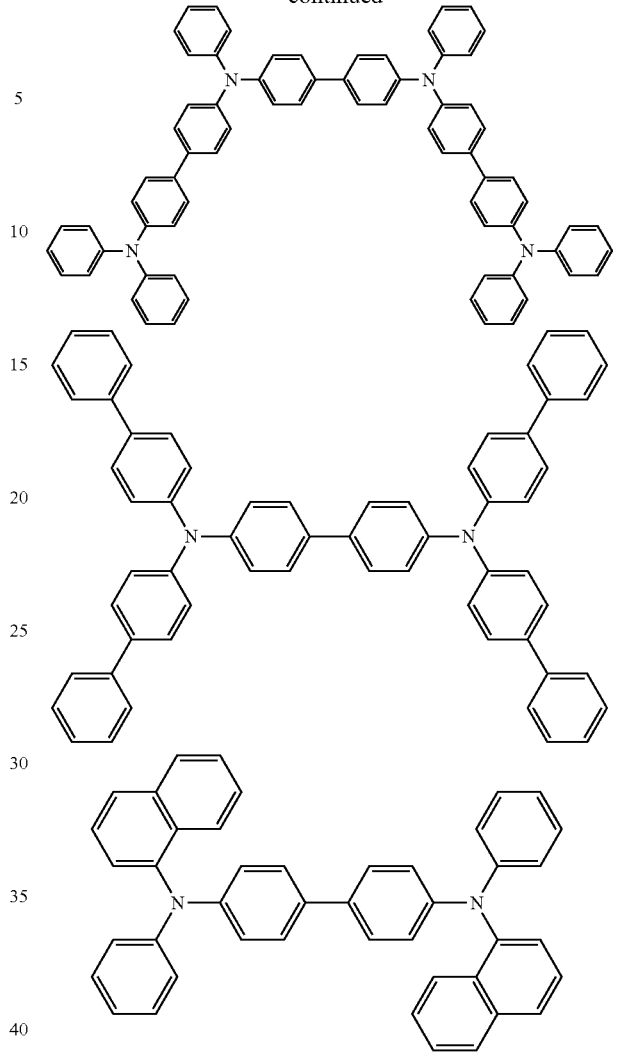

In addition, the detailed description on the hole injecting layer and the hole transporting layer in Paragraph Nos. [0165] to [0167] of JP-A-2008-270736 can also be applied to the present invention. Further, the detailed description in [0250] to [0339] of JP-A-2011-71452 can also be applied to the hole injecting layer and the hole transporting layer of the present invention.

The hole injecting layer preferably contains an electron receptive dopant. By incorporating the electron receptive dopant in the hole injecting layer, there are effects in which, for example, the hole injecting properties are improved, the driving voltage is lowered, and the efficiency is improved. The electron receptive dopant may be any one of organic materials and inorganic materials as long as it is capable of withdrawing electrons from doped material and generating radical cations, and examples thereof include tetracyanoquinodimethane (TCNQ) and TCNQ compounds such as tetrafluorotetracyanoquinodimethane ($F_4$-TCNQ), hexaazatriphenylene compounds such as hexacyanohexaazatriphenylene (HAT-CN, compound LG 101 used in the Examples below), and molybdenum oxide.

The electron receptive dopant in the hole injecting layer is preferably contained in the amount of 0.01 to 50% by mass, more preferably 0.1 to 40% by mass, and still more preferably 0.2 to 30% by mass, based on the total mass of the compounds forming the hole injecting layer.

(A-2) Electron Blocking Layer

The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer on the anode side.

As the organic compound constituting the electron blocking layer, those exemplified above as the hole transporting materials can be used.

The thickness of the electron blocking layer is preferably from 1 nm to 500 nm, more preferably from 3 nm to 100 nm, and still more preferably from 5 nm to 50 nm.

The electron blocking layer may have either a single layer structure composed of one or more materials selected from the above-exemplified materials or a multilayer structure composed of a plurality of layers having the same composition or different compositions.

The material used in the electron blocking layer preferably has higher $S_1$ energy than that of the light emitting material in views of color purity, luminous efficiency, and driving durability. The $S_1$ in the film state of the material used in the electron blocking layer is preferably higher than the $S_1$ of the light emitting material by 0.1 eV or more, more preferably by 0.2 eV or more, and still more preferably by 0.3 eV or more.

(B) Organic Layer Preferably Disposed Between Cathode and Light Emitting Layer

First, the (B) organic layer preferably disposed between the cathode and the light emitting layer will be described.

(B-1) Electron Injecting Layer and Electron Transporting Layer

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, for example, the compound represented by the general formula (1) can be used. As the other electron transporting materials, any one selected from aromatic ring tetracarboxylic acid anhydrides, such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof, organic silane derivatives typified by silol, hydrocarbon compounds with fused rings, such as naphthalene, anthracene, phenanthrene, triphenylene, and pyrene is preferred, and any one selected from pyridine derivatives, benzimidazole derivatives, imidazopyridine derivatives, metal complexes, and hydrocarbon compounds with fused rings is more preferred.

The thickness of each of the electron injecting layer and the electron transporting layer is preferably 500 nm or less from the viewpoint that the driving voltage is decreased.

The thickness of the electron transporting layer is preferably from 1 nm to 500 nm, more preferably from 5 nm to 200 nm, and still more preferably from 10 nm to 100 nm. The thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one or more materials selected from the above-exemplified materials or a multilayer structure composed of a plurality of layers having the same composition or different compositions.

The electron injecting layer preferably contains an electron donating dopant. By incorporating the electron donating dopant in the electron injecting layer, there are effects that, for example, the electron injecting properties are improved, the driving voltage is lowered, and the efficiency is improved. The electron donating dopant may be any one of organic materials and inorganic materials as long as it is capable of giving electrons to the material to be doped and generating radical anions, and examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is preferably contained in the amount of 0.01 to 50% by mass, more preferably 0.1 to 40% by mass, and still more preferably 0.5 to 30% by mass, based on the total mass of the compounds forming the electron injecting layer.

(B-2) Hole Blocking Layer

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order that the $S_1$ energy of the organic compound in the film state constituting the hole blocking layer prevents the energy movement of excitons produced in the light emitting layer, and thus, does not lower the luminous efficiency, it is preferably higher than $S_1$ energy of the light emitting material.

As one example of the organic compound constituting the hole blocking layer, for example, the compound represented by the general formula (1) can be used.

Examples of the organic compounds constituting the hole blocking layer, other than the compound represented by the general formula (1), include aluminum complexes such as aluminum (III) bis(2-methyl-8-quinolinato) 4-phenylphenolate (abbreviated as "BAlq"), triazole derivatives, and phenanthroline derivatives such as 2,9-dimethyl-4,7-diphenyl-1,10-phenanthroline (abbreviated as "BCP").

The thickness of the hole blocking layer is preferably from 1 nm to 500 nm, more preferably from 3 nm to 100 nm, and still more preferably from 5 nm to 50 nm.

The hole blocking layer may have either a single layer structure composed of one or more materials selected from the above-exemplified materials or a multilayer structure composed of a plurality of layers having the same composition or different compositions.

The material used in the hole blocking layer preferably has higher $S_1$ energy than that of the light emitting material in views of color purity, luminous efficiency, and driving durability. The $S_1$ in the film state of the material used in the hole blocking layer is preferably higher than the $S_1$ of the light emitting material by 0.1 eV or more, more preferably by 0.2 eV or more, and still more preferably by 0.3 eV or more.

(B-3) Material which is Particularly Preferably Used in Organic Layer, Preferably Disposed Between Cathode and Light Emitting Layer For the organic electroluminescent element of the present invention, examples of the material which is particularly preferably used in the materials for an organic layer, preferably disposed between the (B) cathode and the light emitting layer include the compound represented by the general formula (1), a compound represented by the following general formula (P-1), and a compound represented by the following general formula (O-1).

Hereinafter, a compound represented by the general formula (O-1) and a compound represented by the general formula (P-1) will be described.

The organic electroluminescent element of the present invention preferably includes at least one layer of organic layers between the light emitting layer and the cathode, and the organic layer preferably contains at least one of compounds represented by the following general formula (O-1), from the viewpoint of efficiency or driving voltage of an element. Hereinafter, the general formula (O-1) will be described.

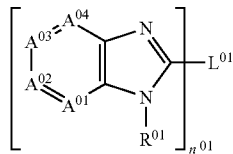

General Formula (O-1)

(In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and plural $R^A$'s may be the same as or different from each other. $L^{O1}$ represents any of divalent to hexavalent linking groups with an aryl ring or a heteroaryl ring. $n^{O1}$ represents an integer of 2 to 6).

$R^{O1}$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $R^{O1}$ is preferably an aryl group or a heteroaryl group, and more preferably an aryl group. Preferred examples of the substituent in a case where the aryl group of $R^{O1}$ has a substituent include an alkyl group, an aryl group, and a cyano group, more preferably an alkyl group and an aryl group, and still more preferably an aryl group. In a case where the aryl group of $R^{O1}$ has plural substituents, the plural substituents may be bonded to each other to form a 5- or 6-membered ring. The aryl group of $R^{O1}$ is preferably a phenyl group which may have a substituent selected from Substituent Group A, more preferably a phenyl group which may be substituted with an alkyl group or an aryl group, and still more preferably an unsubstituted phenyl group or 2-phenylphenyl group.

$A^{O1}$ to $A^{O4}$ each independently represent C—$R^A$ or a nitrogen atom. It is preferable that 0 to 2 out of $A^{O1}$ to $A^{O4}$ be nitrogen atoms; and it is more preferable that 0 or 1 out of $A^{O1}$ to $A^{O4}$ be nitrogen atoms. It is preferable that all of $A^{O1}$ to $A^{O4}$ be C—$R^A$, or $A^{O1}$ is a nitrogen atom, and $A^{O2}$ to $A^{O4}$ are C—$R^A$; it is more preferable that $A^{O1}$ is a nitrogen atom, and $A^{O2}$ to $A^{O4}$ are C—$R^A$; it is still more preferable that $A^{O1}$ is a nitrogen atom, $A^{O2}$ to $A^{O4}$ are C—$R^A$, and $R^A$'s are all hydrogen atoms.

$R^A$ represents a hydrogen atom, an alkyl group (preferably having 1 to 8 carbon atoms), an aryl group (preferably having 6 to 30 carbon atoms), or a heteroaryl group (preferably having 4 to 12 carbon atoms), and may have a substituent selected from the above-described Substituent Group A. Further, plural $R^A$'s may be the same as or different from each other. $R^A$ is preferably a hydrogen atom or an alkyl group, and more preferably a hydrogen atom.

$L^{O1}$ represents a divalent to hexavalent linking group including an aryl ring (preferably having 6 to 30 carbon atoms) or a heteroaryl ring (preferably having 4 to 12 carbon atoms). $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have a substituent selected from the above-described Substituent Group A, and in a case of having the substituent, the substituent is preferably an alkyl group, an aryl group, or a cyano group. Specific examples of $L^{O1}$ include the following.

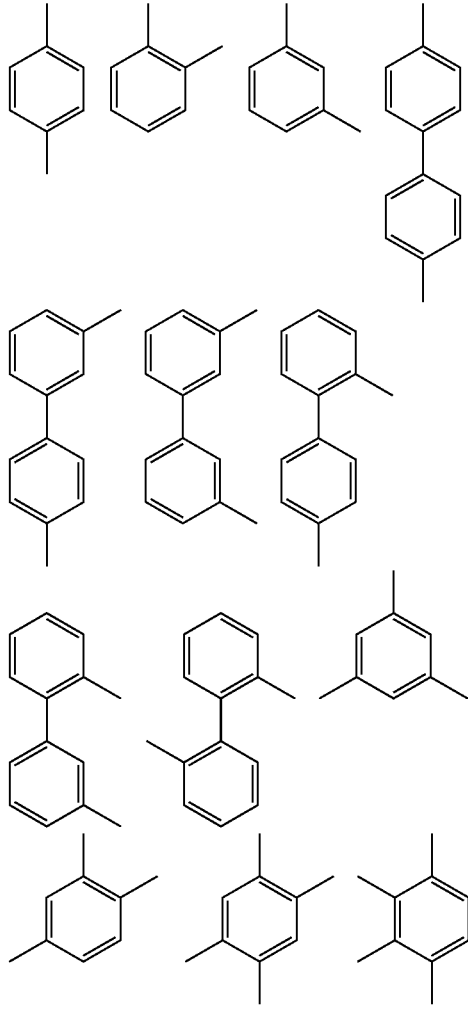

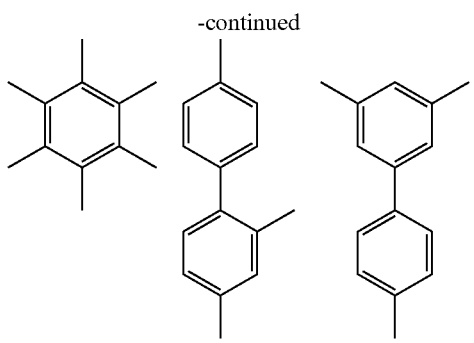
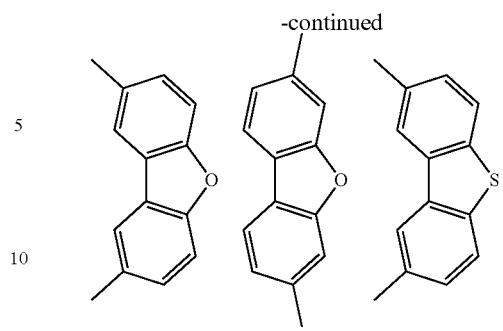
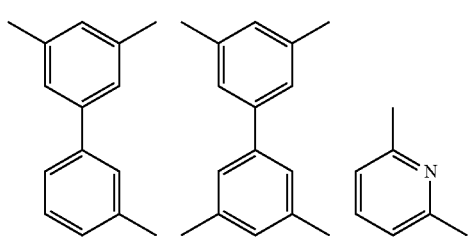
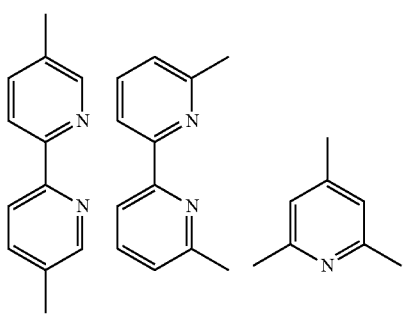
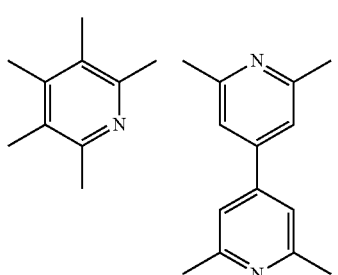
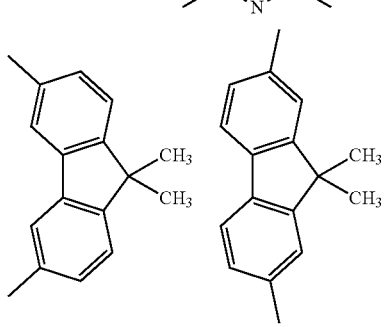

$n^{O1}$ represents an integer of 2 to 6, preferably an integer of 2 to 4, and more preferably 2 or 3. $n^{O1}$ is most preferably 3 from the viewpoint of the efficiency of an element, or most preferably 2 from the viewpoint of the durability of an element.

The glass transition temperature (Tg) of the compound represented by the general formula (O-1) is preferably from 100° C. to 300° C., more preferably from 120° C. to 300° C., still more preferably from 120° C. to 300° C., and even still more preferably from 140° C. to 300° C., from the viewpoint of stability during storage at a high temperature, or stable operation during driving at a high temperature or against heat generation during driving.

Specific examples of the compound represented by the general formula (O-1) are shown below, but the compound represented by the general formula (O-1), which can be used in the present invention, should not be construed to be limited to the specific examples.

113
OM-1
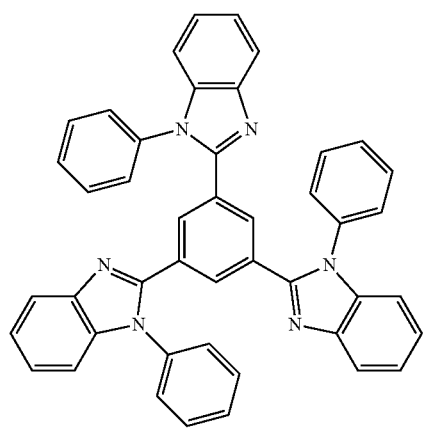
114
OM-2
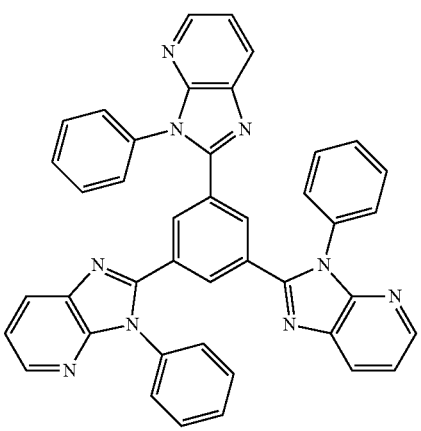
OM-3
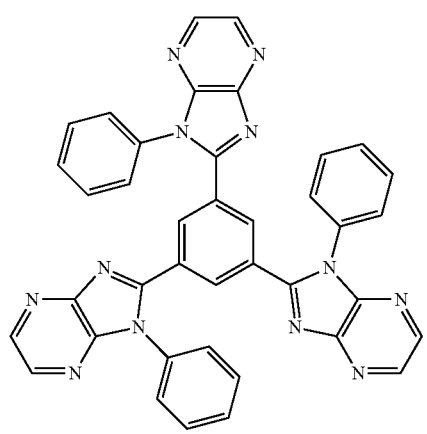
OM-4
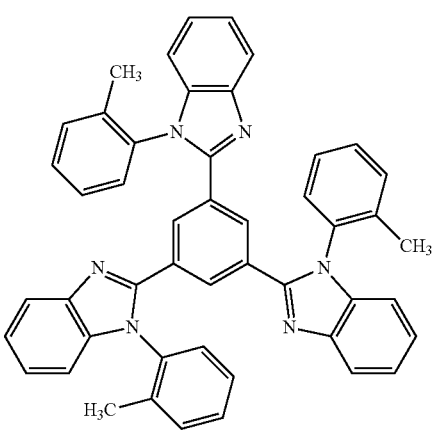
OM-5
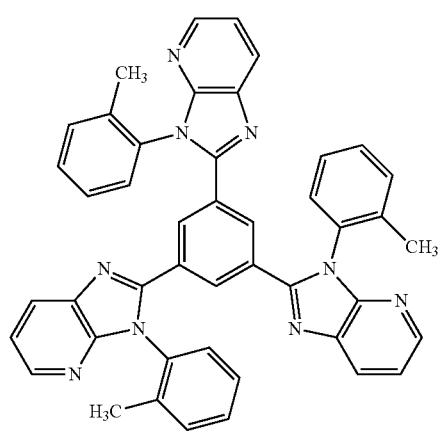
OM-6
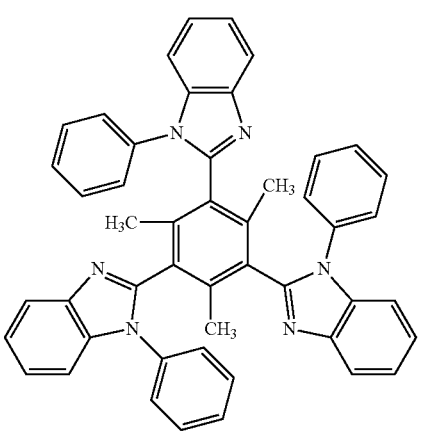

-continued
OM-7
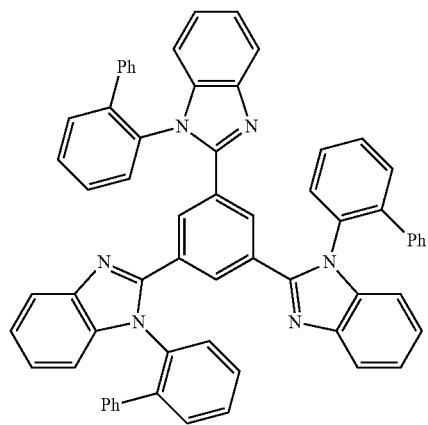
OM-8
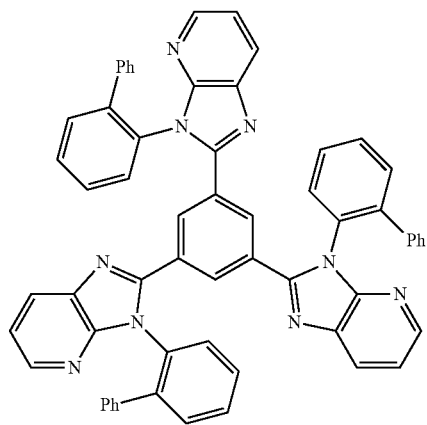
OM-9
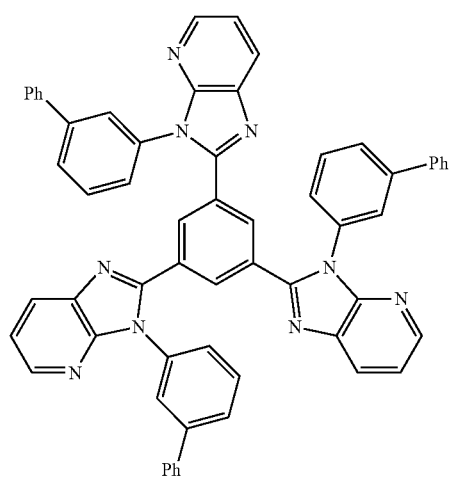
OM-10
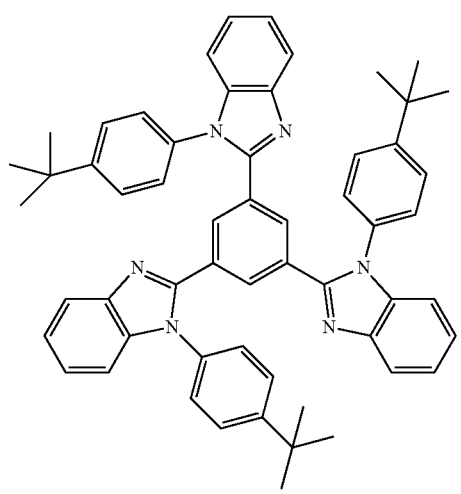
OM-11
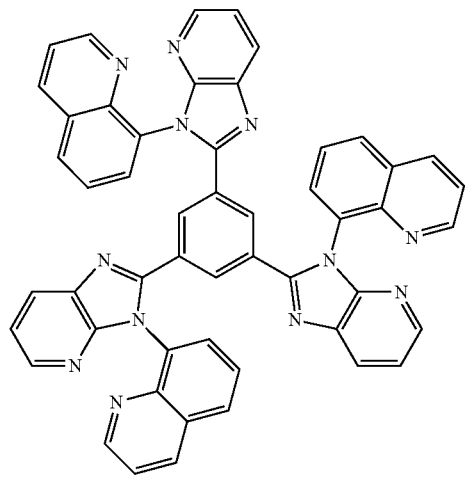
OM-12
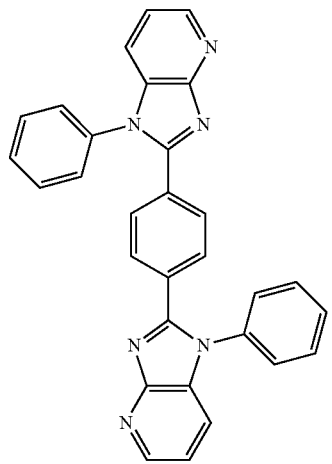

-continued
OM-13
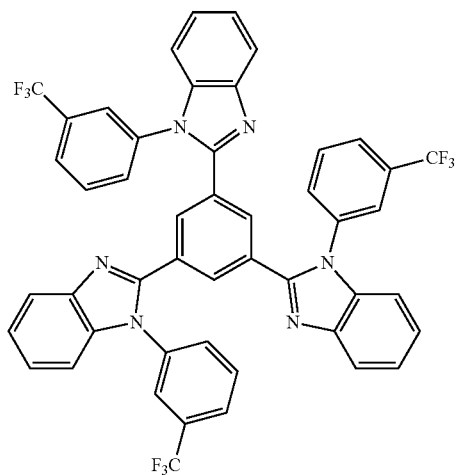
OM-14
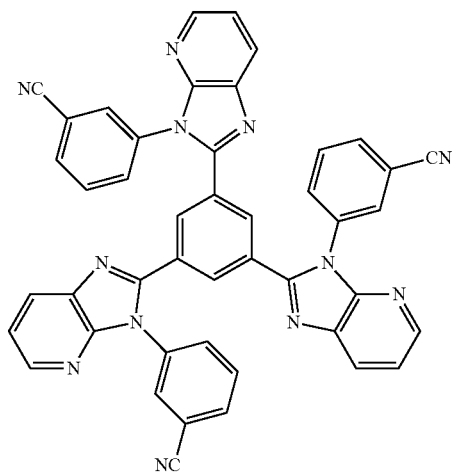
OM-15
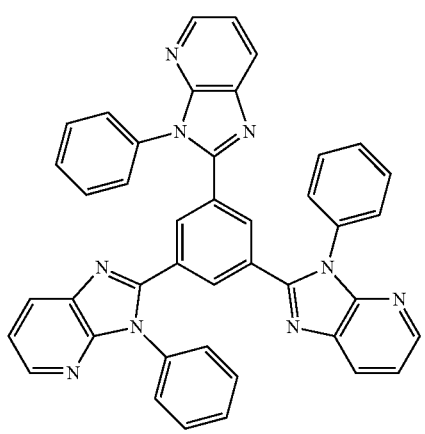
OM-16
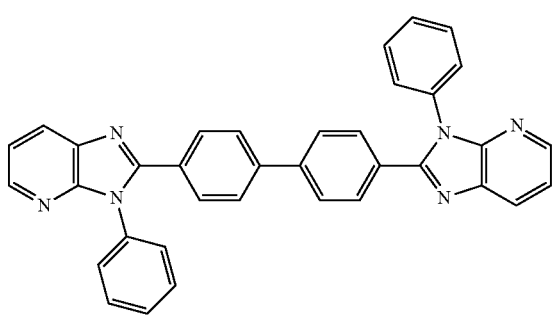
OM-17
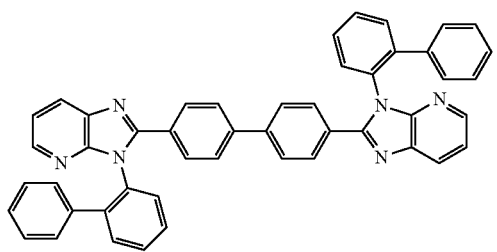
OM-18
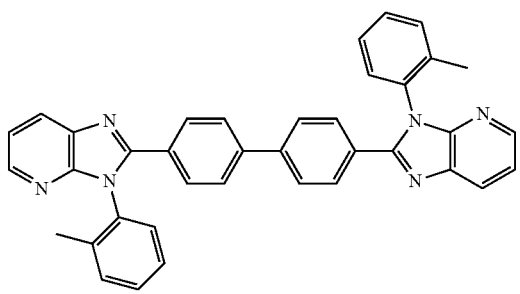
OM-19
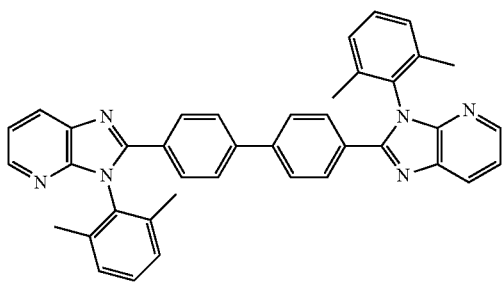
OM-20
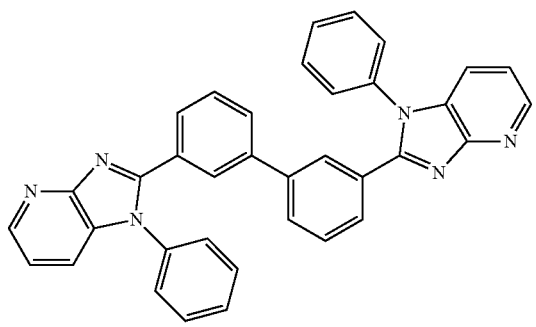

OM-21

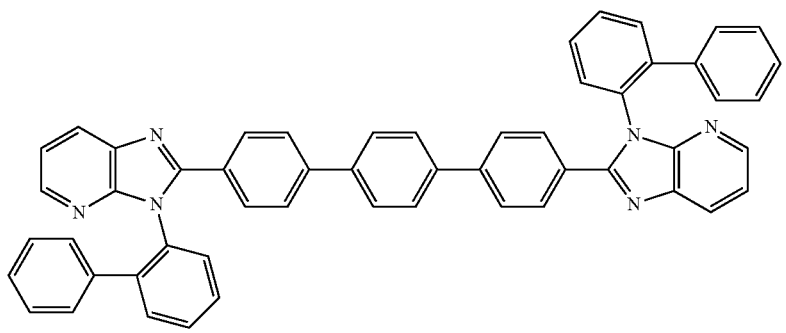

OM-22

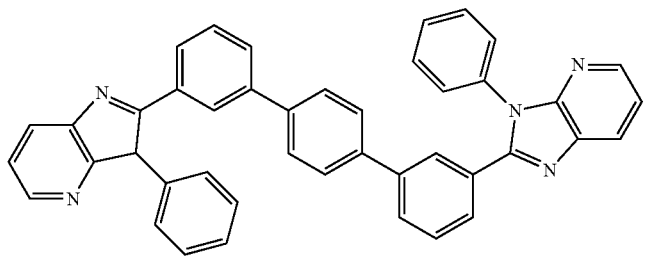

The compound represented by the general formula (O-1) can be synthesized by the method described in JP-A-2001-335776. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (O-1) is preferably included in the organic layer between the light emitting layer and the cathode, however, it is more preferably included in the layer on the cathode side adjacent to the light emitting layer.

The compound represented by the general formula (O-1) is preferably contained in the amount of 70 to 100% by mass, and more preferably 85 to 100% by mass, based on the total mass of the organic layer added.

The organic electroluminescent element of the present invention preferably includes at least one layer of organic layers between the light emitting layer and the cathode, and it is preferable that the organic layer contain at least one of compounds represented by the following general formula (P), from the viewpoint of efficiency or the driving voltage of an element. Hereinafter, the general formula (P) will be described.

General Formula (P)

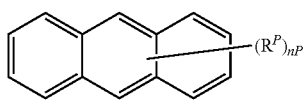

(In the general formula (P), $R^P$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. nP represents an integer of 1 to 10, and in a case where there are plural $R^P$s, these may be the same as or different from each other. At least one of $R^P$s is a substituent represented by the following general formulae (P-1) to (P-3).

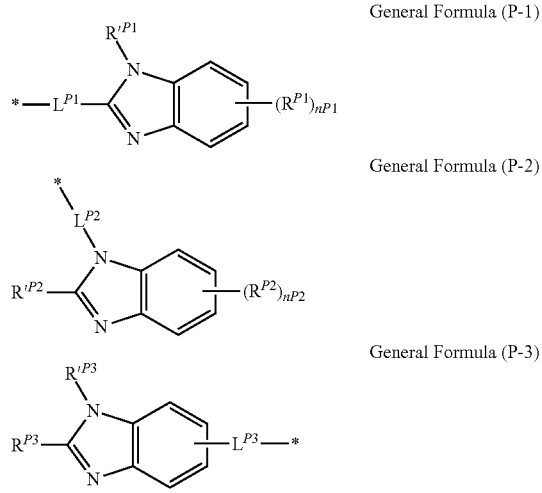

(In the general formulae (P-1) to (P-3), $R^{P1}$ to $R^{P3}$ and $R^{\prime P1}$ to $R^{\prime P3}$ each represent an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $n^{P1}$ and $n^{P2}$ represent an integer of 0 to 4, and in a case where there are a plurality of $R^{P1}$ to $R^{P3}$ and $R^{\prime P1}$ to $R^{\prime P3}$, these may be the same as or different from each other. $L^{P1}$ to $L^{P3}$ represent any one of divalent linking groups consisting of a single bond, an aryl ring, or a heteroaryl ring. * represents a binding position with the anthracene ring of the general formula (P)).

A preferred substituent other than the substituents represented by (P-1) to (P-3) as $R^P$ is an aryl group, more preferably any one of a phenyl group, a biphenyl group, a terphenyl group, and a naphthyl group, and still more preferably a naphthyl group.

$R^{P1}$ to $R^{P3}$ and $R^{tP1}$ to $R^{tP3}$ are preferably any one of an aryl group and a heteroaryl group, more preferably an aryl group, still more preferably any one of a phenyl group, a biphenyl group, a terphenyl group, and a naphthyl group, and most preferably a phenyl group.

$L^{P1}$ to $L^{P3}$ are preferably any one of divalent linking groups consisting of a single bond and an aryl ring, more preferably any one of a single bond, phenylene, biphenylene, terphenylene, and naphthylene, still more preferably any one of a single bond, phenylene, and naphthylene.

Specific examples of the compound represented by the general formula (P) are shown below, but the compound represented by the general formula (P) that can be used in the present invention should not be construed to be limited to the specific examples.

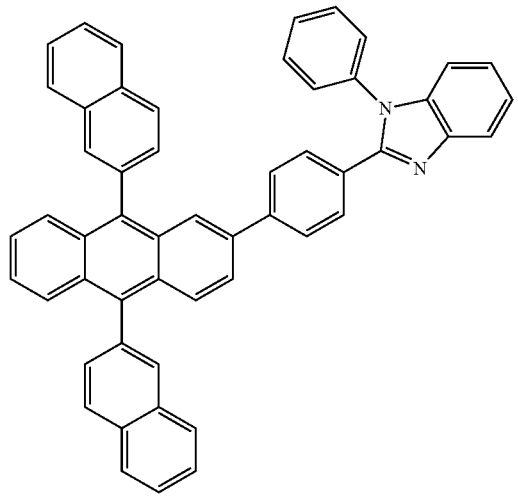

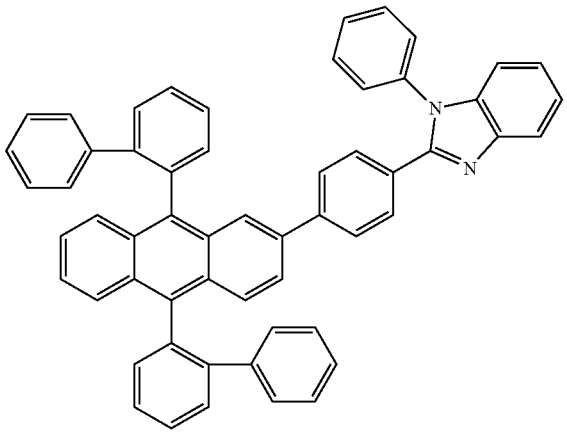

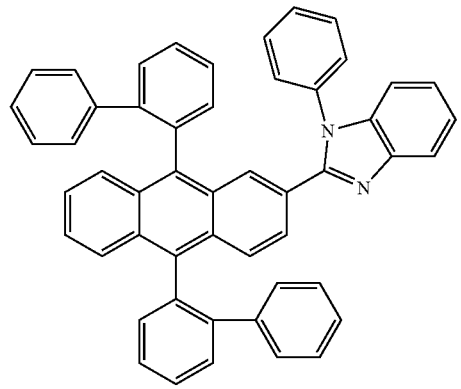

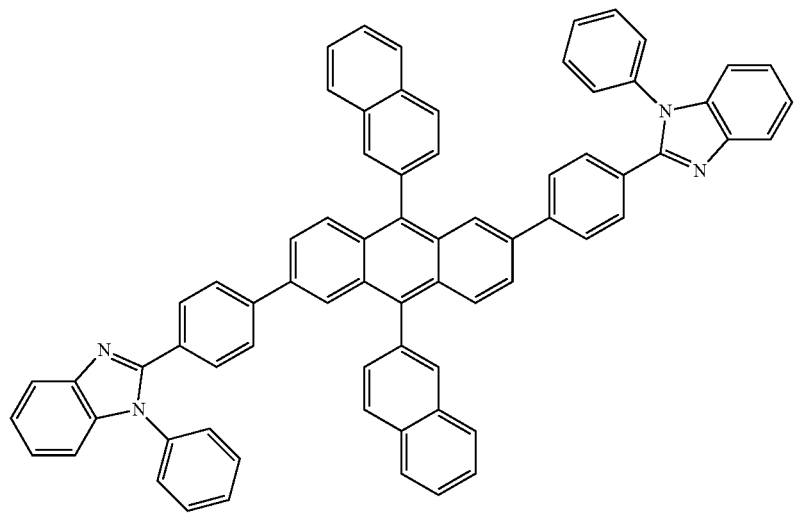

-continued
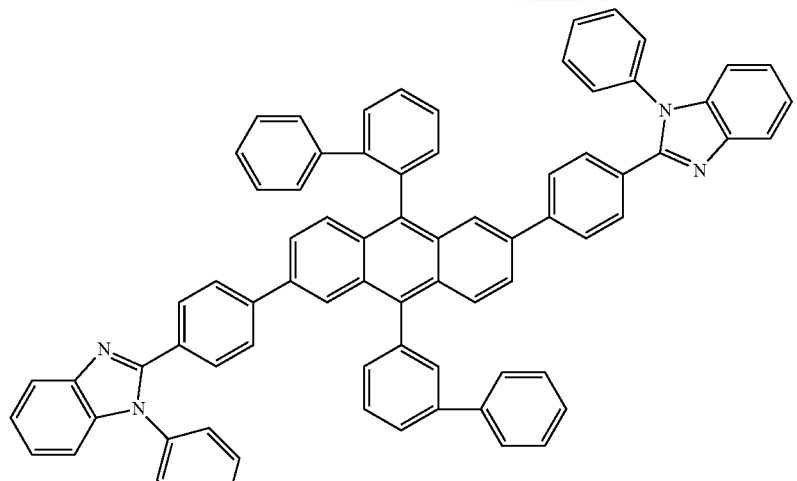
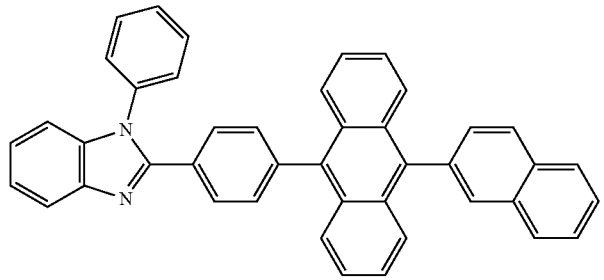
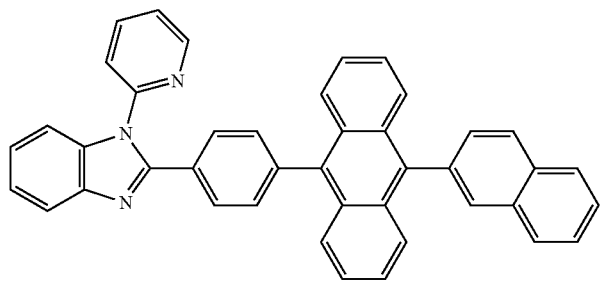
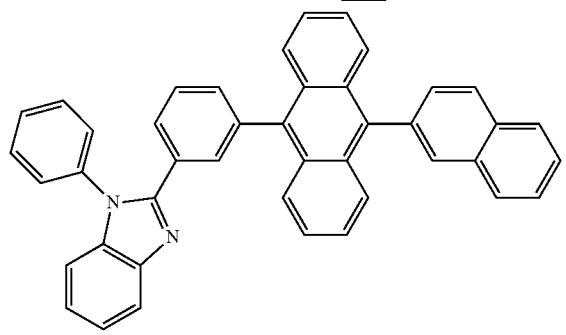
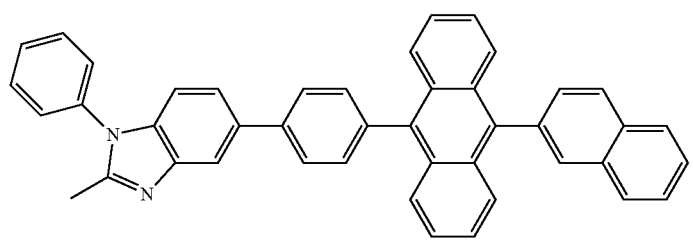

-continued

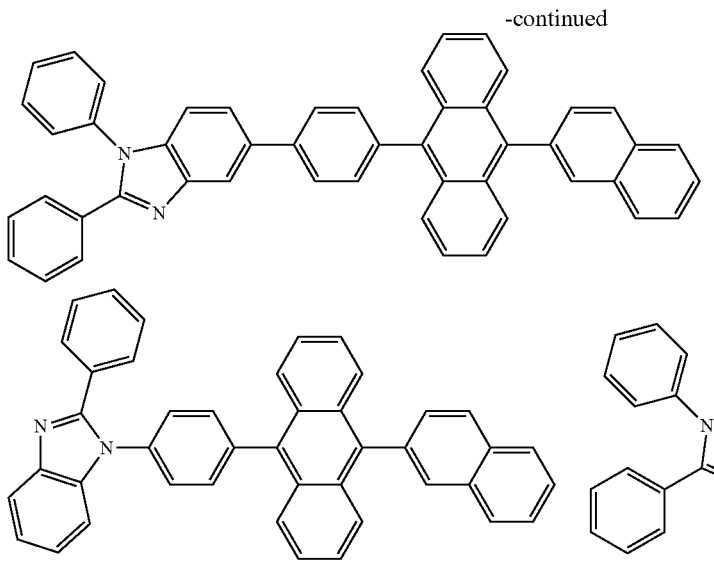

The compound represented by the general formula (P) can be synthesized by the method described in WO 2003/060956 and WO 2004/080975. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (P) is preferably included in the organic layer between the light emitting layer and the cathode, and more preferably in the layer adjacent to the cathode.

The compound represented by the general formula (P) is preferably contained in the amount of 70 to 100% by mass, and more preferably 85 to 100% by mass, based on the total mass of the organic layer added.

Preferred examples of the material other than the material used in the electron injecting layer or the electron transporting layer in the organic electroluminescent element of the present invention include silole compounds described in JP-A-09-194487 or the like, phosphineoxide compounds described in JP-A-2006-73581 or the like, nitrogen-containing aromatic 6-membered ring hetero compounds described in JP-A-2005-276801, JP-A-2006-225320, WO 2005/085387, or the like, compounds having nitrogen-containing aromatic 6-membered hetero structures and carbazole structures, described in WO 2003/080760, WO 2005/085387, or the like, and aromatic hydrocarbon compounds described in US2009/0009065, WO2010/134350, Japanese PCT National Publication No. 2010-535806 (naphthalene compounds, anthracene compounds, triphenylene compounds, phenanthrene compounds, pyrene compounds, fluoranthene compounds, and the like).

Protective Layer

In the present invention, the entirety of the organic electric element may be protected with a protective layer.

For the protective layer, the detailed description in, for example, in Paragraph Nos. [0169] to [0170] of JP-A-2008-270736 can also be applied to the present invention. Further, the materials for the protective layer may be either inorganic materials or organic materials.

Sealing Enclosure

For the organic electroluminescent element of the present invention, the entirety of the element may be sealed with a sealing enclosure.

For the sealing enclosure, the detailed description in Paragraph No. [0171] of JP-A-2008-270736 can be applied to the present invention.

Driving Method

The organic electroluminescent element of the present invention can emit light by applying a direct current (it may contain an alternate current component, if necessary) voltage (typically, from 2 volts to 15 volts) or a direct current between the anode and the cathode.

As a driving method of the organic electroluminescent element of the present invention, driving methods described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element of the present invention is preferably 5% or more, more preferably 6% or more, and more preferably 7% or more. As to the numerical value of the external quantum efficiency, a maximum value of the external quantum efficiency obtained when the organic electroluminescent element is driven at 20° C., or a value of the external quantum efficiency in the vicinity of from 300 to 400 cd/m$^2$ obtained when the element is driven at 20° C. can be employed.

The internal quantum efficiency of the organic electroluminescent element of the present invention is preferably 30% or more, more preferably 50% or more, and still more preferably 70% or more. The internal quantum efficiency of the element is calculated by dividing the external quantum efficiency by the light extraction efficiency. The light extraction efficiency in usual organic EL elements is about 20%, but by taking into consideration the shape of a substrate, the shape of an electrode, the thickness of an organic layer, the thickness of an inorganic layer, the refractive index of an organic layer, the refractive index of an inorganic layer, or the like, it is possible to increase the light extraction efficiency to 20% or more.

Light Emitting Wavelength

The light emitting wavelength of the organic electroluminescent element of the present invention is the same as the maximum luminous wavelength of the material for the organic electroluminescent element of the present invention, and is used for the emission of the blue light in the three primary colors of light. In the organic electroluminescent element of the present invention, the compounds represented by the general formula (1) are used as light emitting material to emit blue light.

Use of Organic Electroluminescent Element of the Present Invention

The organic electroluminescent element of the present invention can be suitably used for display elements, displays, backlights, electrophotography, illumination light sources, recording light sources, exposure light sources, readout light sources, signs, billboards, interior decorations, optical communications, and the like, and particularly preferably for devices driven in a region of high-intensity luminescence, such as a light emitting device, an illumination device, and a display device.

Light Emitting Device

The light emitting device of the present invention may include the organic electroluminescent element of the present invention.

Next, the light emitting device of the present invention will be described with reference to FIG. 2.

The light emitting device of the present invention is formed by using the organic electroluminescent element.

Figure 2:
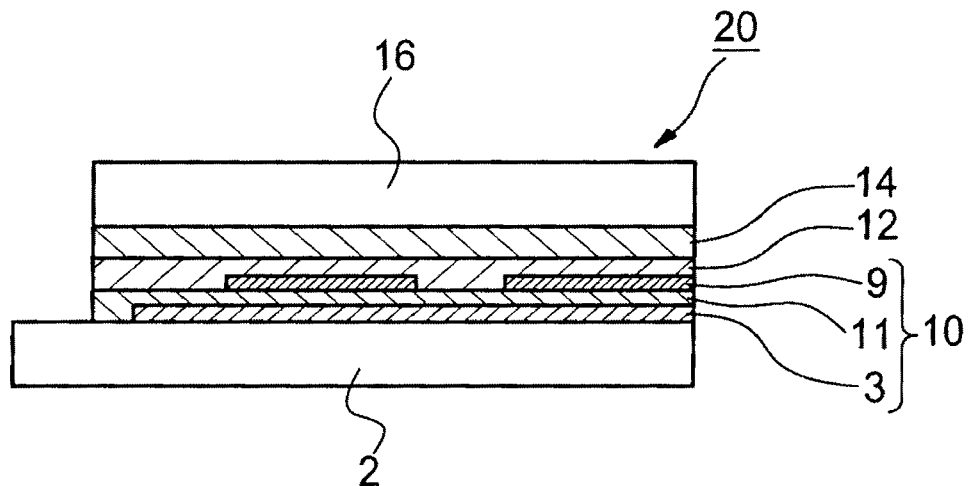
FIG. 2 is a schematic view showing one example of a light emitting device according to the present invention.

FIG. 2 is a cross-sectional view schematically showing one example of the light emitting device of the present invention. The light emitting device 20 in FIG. 2 includes a transparent substrate 2 (supporting substrate), an organic electroluminescent element 10, a sealing enclosure 16, and the like.

The organic electroluminescent element 10 is formed by laminating on the substrate 2 an anode 3 (first electrode), an organic layer 11, and a cathode 9 (second electrode) in this order. In addition, a protective layer 12 is laminated on the cathode 9, and on the protective layer 12 a sealing enclosure 16 is further provided via an adhesive layer 14. Incidentally, a part of each of the electrodes 3 and 9, a diaphragm, an insulating layer, and the like are omitted in FIG. 2.

Herein, a photocurable adhesive such as an epoxy resin, or a thermosetting adhesive can be used for the adhesive layer 14, and for example, a thermosetting adhesive sheet may also be used as the adhesive layer 14.

The light emitting device of the present invention is not particularly limited in its use, and it can be used as not only an illumination device but also a display device of a television set, a personal computer, a mobile phone, electronic paper, or the like.

Illumination Device

The illumination device of the present invention includes the organic electroluminescent element of the present invention.

Next, the illumination device of the present invention will be described with reference to FIG. 3.

Figure 3:
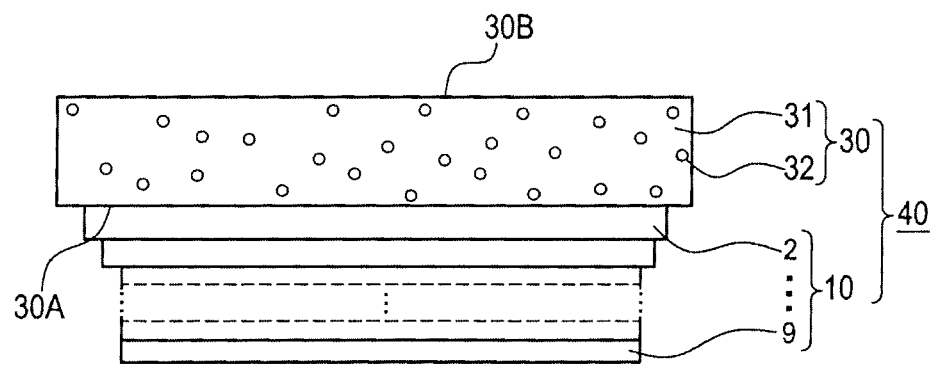
FIG. 3 is a schematic view showing one example of an illumination device according to the present invention.

FIG. 3 is a cross-sectional view schematically showing one example of the illumination device of the present invention. The illumination device 40 of the present invention includes, as shown in FIG. 3, the above-described organic EL element 10 and a light scattering member 30. More specifically, the illumination device 40 is configured such that the substrate 2 of the organic EL element 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is incident on the light incident surface 30A of the scattering member 30, the incident light is scattered by the light scattering member 30 and the scattered light is output as illuminating light from the light output surface 30B.

Display Device

The display device of the present invention includes the organic electroluminescent element of the present invention.

The display device of the present invention can be used for, for example, a display device of a television set, a personal computer, a mobile phone, electronic paper, or the like.

EXAMPLES

Hereinbelow, the features of the present invention will be described in more detail with reference to Examples and Comparative Examples. The materials, use amounts, ratios, process details, process sequences, and the like shown in Examples below may be appropriately modified without departing from the spirit of the present invention. Accordingly, the scope of the present invention should not be construed to be limited to the specific examples shown below.

The structural formulae of the compounds used in Examples and Comparative Examples are summarized below.

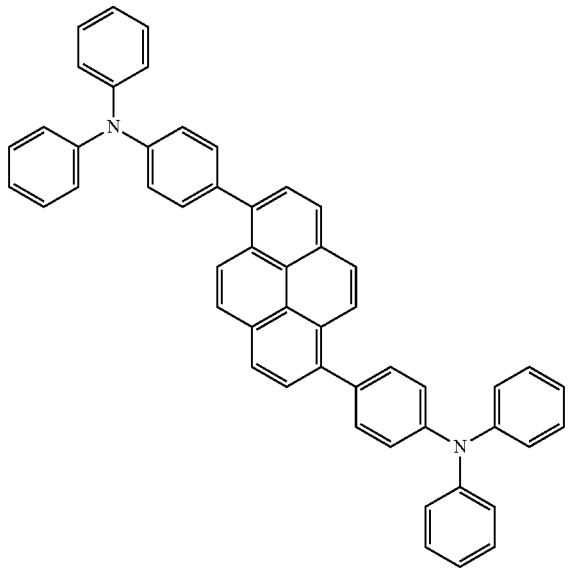

Comparative compound 1

Compound of JP-A-2006-298793

-continued
Comparative compound 2
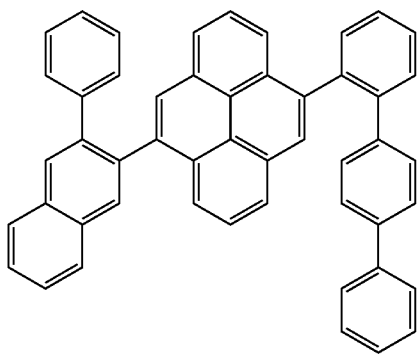
Compound of JP-A-2009-283899
Comparative compound 3
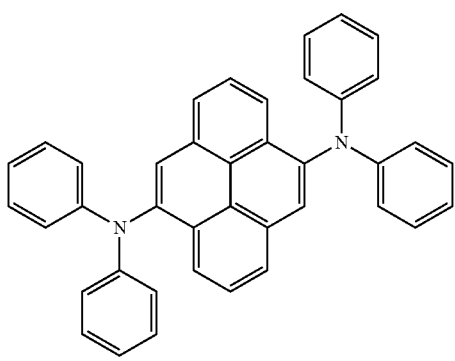
KR10-2011-0057008
Comparative compound 4
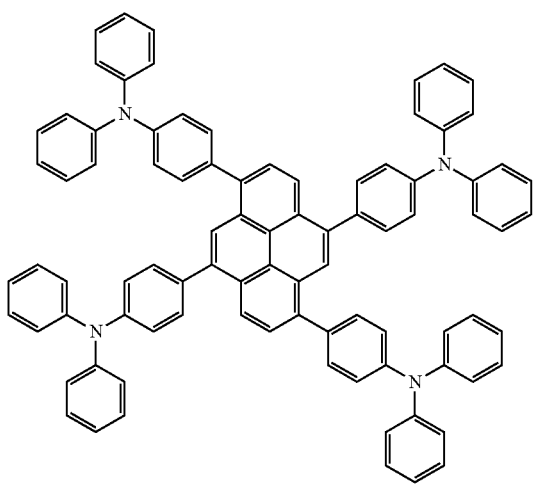
Compound of JP-A-2006-298793
The comparative compounds 1 and 4 are the compounds described in JP-A-2006-298793, the comparative compound 2 is the compound described in JP-A-2009-283899, and the comparative compound 3 is the compound described in KR10-2011-0057008.
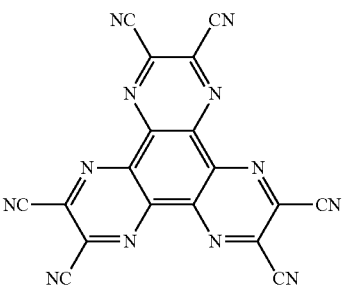
HAT—CN
HT-1
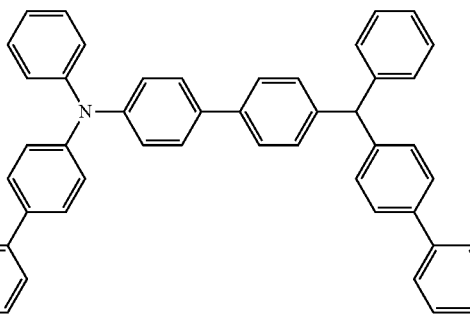
HT-2
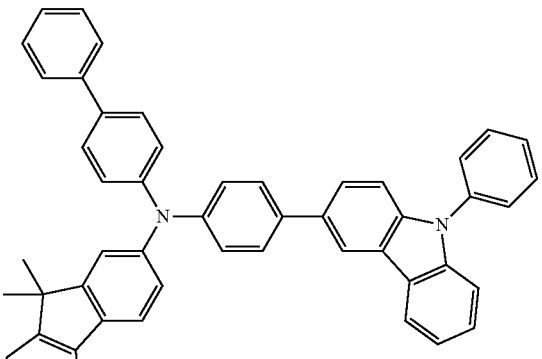
HT-3
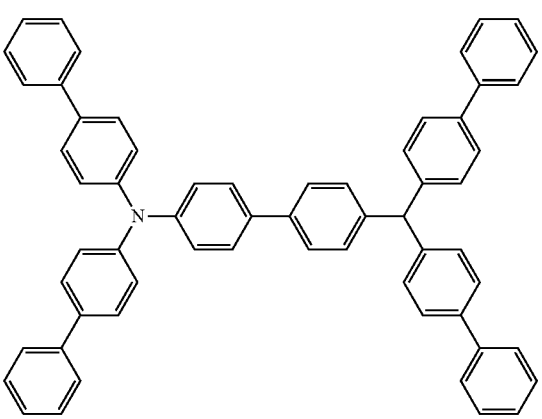

HT-4
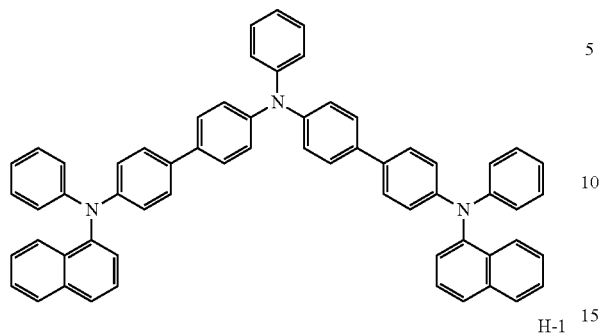
H-1
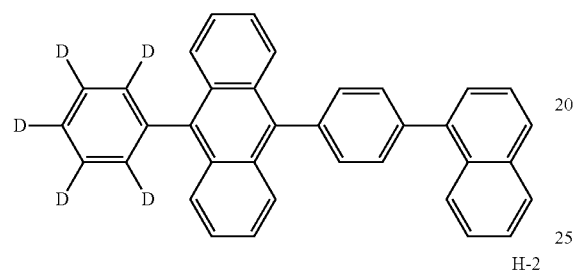
H-2
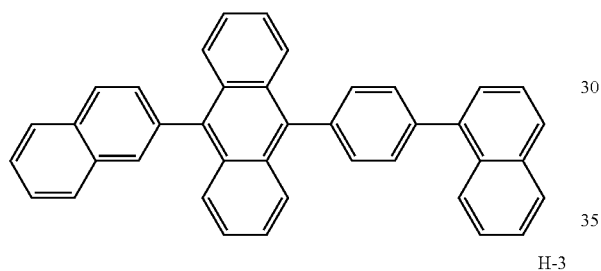
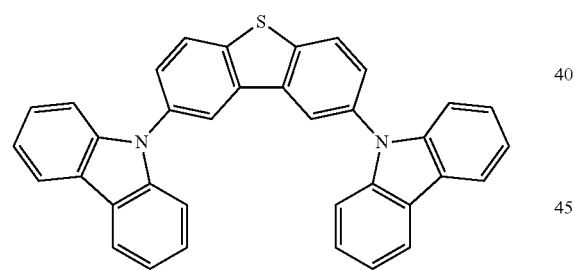
H-3
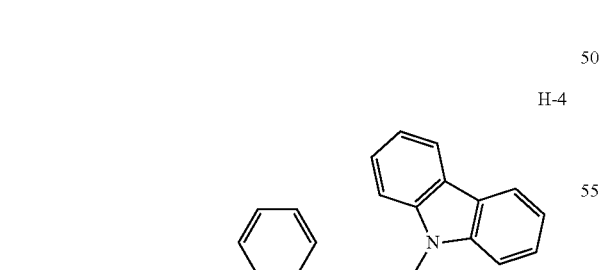
H-4
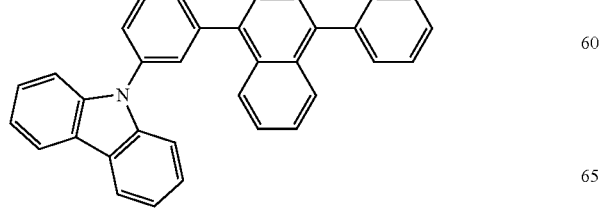
ET-1
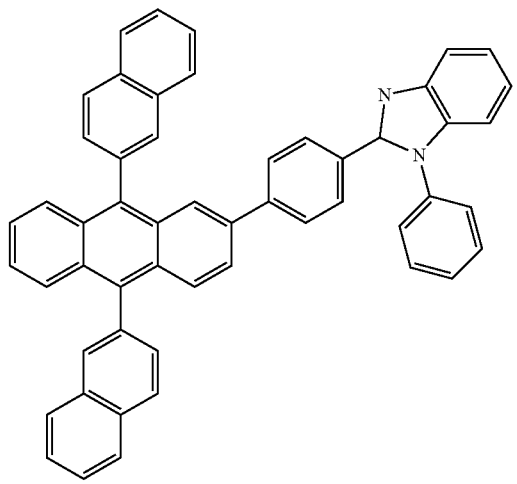
ET-2
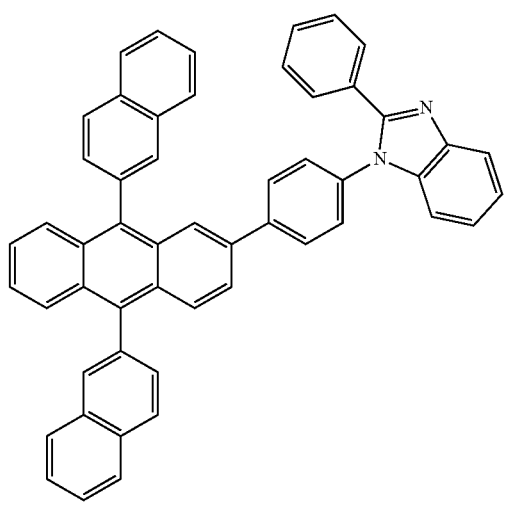
ET-3
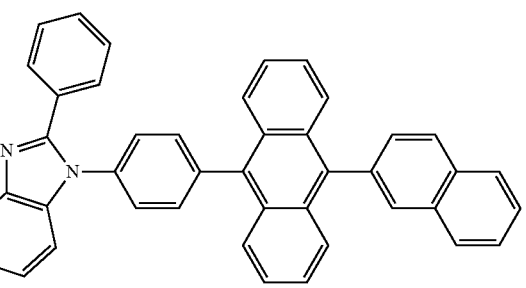
ET-4
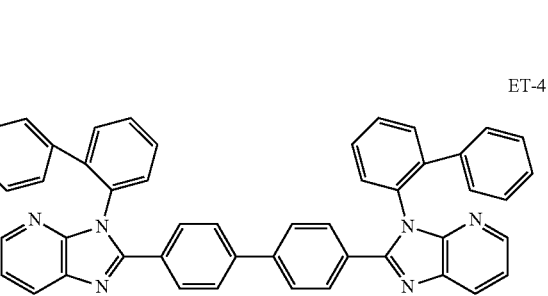

133
-continued

ET-5

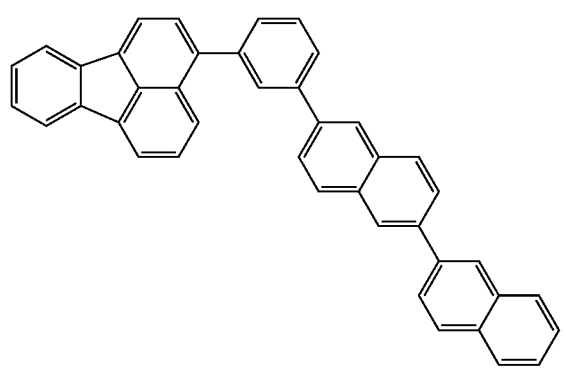

134
Example 1

1. Synthesis of Compounds Represented by General Formula (1)

The compounds represented by the general formula (1) can be synthesized by a combination of known reactions, including the methods descried in JP-A-2009-283899, and JP-A-2006-298793. The following describes representative examples of specific synthesis procedures for the compounds represented by the general formula (1).

Synthesis of Compound 1

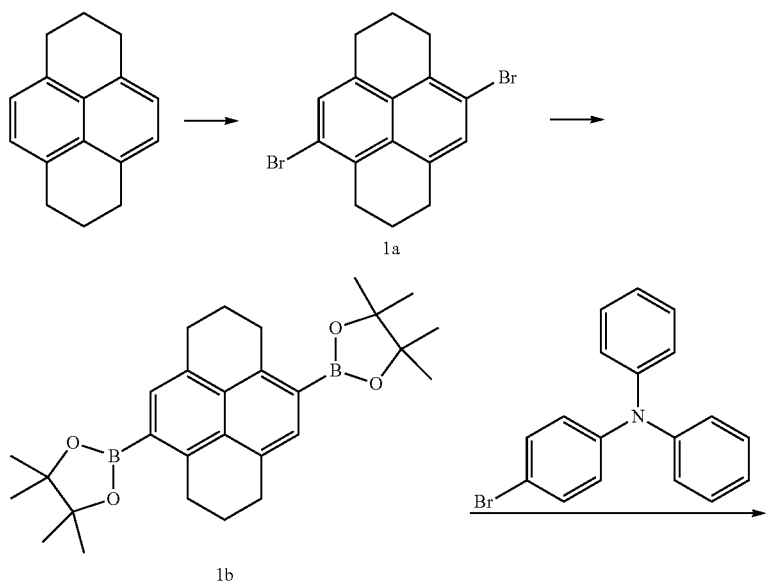

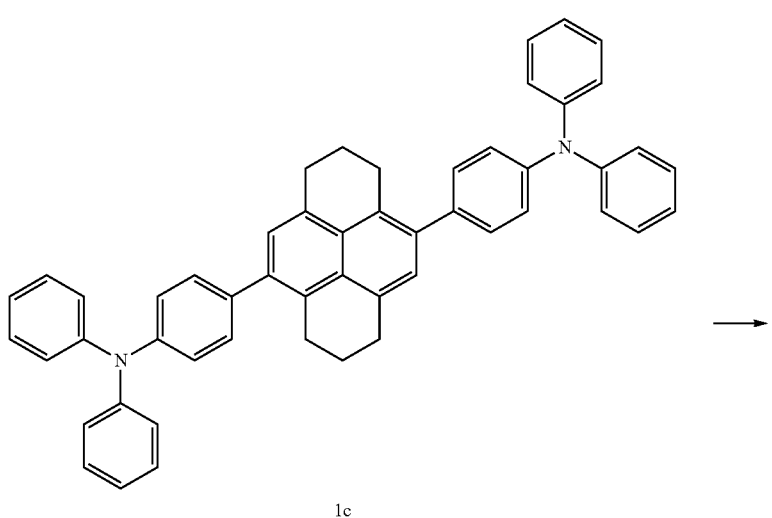

-continued

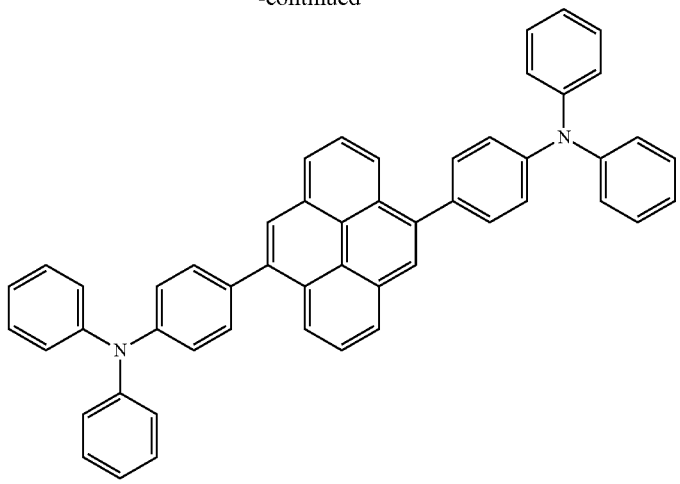

Compound 1

Synthesis of Compound 1a

Bromine (26 ml) was dropped onto a dichloromethane solution (500 ml) of 1,2,3,6,7,8-hexahydropyrene (ALDRICH; 50 g) at room temperature, and the mixture was stirred for 4 hours. The precipitated crystals were filtered, and washed with ethanol and hexane to obtain compound 1a (39 g).

Synthesis of Compound 1b

[1,1'-bis(Diphenylphosphino)ferrocene]palladium(II)dichloride ($PdCl_2$(dppf); 0.8 g) was added to a toluene solution (60 ml) of compound 1a (5 g), bispinacoldiborane (17.4 g), and potassium acetate (4 g), and the mixture was stirred under nitrogen atmosphere at 80° C. for 8 hours. The reaction liquid was Celite filtered, and the filtrate was concentrated under reduced pressure. Ethanol was added to the concentrate residue, and filtered to obtain compound 1b (5.3 g).

Synthesis of Compound 1c

Compound 1b (1 g), 4-bromotriphenylamine (Tokyo Kasei; 1.55 g), 2-dicyclohexylphosphino-2',6'-dimethoxybiphenyl (SPhos; 0.21 g), potassium phosphate (2.3 g), tris(dibenzylideneacetone)dipalladium ($Pd_2$(dba)$_3$; 0.12 g), and toluene/water=2/1 (30 ml) were mixed, and stirred under nitrogen atmosphere at 100° C. for 3 hours. After bringing the reaction liquid back to room temperature, toluene and deionized water were added, and the organic layer was extracted. The organic layer was dried over sodium sulfate, concentrated under reduced pressure, and purified by silica gel column chromatography to obtain compound 1c (1.27 g).

Synthesis of Compound 1

10% Pd/C (31 mg) was stirred in a triglyme solution (100 ml) of compound 1c (1 g) under nitrogen atmosphere at 100° C. for 5 hours. After bringing the reaction liquid back to room temperature, the solution was Celite filtered. Then, toluene and deionized water were added, and the organic layer was extracted. The organic layer was dried over sodium sulfate, and concentrated under reduced pressure. The concentrate residue was recrystallized from ethanol/toluene to obtain compound 1 (0.77 g). The compound was identified by elemental analysis, NMR, and MASS spectrometry. 1H-NMR ($CDCl_3$)

δ(ppm)=: 7.02-7.1 (4H, dd), 7.2-7.38 (20H, m), 7.58 (4H, d), 8.0 (2H, dd), 8.09 (2H, s), 8.21 (2H, d), 8.33 (2H, d)

Compounds 2 to 36 used in Examples were also synthesized by using methods similar to that used for compound 1. Comparative Compounds 1 to 4 were synthesized by referring to known documents describing the compounds.

2. Evaluation of Physical Properties of Materials (a) Evaluation of Chromaticity The following host material H-5 and the respective light emitting materials shown in Table 1 below were deposited on a quartz glass substrate (25 mm×25 mm×0.7 mm) by a vacuum deposition method at a mass ratio (95:5) to form a thin film having a film thickness of 50 nm. The luminous spectrum of the emitted light from the thin film irradiated with 350-nm UV rays was measured using a fluorescence spectrophotometer (FP-6300, manufactured by JASCO Corporation) to determine the chromaticity (x, y). Based on the y value at this time, the chromaticity was evaluated according to the following three criteria. The results are shown in Table 1 below.

Good: $0.04 \leq y \leq 0.09$
Acceptable: $0.03 \leq y < 0.04$, $0.09 < y \leq 0.12$
Poor: $y < 0.03$, $0.12 < y$ Host Compound H-5

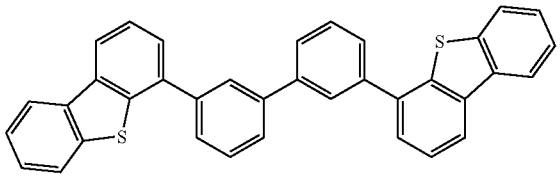

TABLE 1

| Light emitting material | Chromaticity | Note |
|---|---|---|
| Compound 1 | Good | Present invention |
| Compound 3 | Good | Present invention |
| Compound 4 | Good | Present invention |
| Compound 6 | Good | Present invention |
| Compound 7 | Good | Present invention |
| Compound 8 | Acceptable | Present invention |
| Compound 9 | Good | Present invention |
| Compound 11 | Good | Present invention |

TABLE 1-continued

| Light emitting material | Chromaticity | Note |
|---|---|---|
| Compound 12 | Good | Present invention |
| Compound 14 | Good | Present invention |
| Compound 21 | Acceptable | Present invention |
| Comparative compound 1 | Poor | Comparative Example |
| Comparative compound 2 | Poor | Comparative Example |
| Comparative compound 3 | Poor | Comparative Example |
| Comparative compound 4 | Poor | Comparative Example |

Example 2

Production and Evaluation of Organic Electroluminescent Element

The materials used for the production of the organic electroluminescent element were all purified by sublimation, and the purity (absorption intensity area ratio at 254 nm) was confirmed to be 99.9% or higher by high-performance liquid chromatography (Tosoh TSK gel ODS-100Z).

A 0.5 mm-thick and 2.5 cm square glass substrate (product of Geomatec Co., Ltd., surface resistance: 10 Ω/quadrature) having an ITO film thereon was put in a cleaning container. After ultrasonic cleaning in 2-propanol, the glass substrate was subjected to a UV-ozone treatment for 30 minutes. The following organic compound layers were deposited sequentially on the transparent anode (ITO film) by a vacuum deposition method.

Note that the deposition rate in the Examples and Comparative Examples below is 0.1 nm/sec unless otherwise specifically indicated. The deposition rate was measured using a quartz oscillator. In addition, the thicknesses of the respective layers below were measured using the quartz oscillator.

First layer: HAT-CN: thickness 10 nm
Second layer: HT-2: thickness 30 nm
Third layer: H-1 and light emitting material (mass ratio=93:7) shown in Table 2: thickness 30 nm
Fourth layer: ET-1: thickness 30 nm 1 nm of lithium fluoride and 100 nm of metal aluminum were deposited in this order thereon to form a cathode. At this time, a patterned mask (mask having a light emitting area of 2 mm×2 mm) was provided on the layer of lithium fluoride to deposit the metal aluminum.

The obtained laminate was put in a glove box purged with a nitrogen gas without bringing it into contact with the atmosphere, and then sealed with a sealing can made of glass and an ultraviolet curing adhesive (XNR5516HV, manufactured by Nagase Chemical Co., Ltd.) to obtain organic electroluminescent elements 1-1 to 1-11, and comparative organic electroluminescent elements 1-1 to 1-4, in square shapes having a light emitting area of 2 mm×2 mm. In all of the elements, light emitting derived from the light emitting materials was observed. For the respective organic electroluminescent elements thus obtained, the following tests were carried out. The results of evaluations for external quantum efficiency, chromaticity, and chromaticity change after deterioration by driving are presented in Table 2 below.

(a) External Quantum Efficiency

A direct current voltage was applied to each element by using a source measure unit 2400 (Keithley Instruments Inc.) to allow the organic electroluminescent element to emit light. The luminance was measured with a luminance meter (BM-8, manufactured by Topcon Corporation). The emission spectrum and the light emitting wavelength were measured with a spectrum analyzer PMA-11 (Hamamatsu Photonics K. K.). Based on these values, the external quantum efficiency ($\eta$) at a luminance in the vicinity of 1,000 cd/m$^2$ was calculated by using a luminance conversion method, and shown as a relative value, taking the value of the comparative element 1-1 (organic electroluminescent element using the comparative compound 1) as 1.0. Larger numeral values are preferable, because larger values indicate better efficiency.

(b) Chromaticity

The chromaticity (x, y) was determined from the luminous spectrum of the light emitted at a luminance of 1,000 cd/m$^2$ after a direct current voltage was applied to each organic electroluminescent element. From the y values at the time, the chromaticity was evaluated according to the following three criteria.

Good: $0.04 \leq y \leq 0.09$
Acceptable: $0.03 \leq y < 0.04$, $0.09 < y \leq 0.12$
Poor: $y < 0.03$, $0.12 < y$ (c) Chromaticity after Deterioration by Driving DC voltage was continuously applied to cause each organic electroluminescent element to emit light at a luminance of 1,000 cd/m$^2$, and the chromaticity (x', y') after the luminance decreased to 500 cd/m$^2$ was measured from the emission spectrum. Chromaticity change after deterioration by driving was evaluated according to the following three criteria, using changes in y values $\Delta y$ ($=|y'-\Delta y|$) before and after the deterioration by driving.

Good: $\Delta y \leq 0.01$
Acceptable: $0.01 < \Delta y \leq 0.02$
Poor: $0.02 < \Delta y$

TABLE 2

| Element No. | Light emitting material | Relative external quantum efficiency | Chromaticity | Chromaticity after deterioration by driving | Note |
|---|---|---|---|---|---|
| Element 1-1 | Compound 1 | 1.1 | Good | Good | Present Invention |
| Element 1-2 | Compound 3 | 1.2 | Good | Good | Present Invention |
| Element 1-3 | Compound 4 | 1.1 | Good | Good | Present Invention |
| Element 1-4 | Compound 6 | 1.2 | Good | Good | Present Invention |
| Element 1-5 | Compound 7 | 1.2 | Good | Good | Present Invention |
| Element 1-6 | Compound 8 | 1.2 | Acceptable | Good | Present Invention |
| Element 1-7 | Compound 9 | 1.3 | Good | Good | Present Invention |

TABLE 2-continued

| Element No. | Light emitting material | Relative external quantum efficiency | Chromaticity | Chromaticity after deterioration by driving | Note |
|---|---|---|---|---|---|
| Element 1-8 | Compound 11 | 1.3 | Good | Good | Present Invention |
| Element 1-9 | Compound 12 | 1.3 | Good | Good | Present Invention |
| Element 1-10 | Compound 14 | 1.2 | Good | Good | Present Invention |
| Element 1-11 | Compound 21 | 1.1 | Acceptable | Good | Present Invention |
| Comparative element 1-1 | Comparative compound 1 | 1.0 | Poor | Acceptable | Comparative Example |
| Comparative element 1-2 | Comparative compound 2 | Emission from host material | Poor | Acceptable | Comparative Example |
| Comparative element 1-3 | Comparative compound 3 | 0.2 | Poor | Poor | Comparative Example |
| Comparative element 1-4 | Comparative compound 4 | 0.8 | Poor | Poor | Comparative Example |

Example 3

Organic electroluminescent elements 2-1 to 2-11 and comparative elements 2-1 to 2-4 were produced in the same manner as in Example 2, except that the layer configurations were changed as follows. Evaluations were carried out in the same manner as in Example 2. The results are presented in Table 3 below. Note that the external quantum efficiency shown in Table 3 below is shown as a relative value, taking the value of the comparative element 2-1 (organic electroluminescent element using comparative compound 1) as 1.0.

First layer: HT-4: thickness 50 nm
Second layer: HT-3: thickness 45 nm
Third layer: H-2 and light emitting material (mass ratio=95:5) shown in Table 3: thickness 25 nm
Fourth layer: ET-5: thickness 5 nm
Fifth layer: ET-3: thickness 20 nm

TABLE 3

| Element No. | Light emitting material | Relative external quantum efficiency | Chromaticity | Chromaticity after deterioration by driving | Note |
|---|---|---|---|---|---|
| Element 2-1 | Compound 1 | 1.1 | Good | Good | Present Invention |
| Element 2-2 | Compound 3 | 1.2 | Good | Good | Present Invention |
| Element 2-3 | Compound 4 | 1.1 | Good | Good | Present Invention |
| Element 2-4 | Compound 6 | 1.2 | Good | Good | Present Invention |
| Element 2-5 | Compound 7 | 1.2 | Good | Good | Present Invention |
| Element 2-6 | Compound 8 | 1.2 | Acceptable | Good | Present Invention |
| Element 2-7 | Compound 9 | 1.3 | Good | Good | Present Invention |
| Element 2-8 | Compound 11 | 1.3 | Good | Good | Present Invention |
| Element 2-9 | Compound 12 | 1.3 | Good | Good | Present Invention |
| Element 2-10 | Compound 14 | 1.2 | Good | Good | Present Invention |
| Element 2-11 | Compound 21 | 1.1 | Acceptable | Good | Present Invention |
| Comparative element 2-1 | Comparative compound 1 | 1.0 | Poor | Acceptable | Comparative Example |
| Comparative element 2-2 | Comparative compound 2 | Emission from host material | Poor | Acceptable | Comparative Example |
| Comparative element 2-3 | Comparative compound 3 | 0.3 | Poor | Poor | Comparative Example |
| Comparative element 2-4 | Comparative compound 4 | 0.7 | Poor | Poor | Comparative Example |

Example 4

Organic electroluminescent elements 3-1 to 3-11 and comparative elements 3-1 to 3-4 were produced in the same manner as in Example 2, except that the layer configurations were changed as follows. Evaluations were carried out in the same manner as in Example 2. The results are presented in Table 4 below. Note that the external quantum efficiency shown in Table 4 below is shown as a relative value, taking the value of the comparative element 3-1 (organic electroluminescent element using comparative compound 1) as 1.0.

First layer: HAT-CN: thickness 10 nm
Second layer: HT-2: thickness 30 nm
Third layer: H-1 and light emitting material (mass ratio=95:5) shown in Table 4: thickness 30 nm
Fourth layer: ET-4: thickness 30 nm

TABLE 4

| Element No. | Light emitting material | Relative external quantum efficiency | Chromaticity | Chromaticity after deterioration by driving | Note |
| --- | --- | --- | --- | --- | --- |
| Element 3-1 | Compound 1 | 0.9 | Good | Good | Present Invention |
| Element 3-2 | Compound 3 | 1.1 | Good | Good | Present Invention |
| Element 3-3 | Compound 4 | 0.9 | Good | Good | Present Invention |
| Element 3-4 | Compound 6 | 1.1 | Good | Good | Present Invention |
| Element 3-5 | Compound 7 | 1.1 | Good | Good | Present Invention |
| Element 3-6 | Compound 8 | 1.1 | Acceptable | Good | Present Invention |
| Element 3-7 | Compound 9 | 1.2 | Good | Good | Present Invention |
| Element 3-8 | Compound 11 | 1.2 | Good | Good | Present Invention |
| Element 3-9 | Compound 12 | 1.2 | Good | Good | Present Invention |
| Element 3-10 | Compound 14 | 1.1 | Good | Good | Present Invention |
| Element 3-11 | Compound 21 | 0.9 | Acceptable | Good | Present Invention |
| Comparative element 3-1 | Comparative compound 1 | 1.0 | Poor | Acceptable | Comparative Example |
| Comparative element 3-2 | Comparative compound 2 | Emission from host material | Poor | Acceptable | Comparative Example |
| Comparative element 3-3 | Comparative compound 3 | 0.2 | Poor | Poor | Comparative Example |
| Comparative element 3-4 | Comparative compound 4 | 0.7 | Poor | Poor | Comparative Example |

Example 5

Organic electroluminescent elements were produced in the same manner as in Example 2, except that the layer configurations were changed as follows. Evaluations were carried out in the same manner as in Example 2. The results are presented in Table 5 below. Note that the external quantum efficiency shown in Table 5 below is shown as a relative value, taking the value of the comparative element 4-1 (organic electroluminescent element using comparative compound 1) as 1.0.

First layer: HAT-CN: thickness 10 nm

Second layer: HT-1: thickness 30 nm

Third layer: H-3 and light emitting material (mass ratio=93:7) shown in Table 5: thickness 30 nm Fourth layer: ET-4: thickness 30 nm

TABLE 5

| Element No. | Light emitting material | Relative external quantum efficiency | Chromaticity | Chromaticity after deterioration by driving | Note |
| --- | --- | --- | --- | --- | --- |
| Element 4-1 | Compound 1 | 0.9 | Good | Good | Present Invention |
| Element 4-2 | Compound 3 | 1.1 | Good | Good | Present Invention |
| Element 4-3 | Compound 4 | 1.0 | Good | Good | Present Invention |
| Element 4-4 | Compound 6 | 1.1 | Good | Good | Present Invention |
| Element 4-5 | Compound 7 | 1.1 | Good | Good | Present Invention |
| Element 4-6 | Compound 8 | 1.1 | Acceptable | Good | Present Invention |
| Element 4-7 | Compound 9 | 1.2 | Good | Good | Present Invention |
| Element 4-8 | Compound 11 | 1.1 | Good | Good | Present Invention |
| Element 4-9 | Compound 12 | 1.2 | Good | Good | Present Invention |
| Element 4-10 | Compound 14 | 1.1 | Good | Good | Present Invention |
| Element 4-11 | Compound 21 | 0.9 | Acceptable | Good | Present Invention |
| Comparative element 4-1 | Comparative compound 1 | 1.0 | Poor | Acceptable | Comparative Example |
| Comparative element 4-2 | Comparative compound 2 | 0.2 | Poor | Acceptable | Comparative Example |
| Comparative element 4-3 | Comparative compound 3 | 0.4 | Poor | Poor | Comparative Example |
| Comparative element 4-4 | Comparative compound 4 | 0.9 | Poor | Poor | Comparative Example |

Example 6

Organic electroluminescent elements were produced in the same manner as in Example 2, except that the layer configurations were changed as follows. Evaluations were carried out in the same manner as in Example 2. The results are presented in Table 6 below. Note that the external quantum efficiency shown in Table 6 below is shown as a relative value, taking the value of the comparative element 5-1 (organic electroluminescent element using comparative compound 1) as 1.0.

First layer: HAT-CN: thickness 10 nm
Second layer: HT-2: thickness 30 nm
Third layer: H-4 and light emitting material (mass ratio=93:7) shown in Table 6: thickness 30 nm
Fourth layer: ET-2: thickness 30 nm

TABLE 6

| Element No. | Light emitting material | Relative external quantum efficiency | Chromaticity | Chromaticity after deterioration by driving | Note |
| --- | --- | --- | --- | --- | --- |
| Element 5-1 | Compound 1 | 1.0 | Good | Good | Present Invention |
| Element 5-2 | Compound 3 | 1.1 | Good | Good | Present Invention |
| Element 5-3 | Compound 4 | 0.9 | Good | Good | Present Invention |
| Element 5-4 | Compound 6 | 1.1 | Good | Good | Present Invention |
| Element 5-5 | Compound 7 | 1.1 | Good | Good | Present Invention |
| Element 5-6 | Compound 8 | 1.1 | Acceptable | Good | Present Invention |
| Element 5-7 | Compound 9 | 1.3 | Good | Good | Present Invention |
| Element 5-8 | Compound 11 | 1.2 | Good | Good | Present Invention |
| Element 5-9 | Compound 12 | 1.2 | Good | Good | Present Invention |
| Element 5-10 | Compound 14 | 1.2 | Good | Good | Present Invention |
| Element 5-11 | Compound 21 | 1.0 | Acceptable | Good | Present Invention |

TABLE 6-continued

| Element No. | Light emitting material | Relative external quantum efficiency | Chromaticity | Chromaticity after deterioration by driving | Note |
|---|---|---|---|---|---|
| Comparative element 5-1 | Comparative compound 1 | 1.0 | Poor | Acceptable | Comparative Example |
| Comparative element 5-2 | Comparative compound 2 | Emission from host material | Poor | Acceptable | Comparative Example |
| Comparative element 5-3 | Comparative compound 3 | 0.1 | Poor | Poor | Comparative Example |
| Comparative element 5-4 | Comparative compound 4 | 0.8 | Poor | Poor | Comparative Example |

Example 7

Evaluation of Organic Electroluminescent Element (Coating) Preparation of Light Emitting Layer-Forming Coating Liquids 1 to 6 and Comparative Light Emitting Layer-Forming Coating Liquids 1 and 2

Compound 5 as a light emitting material (0.1% by mass), a host material PH-1 having the following structure (0.9% by mass), and methyl ethyl ketone (98.99% by mass) were mixed to obtain a light emitting layer-forming coating liquid 1.

Light emitting layer-forming coating liquids 2 and 3 were prepared in the same manner as for the light emitting layer-forming coating liquid 1, except that the compound 5 in the light emitting layer-forming coating liquid 1 was changed to compounds 11 and 17. For comparison, comparative light emitting layer-forming coating liquid 1 was prepared in the same manner as for the light emitting layer-forming coating liquid 1, except that the compound 5 in the light emitting layer-forming coating liquid 1 was changed to comparative compound 2.

Further, light emitting layer-forming coating liquids 4 to 6, and a comparative light emitting layer-forming coating liquid 2 were prepared in the same manner as for the light emitting layer-forming coating liquids 1 to 3 and the comparative light emitting layer-forming coating liquid 1, except that the host material PH-1 in the light emitting layer-forming coating liquids 1 to 3 and in the comparative light emitting layer-forming coating liquid 1 was changed to a host material H-2.

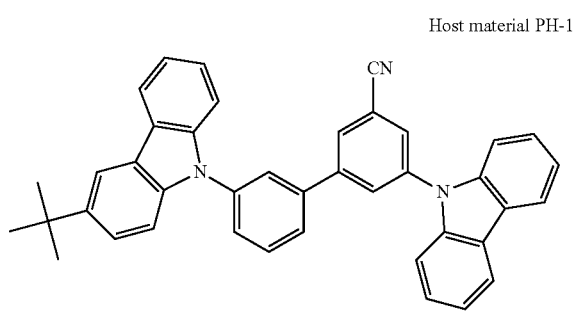 [SMILES: CC(C)(C)c1ccc2c(c1)c1ccccc1n2-c1cccc(-c2cc(C#N)cc(-n3c4ccccc4c4ccccc43)c2)c1]

Host material PH-1

Preparation of Organic Electroluminescent Element P1

ITO was deposited on a glass substrate (25 mm×25 mm×0.7 mm) to give a thickness of 150 nm, thereby forming a film. The film was taken as a transparent supporting substrate. This transparent supporting substrate was etched and washed.

On this ITO glass substrate, 2 parts by mass of PTPDES-2 represented by the following structural formula (manufactured by Chemipro Kasei Kaisha, Ltd., Tg=205° C.) was dissolved in 98 parts by mass of cyclohexanone for the Electronics Industry (manufactured by Kanto Chemical Co., Inc.) and spin-coated (2,000 rpm, 20 seconds) to give a thickness of about 40 nm, and then dried at 120° C. for 30 minutes and subjected to an annealing treatment at 160° C. for 10 minutes to form a hole injecting layer.

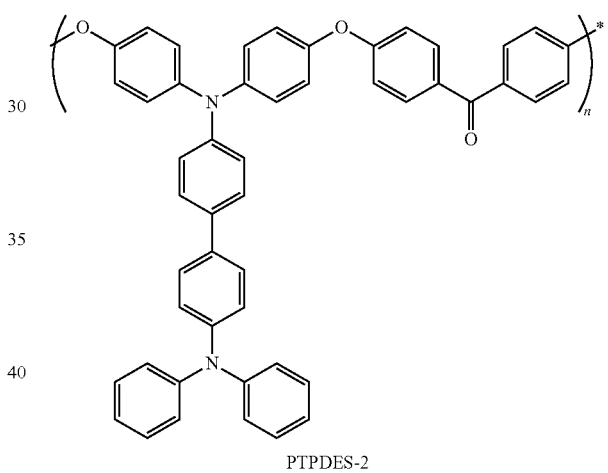

PTPDES-2

The coating liquid 1 for forming a light emitting layer was spin-coated on a hole injecting layer (1,300 rpm, 30 seconds) to give a thickness of about 40 nm, thereby obtaining a light emitting layer.

Subsequently, BAlq (bis-(2-methyl-8-quinolato)-4-(phenylphenolate)-aluminum (III)) represented by the following structural formula was formed as an electron transporting layer on a light emitting layer to give a thickness of 40 nm by a vacuum deposition method.

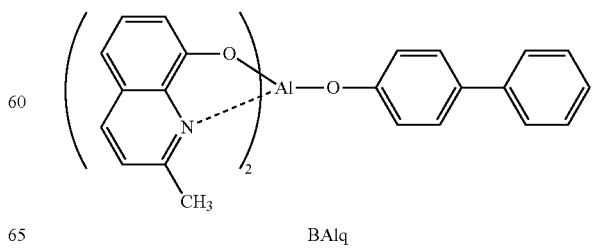

BAlq

Lithium fluoride (LiF) was formed as an electron injecting layer on an electron transporting layer to give a thickness of 1 nm by a vacuum deposition method. Metal aluminum was further deposited to 70 nm thereon to give a cathode.

The laminate thus prepared was put into a globe box purged with an argon gas, and then sealed with a sealing can made of stainless steel and an ultraviolet curing adhesive (XNR5516HV, manufactured by Nagase Chemical Co., Ltd.) to obtain an organic electroluminescent element P1.
Production of Organic Electroluminescent Elements P2 to P8

Organic electroluminescent elements P2 to P6 were produced in the same manner as for the organic electroluminescent element P1, except that the light emitting layer-forming coating liquid 1 was changed to the light emitting layer-forming coating liquids 2 to 6 in production of the organic electroluminescent element P1.

For comparison, organic electroluminescent elements P7 and P8 were produced in the same manner as for the organic electroluminescent element P1, except that the light emitting layer-forming coating liquid 1 was changed to the comparative light emitting layer-forming coating liquids 1 and 2 in production of the organic electroluminescent element P1.
Evaluation Evaluation was carried out for the organic electroluminescent elements P1 to P8 in the same manner as in Example 2. The results are shown in Table 7 below. Note that the external quantum efficiency in Table 7 below is shown as a relative value, taking the values of the organic electroluminescent elements P7 and P8 that use the comparative compound 2 as 1.0.

TABLE 7

| Organic electroluminescent element | Light emitting material | Host material | Relative external quantum efficiency | Chromaticity | Chromaticity change after deterioration by driving | Note |
|---|---|---|---|---|---|---|
| P1 | Compound 5 | PH-1 | 3.9 | Good | Good | Present Invention |
| P2 | Compound 11 | PH-1 | 5.3 | Good | Good | Present Invention |
| P3 | Compound 17 | PH-1 | 5.1 | Good | Good | Present Invention |
| P7 | Comparative compound 2 | PH-1 | 1.0 | Poor | Acceptable | Comparative Example |
| P4 | Compound 5 | H-2 | 3.8 | Good | Good | Present Invention |
| P5 | Compound 11 | H-2 | 5.4 | Good | Good | Present Invention |
| P6 | Compound 17 | H-2 | 5.1 | Good | Good | Present Invention |
| P8 | Comparative compound 2 | H-2 | 1.0 | Poor | Acceptable | Comparative Example |

It was found from the results presented in these tables, the organic electroluminescent elements using the compounds of the present invention as light emitting material had sufficient luminous efficiency, and excellent chromaticity. In a preferred aspect of the present invention, chromaticity change after deterioration by driving was excellent.

On the other hand, the comparative elements using the comparative compound 1 described in JP-A-2006-298793 was found to be inferior in terms of chromaticity, and chromaticity change after deterioration by driving.

The invention claimed is:
1. An organic electroluminescent element comprising:
a substrate;
a pair of electrodes including an anode and a cathode, disposed on the substrate; and
an organic layer disposed between the electrodes,
wherein the organic layer consists of a single host and at least one light emitting material represented by one of General Formula (5) to General Formula (7)

General Formula (5)

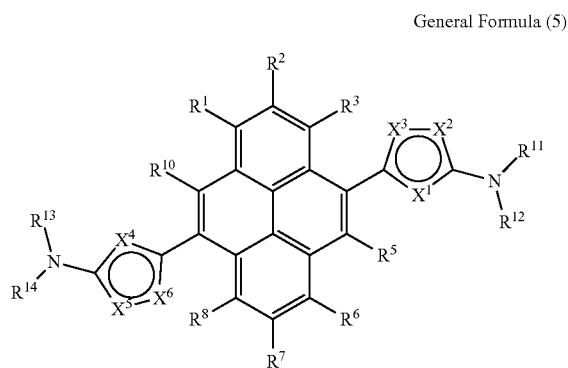

wherein, in General Formula (5),
$R^1$ to $R^3$ and $R^6$ to $R^8$ each independently represents a hydrogen atom, which may be a deuterium atom, or a substituent with a Hammett substituent constant $\sigma_p$ value of −0.15 or more,
$R^5$ and $R^{10}$ each independently represents a hydrogen atom or a substituent,
$R^{11}$ to $R^{14}$ each independently represents an alkyl group, an aryl group or a heteroaryl group,
$X^1$ to $X^6$ each independently represents CRz, wherein two adjacent CRzs may jointly form a five- or a six-membered ring, —N═, NRy, O or S, and Rz and Ry each independently represents a hydrogen atom or a substituent,
wherein $R^1$ to $R^3$, $R^5$ to $R^8$, $R^{10}$ to $R^{14}$ and $X^1$ to $X^6$ are not bound to each other to form a ring, provided that when $X^1$ is O or S, then one of $X^2$ and $X^3$ is —N═ and the other of $X^2$ and $X^3$ is CRz; and
provided that when $X^4$ is O or S, then one of $X^5$ and $X^6$ is —N═ and the other of $X^5$ and $X^6$ is CRz;

General Formula (6)

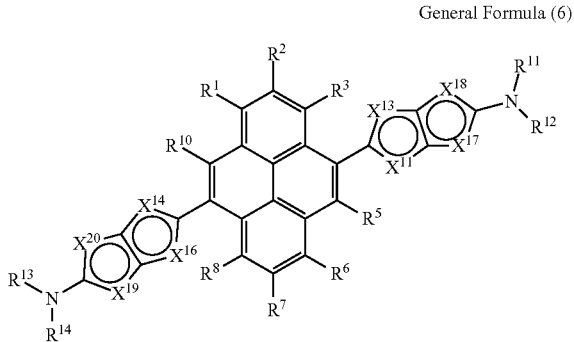

wherein, in General Formula (6),
$R^1$ to $R^3$ and $R^6$ to $R^8$ each independently represents a hydrogen atom, which may be a deuterium atom, or a substituent with a Hammett substituent constant $\sigma_p$ value of −0.15 or more,
$R^5$ and $R^{10}$ each independently represents a hydrogen atom or a substituent,
$R^{11}$ to $R^{14}$ each independently represents an alkyl group, an aryl group or a heteroaryl group,
$X^{11}$, $X^{13}$, $X^{14}$ and $X^{16}$ to $X^{20}$ each independently represents CRz, wherein two adjacent CRzs may jointly form a five- or a six-membered ring, —N═, NRy, O or S, and Rz and Ry each independently represents a hydrogen atom or a substituent,
wherein $R^1$ to $R^3$, $R^5$ to $R^8$, $R^{10}$ to $R^{14}$, $X^{11}$, $X^{13}$, $X^{14}$ and $X^{16}$ to $X^{20}$ are not bound to each other to form a ring,
provided that $X^{20}$ and $X^{16}$ are not both S, $X^{14}$ and $X^{19}$ are not both S, $X^{13}$ and $X^{17}$ are not both S, and $X^{11}$ and $X^{18}$ are not both S General Formula (7)

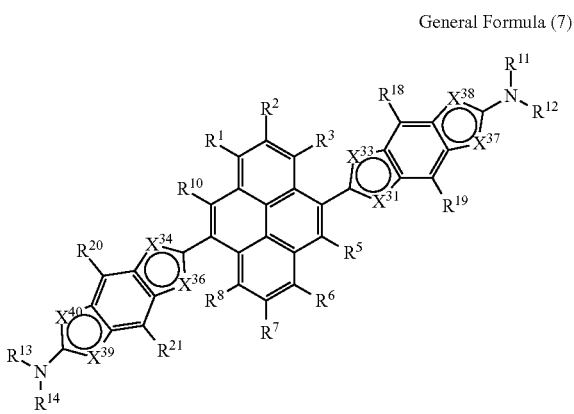

wherein, in General Formula (7),
$R^1$ to $R^3$ and $R^6$ to $R^8$ each independently represents a hydrogen atom, which may be a deuterium atom, or a substituent with a Hammett substituent constant $\sigma_p$ value of −0.15 or more,
$R^5$ and $R^{10}$ each independently represents a hydrogen atom or a substituent,
$R^{11}$ to $R^{14}$ each independently represents an alkyl group, an aryl group or a heteroaryl group,
$R^{18}$ to $R^{21}$ each independently represents a hydrogen atom, a fluorine atom, an alkyl group, a silyl group, an aryl group, a heteroaryl group, —$NY^{21}Y^{22}$, —$OY^{23}$ or —$SY^{24}$, wherein $Y^{21}$ to $Y^{24}$ each independently represents an alkyl group, an aryl group or a heteroaryl group, and which may have further substituents,
$X^{31}$, $X^{33}$, $X^{34}$ and $X^{36}$ to $X^{40}$ each independently represents CRz, wherein two adjacent CRzs may jointly form a five- or a six-membered ring, —N═, NRy, O or S, and Rz and Ry each independently represents a hydrogen atom or a substituent,
wherein $R^1$ to $R^3$, $R^5$ to $R^8$, $R^{10}$ to $R^{14}$, $R^{18}$ to $R^{21}$, $X^{31}$, $X^{33}$, $X^{34}$ and $X^{36}$ to $X^{40}$ are not bound to each other to form a ring
provided that at least one of conditions (i) and (ii) is true:
(i) at least one of $X^{31}$, $X^{33}$, $X^{34}$ and $X^{36}$ to $X^{40}$ represents CRz;
(ii) at least one of $X^{31}$, $X^{33}$, $X^{34}$ and $X^{36}$ to $X^{40}$ represents NRy, wherein Ry does not represent methyl or phenyl.

2. The organic electroluminescent element according to claim 1, wherein in the General Formula (5) to General Formula (7) $R^1$ to $R^3$ and $R^6$ to $R^8$ each independently represents a hydrogen atom, which may be a deuterium atom, an alkyl group, an aryl group, a heteroaryl group, a silyl group, an alkoxy group, an alkylthio group, an aryloxy group, an arylthio group, a halogen atom or a cyano group, and which may have further substituents.

3. The organic electroluminescent element according to claim 1, wherein the organic layer is a light emitting layer formed by a vacuum deposition process.

4. The organic electroluminescent element according to claim 1, wherein the organic layer is a light emitting layer formed by a wet process.

5. A device comprising the organic electroluminescent element according to claim 1, wherein the device is a light emitting device, display device, or illumination device.

6. The electroluminescent element according to claim 1, wherein the host has a hydrocarbon fused ring structure of 10 to 50 carbon atoms.

7. The electroluminescent element according to claim 6, wherein the host is a naphthalene-based host, an anthracene-based host, a phenanthrene-based host, a triphenylene-based host, or a pyrene-based host.

8. The electroluminescent element according to claim 7, wherein the host is an anthracene-based host.

9. The electroluminescent element according to claim 1, wherein the host is selected from the group consisting of a carbazole or derivative thereof, a dibenzothiophene or derivative thereof, a dibenzofuran or derivative thereof, an arylamine or derivative thereof, and a metal complex.

10. The electroluminescent element according to claim 1, wherein the organic layer contains light emitting material represented by one of General Formula (5) to General Formula (7) in the amount of 2% to 20% by mass, based on the total mass of the organic layer.

11. The electroluminescent element according to claim 10, wherein the organic layer contains light emitting material represented by one of General Formula (5) to General Formula (7) in the amount of 3% to 10% by mass, based on the total mass of the organic layer.

* * * * *